US010016393B2

(12) United States Patent
Huang et al.

(10) Patent No.: US 10,016,393 B2
(45) Date of Patent: *Jul. 10, 2018

(54) STABILIZED PHARMACEUTICAL DOSAGE FORMS COMPRISING ATRASENTAN

(71) Applicant: AbbVie Inc., North Chicago, IL (US)

(72) Inventors: Ye Huang, Gurnee, IL (US); Andrew K. Koski, Hoffman Estates, IL (US); Katherine E. Peterson, Wadsworth, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/154,710

(22) Filed: May 13, 2016

(65) Prior Publication Data
US 2016/0250186 A1 Sep. 1, 2016

Related U.S. Application Data

(63) Continuation of application No. 14/324,603, filed on Jul. 7, 2014, now Pat. No. 9,364,458.

(60) Provisional application No. 61/843,799, filed on Jul. 8, 2013.

(51) Int. Cl.
A61K 31/40 (2006.01)
A61K 31/4025 (2006.01)
A61K 47/20 (2006.01)
A61K 47/38 (2006.01)
A61K 9/20 (2006.01)
A61K 9/24 (2006.01)
A61K 9/28 (2006.01)

(52) U.S. Cl.
CPC .......... A61K 31/4025 (2013.01); A61K 9/209 (2013.01); A61K 9/2013 (2013.01); A61K 9/2018 (2013.01); A61K 9/2054 (2013.01); A61K 9/2866 (2013.01); A61K 9/2893 (2013.01); A61K 47/20 (2013.01); A61K 47/38 (2013.01)

(58) Field of Classification Search
CPC .. A61K 31/4025; A61K 9/2893; A61K 9/209; A61K 9/2054; A61K 9/2866; A61K 9/2018; A61K 9/2013; A61K 47/38; A61K 47/20
USPC ........................................................ 514/423
See application file for complete search history.

(56) References Cited

U.S. PATENT DOCUMENTS

| 5,622,971 | A | 4/1997 | Winn et al. |
| 5,731,434 | A | 3/1998 | Winn et al. |
| 5,767,144 | A | 6/1998 | Winn et al. |
| 5,801,250 | A | 9/1998 | Oliver-Shaffer et al. |
| 6,124,341 | A | 9/2000 | Tasker et al. |
| 6,162,927 | A | 12/2000 | Winn et al. |
| 6,329,536 | B1 | 12/2001 | Ji et al. |
| 6,380,241 | B1 | 4/2002 | Winn et al. |
| 6,462,194 | B1 | 10/2002 | Winn et al. |
| 6,946,481 | B1 | 9/2005 | Winn et al. |
| 7,208,517 | B1 | 4/2007 | Winn et al. |
| 7,297,709 | B2 | 11/2007 | Dai et al. |
| 7,365,093 | B2 | 4/2008 | Winn et al. |
| 7,598,283 | B2 | 10/2009 | Dai et al. |
| 8,063,091 | B2 | 11/2011 | Dai et al. |
| 9,364,458 | B2 * | 6/2016 | Huang ............... A61K 31/4025 |
| 2002/0055457 | A1 | 5/2002 | Janus et al. |
| 2003/0022811 | A1 | 1/2003 | Singh et al. |
| 2003/0092757 | A1 | 5/2003 | Singh et al. |
| 2005/0113306 | A1 | 5/2005 | Janus et al. |
| 2005/0113307 | A1 | 5/2005 | Janus et al. |
| 2006/0035867 | A1 | 2/2006 | Janus et al. |
| 2007/0123582 | A1 | 5/2007 | Zhang |
| 2008/0132710 | A1 | 6/2008 | Henry et al. |
| 2010/0184026 | A1 | 7/2010 | Lesniewski et al. |
| 2013/0030189 | A1 | 1/2013 | Dai et al. |

FOREIGN PATENT DOCUMENTS

| KR | 20110119108 A | 11/2011 |
| WO | 1991011172 A1 | 8/1991 |
| WO | 1994002518 A1 | 2/1994 |
| WO | 1998055148 A1 | 12/1998 |
| WO | 2006034084 A1 | 3/2006 |
| WO | 2006034085 A1 | 3/2006 |
| WO | 2006034094 A1 | 3/2006 |
| WO | 2006034234 A1 | 3/2006 |

OTHER PUBLICATIONS

Gennaro, Remington's Pharmaceutical Sciences, 1990, Mack Publishing Co., Easton Pennsylvannia, p. 1633-1637, (8 pages including the cover sheets).*
Abbott, "XINLAY™ (atrasentan hydrochloride)" Oncologic Drugs Advisory Committee, Briefing Document for Atrasentan (Xinlay™), Atrasentan (ABT-627), Sep. 13, 2005, 118 pages.
Andress et al., "Clinical efficacy of the selective endothelin A receptor antagonist, atrasentan, in patients with diabetes and chronic kidney disease (CKD)," Life Sciences, (2012), vol. 91, doi: 10.1016/j.lfs.2012.01.011, pp. 739-742.
Anonymous, "Overview of pharmaceutical excipients used in tablets and capsules," Drug Topics, Voice of the Pharmacist, Oct. 24, 2008, Published at http://drugtopics.modernmedicine.com, 15 pages.
Borsook et al., "Oxidation-Reduction Potential of Ascorbic Acid (Vitamin C)," PNAS, 1933, vol. 19, No. 9, pp. 875-878.
Celestino et al., "Rational use of antioxidants in solid oral pharmaceutical preparations," Brazilian Journal of Pharmaceutical Sciences, 2012, vol. 48, No. 3, pp. 405-415.

(Continued)

Primary Examiner — Taylor V Oh

(57) ABSTRACT

The present disclosure relates to: (a) methods of using stabilized pharmaceutical dosage forms comprising atrasentan, or a pharmaceutically acceptable salt thereof, and, optionally, another therapeutic agent to treat type 2 diabetes, microalbuminuria or macroalbuminuria; and (b) methods for the preparation of such pharmaceutical dosage forms.

11 Claims, No Drawings

(56) References Cited

OTHER PUBLICATIONS

Crowley, Patrick J. "Excipients as stabilizers," Pharmaceutical Science & Technology Today, 1999, vol. 2, No. 6, pp. 237-243.
El-Maali, Nagwa Abo, "Voltammetric Analysis of Drugs" Bioelectrochemistry, 2004, vol. 64, No. 1, pp. 99-107.
Emea, "Committee for Proprietary Medicinal Products; Note for Guidance on Excipients, Antioxidants and Antimicrobial Preservatives in the Dossier for Application for Marketing Authorisation of a Medicinal Product," Feb. 20, 2003, Draft of CPMP/QWP/419/03. The European Agency for the Evaluation of Medicinal Products, Evaluation of Medicines for Human Use, London, U.K. (10 pages).
Gennaro, Alfonso R., Editor, "Pharmaceutical Sciences", MACK Publishing Company, Easton Pennsylvania, 1990, 5 pages.
Huang et al. "Rapid Screening of Antioxidants in Pharmaceutical Formulation Development Using Cyclic Voltammetry—Potential and Limitations," Current Drug Discovery Technologies, 2004, vol. 1, pp. 173-179 (2004).
International Search Report and Written Opinion for Application No. PCT/US2014/045581, dated Oct. 8, 2014, 8 pages.
IUPAC Commission on Nomenclature of Organic Chemistry, "Rules for the Nomenclature of Organic Chemistry, Section E: Stereochemistry (Recommendations 1974)," IUPAC Pure and Applied Chemistry, 1976, vol. 45, pp. 13-30.
IUPAC "Handbook of Pharmaceutical Salts: Properties, Selection, and Use," Table of Contents, 2002, Stahl and Wermuth Editors, Wiley-VCH, Weinheim, Germany, 5 pages.
Jenkins et al., "Introduction to X-Ray Powder Diffractometry," Chemical Analysis, vol. 138, 1996, J.D. Winefordner, Editor, John Wiley & Sons, 13 pages.
Kohan et al., "Addition of Atrasentan to Renin-Angiotensin System Blockade Reduces Albuminuria in Diabetic Nephropathy," J Am Soc Nephrol, 2011, vol. 22, No. 4, pp. 763-722.
Lavoie et al., "Antiperoxide Activity Of Sodium Metabisulfite, A Double-Edged Sword," Biochemical Pharmacology, 1994, vol. 47, No. 5, pp. 871-876.
Raichlin et al., "Efficacy and Safety of Atrasentan in Patients with Cardiovascular Risk and Early Atherosclerosis," Hypertension, 2008, vol. 52, No. 3, pp. 522-528.
Rowe et al., Editors "Handbook of Pharmaceutical Excipients," 7th Edition, Pharmaceutical Press, 2012, 7 pages.
Tirzitis et al., "Determination of antiradical and antioxidants activity: basic principles and new insights," Acta Biochimica Polonica, 2010, vol. 57, No. 1, pp. 139-142.
USPC, "Crospovidone," The United States Pharmacopeial Convention, Stage 6 Harmonization, Dec. 1, 2011, 2 pages.
USPC, "<711> Dissolution," The United States Pharmacopeial Convention, Stage 6 Harmonization, Dec. 1, 2011, 8 pages.
Wanasundara et al., "Antioxidants: Science Technology, and Applications," Ch. 11, pp. 431-489, Bailey's Industrial Oil and Fat Products, Sixth Ed., Six Volume Set., 2005, John Wiley & Sons, Inc.
Waterman et al., "Stabilization of Pharmaceuticals to Oxidative Degradation," Pharmaceutical Development and Technology, 2002, vol. 7, No. 1, pp. 1-32.
Webster et al., "Selection of Pharmaceutical Antioxidants by Hydrodynamic Voltammetry," Electroanalysis, 2012, vol. 24, No. 6, pp. 1394-1400.
Yoon et al., "Long-term endothelin receptor antagonism attenuates coronary plaque progression in patients with early atherosclerosis," International Journal of Cardiology (2012), http://dx.doi.org/10.1016/j.ijcard.2012.12.001.
Zonnenberg et al., "Phase I Dose-Escalation Study of the Safety and Pharmacokinetics of Atrasentan: An Endothelin Receptor Antagonist for Refractory Prostate Cancer," Clinical Cancer Research, Aug. 1, 2003, vol. 9, No. 8, pp. 2965-2972.

\* cited by examiner

STABILIZED PHARMACEUTICAL DOSAGE FORMS COMPRISING ATRASENTAN

CROSS-REFERENCE TO RELATED APPLICATION

This application is a continuation of U.S. Non-provisional application Ser. No. 14/324,603 filed Jul. 7, 2014, and claims priority to U.S. Provisional Application No. 61/843,799 filed Jul. 8, 2013, both of which are incorporated herein by reference in its entirety.

FIELD OF THE INVENTION

The present disclosure relates to: (a) methods of using stabilized pharmaceutical dosage forms comprising atrasentan, or a pharmaceutically acceptable salt thereof, and, optionally, another therapeutic agent to treat type 2 diabetes, microalbuminuria or macroalbuminuria; and (b) methods for the preparation of such pharmaceutical dosage forms.

BACKGROUND OF THE INVENTION

Atrasentan is a potent and selective antagonist for the endothelin A ($ET_A$) receptor. It previously was evaluated in clinical trials for the treatment of prostate cancer at daily doses ranging from 2.5 mg to at least 95 mg. Lower daily doses of atrasentan currently are being evaluated in clinical trials for the treatment of chronic kidney disease associated with Type II diabetes. Although the proprietary atrasentan pharmaceutical dosage forms most recently employed in these clinical trials were suitable for such clinical trials, they did not exhibit the longer-term stability profile needed for a commercial drug product. Accordingly, there is a need for atrasentan pharmaceutical dosage forms having improved stability profiles that comply with regulatory requirements and are suitable for commercial use.

SUMMARY OF THE INVENTION

The present disclosure relates to a method of treating type 2 diabetes, microalbuminuria or macroalbuminuria. The method comprises administering daily to a human subject a dosage form comprising:

(a) about 0.25 mg to about 1.25 mg of atrasentan, or an equivalent amount of a pharmaceutically acceptable salt thereof; wherein the weight percent of atrasentan, or pharmaceutically acceptable salt thereof, in the dosage form is from about 0.05 weight percent to about 2.0 weight percent on an atrasentan free base equivalent weight basis;

(b) a pharmaceutically acceptable anti-oxidant; wherein the molar ratio of the anti-oxidant to atrasentan, or pharmaceutically acceptable salt thereof, is from about 10:1 to about 1:10; and (c) a pharmaceutically acceptable diluent, wherein the human subject is susceptible to, or is suffering from, type 2 diabetes, microalbuminuria or macroalbuminuria.

The present disclosure relates to a method of preparing a stable pharmaceutical dosage form. The method comprises:

(a) combining atrasentan, or a pharmaceutically acceptable salt thereof, with a pharmaceutically acceptable polymeric binder to form a first mixture;

(b) blending the first mixture with a pharmaceutically acceptable diluent and a pharmaceutically acceptable anti-oxidant to form a second mixture; and (c) encapsulating or tableting the second mixture to yield the dosage form, wherein the molar ratio of the anti-oxidant to atrasentan, or pharmaceutically acceptable salt thereof, is from about 10:1 to about 1:10.

DETAILED DESCRIPTION OF THE INVENTION

I. Definitions

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "about" generally refers to a range of numbers that one of skill in the art would consider equivalent to the recited value (i.e., having the same function or result). In many instances, the term "about" may include numbers that are rounded to the nearest significant figure."

The term "atrasentan" refers to the compound (2R,3R,4S)-4-(1,3-benzodioxol-5-yl)-1-[2-(dibutylamino)-2-oxo-ethyl]-2-(4-methoxyphenyl)pyrrolidine-3-carboxylic acid which has the structure shown below:

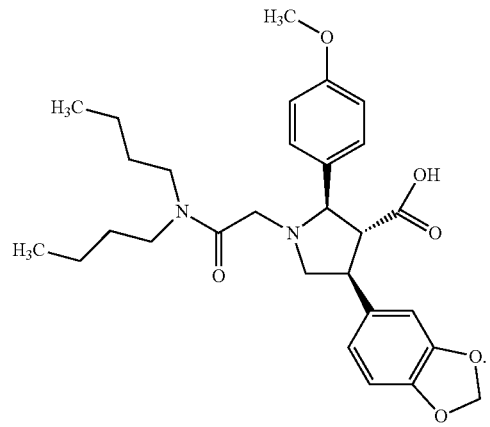 [SMILES: CCCCN(CCCC)C(=O)CN1C[C@H](c2ccc3c(c2)OCO3)[C@@H](C(=O)O)[C@@H]1c1ccc(OC)cc1]

The term "atrasentan, or a pharmaceutically acceptable salt thereof" as used throughout this disclosure is intended to encompass the free base form of the compound shown above as well as any pharmaceutically acceptable salt of the compound, such as a hydrochloride salt. Unless otherwise stated, any reference to an amount of atrasentan in this disclosure is based on the free base equivalent weight of atrasentan. For example, 0.75 mg of atrasentan refers to 0.75 mg of atrasentan in the free base form or an equivalent amount of a salt form of atrasentan. Methods for making atrasentan are described, for example, in U.S. Pat. Nos. 5,731,434; 5,622,971; 5,767,144; 6,162,927; 6,380,241; 6,462,194; 6,946,481; 7,208,517; and 7,365,093. The contents of these patents are incorporated by reference in this application.

Unless the context requires otherwise, the terms "comprise," "comprises," and "comprising" are used on the basis and clear understanding that they are to be interpreted inclusively, rather than exclusively, and that Applicants intend each of those words to be so interpreted in construing this patent, including the claims below.

The term "pharmaceutically acceptable" (such as in the recitation of a "pharmaceutically acceptable salt" or a "pharmaceutically acceptable diluent") refers to a material that is compatible with administration to a subject, e.g., the material does not cause an undesirable biological effect. Examples of pharmaceutically acceptable salts are described in "Handbook of Pharmaceutical Salts: Properties, Selection, and Use" by Stahl and Wermuth (Wiley-VCH, Weinheim, Germany, 2002). Examples of pharmaceutically acceptable excipients are described in the "Handbook of Pharmaceutical Excipients," Rowe et al., Ed. (Pharmaceutical Press, 7$^{th}$ Ed., 2012).

The term "subject" refers to an animal. In one aspect, the animal is a mammal, including a human or non-human, preferably a human subject.

The terms "treating" and "treatment" refer to ameliorating, suppressing, eradicating, reducing the severity of, decreasing the frequency of incidence of, preventing, reducing the risk of, or delaying the onset of the condition.

The abbreviation "HDPE" refers to high-density polyethylene.

The abbreviation "HPMC" refers to hydroxypropyl methylcellulose.

The abbreviation "UACR" refers to urinary-albumin-to-creatine ratio.

II. Stabilized Solid Dosage Forms

The present disclosure relates to stable solid pharmaceutical dosage forms comprising atrasentan, or a pharmaceutically acceptable salt thereof. Among the challenges in developing such dosage forms are the low atrasentan dose required for the dosage form, the narrow therapeutic window for treating patients, the inherent chemical instability of atrasentan in the presence of moisture and many common excipients, and the safe handling requirements due to the potency of atrasentan. The stabilized solid dosage forms of the present disclosure, however, overcome such challenges and allow for the use of a broader range of excipients (e.g., metal-ion containing excipients such as magnesium stearate), packaging configurations (e.g., blister packs), and manufacturing conditions (e.g., wet granulation).

The low dosing and the narrow therapeutic window for atrasentan have been confirmed through analysis of the data collected from recent Phase IIb clinical trials in subjects with diabetic nephropathy. These Phase IIb clinical trials evaluated the safety and efficacy of atrasentan to identify an appropriate balance between the systemic effects of atrasentan (which can lead to adverse side effects such as edema) and the efficacy effects of atrasentan. Analysis of the clinical data resulted in a finding that for the subjects tested a daily dose of atrasentan less than about 0.25 mg generally was sub-therapeutic while a daily dose greater than about 1.25 mg generally resulted in an increase in adverse effects, particularly peripheral edema, without any further improvement in efficacy relative to the 1.25 mg daily dose. Within this narrow therapeutic window (about 0.25 mg to about 1.25 mg daily), atrasentan was found to significantly reduce residual albuminuria and the urinary-albumin-to-creatine ratio in the subjects studied. Reduction of residual albuminuria and the urinary-albumin-to-creatine ratio are surrogate endpoints generally associated with delaying the progression of end-stage renal disease and associated cardiovascular complications.

As noted above, atrasentan will degrade in the presence of many common excipients. It is believed that hydrolysis, particularly acid-catalyzed hydrolysis, and oxidation are the primary degradation pathways for atrasentan in low-dose, non-stabilized solid dosage forms. It is further believed that the primary degradation products of atrasentan in low-dose, non-stabilized solid dosage forms are the diol, pyrrolidine acid, and N-oxide shown below:

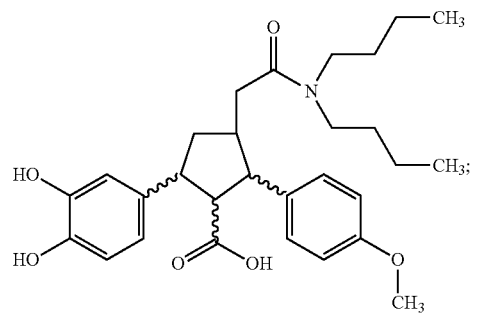

Diol

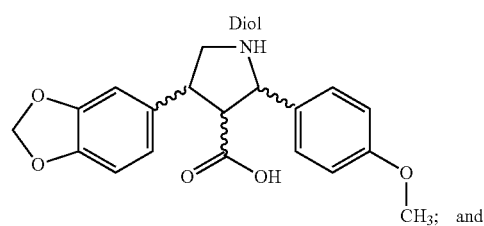

Pyrrolidine Acid

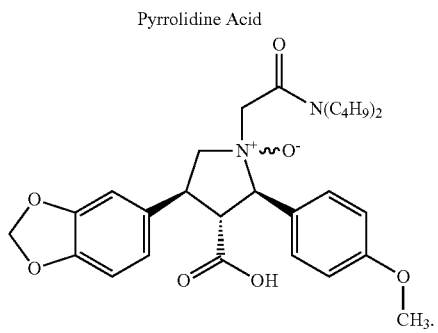

N-Oxide

The diol and pyrrolidine acid are believed to form through acid-catalyzed hydrolysis while the N-oxide is believed to form through an oxidative mechanism. Degradation of atrasentan generally is exacerbated as acidity, moisture content, and metal ion content (such as $Na^+$, $Mg^{2+}$, and $Ca^{2+}$) increase in the dosage form or in the specific components of the dosage form. The incompatibility of atrasentan with metal ions is believed to be due to the metal ions catalyzing an oxidation reaction and/or forming a complex with atrasentan.

The low dosing, potent nature, and chemical instability of atrasentan further increase the difficulty of developing a suitable process for the preparation of the dosage form. A suitable process generally will ensure, inter alia, that atrasentan can be safely handled during the preparation of the dosage form and that dose-to-dose content uniformity can be maintained. One potential approach is to dissolve or disperse the atrasentan in a liquid vehicle (such as water) during processing to minimize the generation of airborne dust and the associated risk of operator exposure to the drug. Dissolving or dispersing the atrasentan in a liquid vehicle during processing also can assist with maintaining suitable dose-to-dose content uniformity for the dosage form. The chemical instability of atrasentan in the presence of water coupled with the decreased chemical stability normally associated with solution state chemistry, however, raises potential concerns that use of a process employing a liquid vehicle to prepare the atrasentan dosage form (such as a process comprising a wet granulation step in which atrasentan is wet granulated with the other excipients during the preparation of the dosage form) may not result in an acceptable final dosage form.

Applicants have discovered stable solid pharmaceutical dosage forms comprising atrasentan, or a pharmaceutically acceptable salt thereof, that overcome these challenges. In general, the dosage forms comprise a stabilizing amount of an anti-oxidant; a stabilizing amount of a polymeric binder; or a first amount of an anti-oxidant and a second amount of a polymeric binder wherein the first amount and the second amount together provide a stabilizing effect. In one aspect, the dosage form comprises a stabilizing amount of L-cysteine, or a pharmaceutically acceptable salt or ester thereof. In another aspect, the dosage form comprises a stabilizing amount of a polymeric binder selected from the group consisting of hydroxymethylpropylcellulose, hydroxyethylpropylcellulose, and hydroxypropylellulose. In another aspect, the dosage form comprises a stabilizing amount of hydroxymethylpropylcellulose. In another aspect, the dosage form comprises a first amount of L-cysteine, or a pharmaceutically acceptable salt or ester thereof; a second amount of a polymeric binder selected from the group consisting of hydroxymethylpropylcellulose, hydroxyethylpropylcellulose, and hydroxypropylellulose; and the first amount and the second amount together provide a stabilizing effect. In another aspect, the dosage form comprises a first amount of L-cysteine, or a pharmaceutically acceptable salt or ester thereof; a second amount of a hydroxymethylpropylcellulose; and the first amount and the second amount together provide a stabilizing effect. In further aspects, the process for preparing the dosage form comprises a wet granulation step wherein a liquid mixture comprising the atrasentan, or a pharmaceutically acceptable salt thereof, and the polymeric binder is prepared and used as a granulating agent during the wet granulation step.

A. Dosage Forms Comprising an Anti-Oxidant

In one embodiment, the disclosure relates to a stable solid pharmaceutical dosage form comprising:

(a) about 0.25 mg to about 1.25 mg of atrasentan, or an equivalent amount of a pharmaceutically acceptable salt thereof; wherein the weight percent of atrasentan, or pharmaceutically acceptable salt thereof, in the dosage form is from about 0.05 weight percent to about 2.0 weight percent on an atrasentan free base equivalent weight basis;

(b) a pharmaceutically acceptable anti-oxidant; wherein the molar ratio of the anti-oxidant to atrasentan, or pharmaceutically acceptable salt thereof, is from about 10:1 to about 1:10; and (c) a pharmaceutically acceptable diluent;

wherein degradation of atrasentan in the dosage form is less than degradation of atrasentan in an otherwise identical dosage form lacking the anti-oxidant when the dosage forms are stored for a storage period of six months at about 40° C. and about 75% relative humidity.

In one embodiment, the dosage form is stored during the storage period in a semi-permeable container or a substantially impermeable container. In one aspect, the dosage form is stored during the storage period in a sealed HDPE bottle or a blister package. In another aspect, the dosage form is stored during the storage period in a sealed HDPE bottle. In another aspect, the dosage form is stored during the storage period in a blister package.

(i) Atrasentan

The dosage form can comprise a free base of atrasentan, a pharmaceutically acceptable salt of atrasentan, or a combination thereof. In one aspect, the dosage form comprises a free base of atrasentan. In another aspect, the dosage form comprises a pharmaceutically acceptable salt of atrasentan. In another aspect, the dosage form comprises a hydrochloride salt of atrasentan.

In one embodiment, the weight percent of atrasentan, or pharmaceutically acceptable salt thereof, in the dosage form is from about 0.1 weight percent to about 2.0 weight percent on an atrasentan free base equivalent weight basis. In one aspect, the weight percent of atrasentan, or pharmaceutically acceptable salt thereof, in the dosage form is from about 0.2 weight percent to about 1.0 weight percent on an atrasentan free base equivalent weight basis. In another aspect, the weight percent of atrasentan, or pharmaceutically acceptable salt thereof, in the dosage form is from about 0.3 weight percent to about 0.8 weight percent on an atrasentan free base equivalent weight basis. In another aspect, the weight percent of atrasentan, or pharmaceutically acceptable salt thereof, in the dosage form is from about 0.40 weight percent to about 0.45 weight percent on an atrasentan free base equivalent weight basis. In another aspect, the weight percent of atrasentan, or pharmaceutically acceptable salt thereof, in the dosage form is from about 0.60 weight percent to about 0.65 weight percent on an atrasentan free base equivalent weight basis.

In another embodiment, the dosage form comprises from about 0.40 mg to about 1.00 mg of atrasentan, or an equivalent amount of a pharmaceutically acceptable salt thereof. In one aspect, the dosage form comprises from about 0.40 mg to about 0.85 mg of atrasentan, or an equivalent amount of a pharmaceutically acceptable salt thereof. In another aspect, the dosage form comprises about 0.50 mg of atrasentan, or an equivalent amount of a pharmaceutically acceptable salt thereof. In another aspect, the dosage form comprises about 0.75 mg of atrasentan, or an equivalent amount of a pharmaceutically acceptable salt thereof.

In another embodiment, the dosage form comprises atrasentan hydrochloride. In one aspect, the dosage form comprises atrasentan hydrochloride having a solid-state form selected from the group consisting of amorphous atrasentan hydrochloride, atrasentan hydrochloride Form I, atrasentan hydrochloride Form II, and atrasentan hydrochloride Form III. In another aspect, the dosage form comprises amorphous atrasentan hydrochloride. The properties and preparation of amorphous atrasentan hydrochloride are discussed in greater detail in WO 2006/034085. In another aspect, the dosage form comprises atrasentan hydrochloride Form I. The properties and preparation of atrasentan hydrochloride Form I are discussed in greater detail in WO 2006/034094. In another aspect, the dosage form comprises atrasentan hydrochloride Form II. The properties and preparation of atrasentan hydrochloride Form II are discussed in greater detail in WO 2006/034084. In another aspect, the dosage form comprises atrasentan hydrochloride Form III. The properties and preparation of atrasentan hydrochloride Form III are discussed in greater detail in WO 2006/034234. The contents of these patent applications are incorporated by reference in this application.

(ii) Anti-Oxidant

Suitable anti-oxidants for use in the disclosed dosage forms include anti-oxidants that function as reducing agents and are oxidized to pharmaceutically acceptable reduced products in the dosage form. In one embodiment, the anti-oxidant has an oxidation reduction potential less than the oxidation reduction potential of atrasentan (i.e., an oxidation reduction potential less than about 900 mV) and greater than about 550 mV. In one aspect, the anti-oxidant has an oxidation reduction potential less than about 550 mV. In another aspect, the anti-oxidant has an oxidation reduction potential from about 1 mV to about 550 mV. In another aspect, the solubility of the anti-oxidant in water at about 25° C. is greater than about 24 mg/mL. In another aspect, the anti-oxidant is an amino acid, or a pharmaceutically acceptable salt or ester thereof. In another aspect, the anti-oxidant is L-cysteine, or a pharmaceutically acceptable salt or ester thereof. In another aspect, the anti-oxidant is selected from the group consisting of L-cysteine hydrochloride monohydrate, L-cysteine hydrochloride anhydrate, and L-cysteine ethyl ester. In another aspect, the dosage form comprises L-cysteine hydrochloride monohydrate.

In another embodiment, the weight percent of the anti-oxidant in the dosage form is from about 0.05 weight percent to about 1.0 weight percent. In one aspect, the weight percent of the anti-oxidant in the dosage form is from about 0.07 weight percent to about 0.7 weight percent. In another aspect, the weight percent of the anti-oxidant in the dosage form is from about 0.09 weight percent to about 0.5 weight percent.

In another embodiment, the molar ratio of the anti-oxidant to atrasentan, or pharmaceutically acceptable salt thereof, is from about 10:1 to about 1:10. In one aspect, the molar ratio of the anti-oxidant to atrasentan, or pharmaceutically acceptable salt thereof, in the dosage form is from about 5:1 to about 1:5. In another aspect, the molar ratio of the anti-oxidant to atrasentan, or pharmaceutically acceptable salt thereof, is from about 2:1 to about 1:2. In another aspect, the molar ratio of the anti-oxidant to atrasentan, or pharmaceutically acceptable salt thereof, is about 1:1.

(iii) Diluent

Suitable diluents for use in the disclosed dosage forms include, but are not limited to, lactose (such as lactose monohydrate, lactose anhydrous, and PHARMATOSE® DCL21), sucrose, glucose, mannitol, sorbitol, isomalt, microcrystalline cellulose (such as AVICEL® PH101 and AVICEL® PH102), silicified microcrystalline cellulose (such as PROSOLV® SMCC 50 and SMCC 90), dicalcium phosphate, starches, and combinations thereof. In one aspect, the diluent is selected from the group consisting of lactose, mannitol, isomalt, microcrystalline cellulose, dicalcium phosphate, and combinations thereof. In another aspect, the diluent is lactose.

In one embodiment, the weight percent of the diluent in the dosage form is from about 70 weight percent to about 99 weight percent. In one aspect, the weight percent of the diluent in the dosage form is from about 80 weight percent to about 99 weight percent. In another aspect, the weight percent of the diluent in the dosage form is from about 85 weight percent to about 99 weight percent.

(iv) Binder

In one embodiment, the dosage form further comprises a pharmaceutically acceptable binder. Suitable binders for use in the disclosed dosage forms include, but are not limited to, celluloses, such as hydroxypropyl methylcellulose (e.g., Hypromellose E5 (Premium LV)), hydroxypropyl ethylcellulose, and hydroxypropyl cellulose, and other pharmaceutically acceptable substances with cohesive properties. In one aspect, the binder is selected from the group consisting of hydroxymethylpropylcellulose, hydroxyethylpropylcellulose, and hydroxypropylcellulose. In another aspect, the binder is hydroxypropyl methylcellulose. In another aspect, the binder is hydroxypropylcellulose. In another aspect, the binder is hydroxyethylpropylcellulose.

In another embodiment, the dosage form further comprises a pharmaceutically acceptable binder and the weight percent of the binder in the dosage form is from about 1.0 weight percent to about 10.0 weight percent. In one aspect, the weight percent of the binder in the dosage form is from about 1.0 weight percent to about 8.0 weight percent. In another aspect, the weight percent of the binder in the dosage form is from about 1.0 weight percent to about 5.0 weight percent.

In another embodiment, the dosage form further comprises a pharmaceutically acceptable binder and the weight to weight ratio of the binder to atrasentan, or pharmaceutically acceptable salt thereof, is from about 2:1 to about 25:1 on an atrasentan free base equivalent weight basis. In one aspect, the weight to weight ratio of the binder to the atrasentan, or pharmaceutically acceptable salt thereof, is from about 1:1 to about 20:1 on an atrasentan free base equivalent weight basis. In another aspect, the weight to weight ratio of the binder to the atrasentan, or pharmaceutically acceptable salt thereof, is from about 1:1 to about 15:1 on an atrasentan free base equivalent weight basis.

(v) Disintegrant

In another embodiment, the dosage form optionally comprises a pharmaceutically acceptable disintegrant. Suitable disintegrants for use in the disclosed dosage forms include, but are not limited to, cross-linked polyvinyl pyrrolidone (such as POLYPLASDONE™ XL), corn starch, potato starch, maize starch and modified starches (including sodium starch glycolate), agar-agar, alginic acids, microcrystalline cellulose, sodium croscarmellose, and combinations thereof. In one aspect, the disintegrant is selected from the group consisting of crospovidone, sodium starch glycolate, and sodium croscarmellose. In another aspect, the disintegrant is a cross-linked polyvinyl pyrrolidone. In another aspect, the disintegrant is crospovidone.

In another embodiment, the dosage form further comprises a pharmaceutically acceptable disintegrant and the weight percent of the disintegrant in the dosage form is from about 1.0 weight percent to about 10.0 weight percent. In one aspect, the weight percent of the disintegrant in the dosage form is from about 1.0 weight percent to about 6.0 weight percent. In another aspect, the weight percent of the disintegrant in the dosage form is from about 1.0 weight percent to about 4.0 weight percent.

In another embodiment, the dosage form further comprises a pharmaceutically acceptable disintegrant and the weight to weight ratio of the disintegrant to the anti-oxidant is from about 60:1 to about 3:1. In one aspect, the weight to weight ratio of the disintegrant to the anti-oxidant is from about 50:1 to about 4:1. In another aspect, the weight to weight ratio of the disintegrant to the anti-oxidant is from about 35:1 to about 5:1.

(vi) Additional Excipients

In further embodiments, the dosage form optionally comprises a pharmaceutically acceptable lubricant and/or glidant. Suitable lubricants and glidants for use in the disclosed dosage forms include, but are not limited to, silicon dioxide (such as SYLOID® 244FP and AEROSIL® 200), glyceryl behenate (such as COMPRITOL®), talc, stearic acid, solid polyethylene glycols, silica gel and mixtures thereof and other substances with lubricating or gliding properties. In one aspect, the lubricant is glyceryl behenate (such as COMPRITOL®). In another aspect, the glidant is silicon dioxide (such as SYLOID® 244FP). In another aspect, the lubricant is glyceryl behenate and the glidant is silicon dioxide.

In another embodiment, the dosage form further comprises a pharmaceutically acceptable glidant. In one aspect, the weight percent of the glidant in the dosage form is from about 0.1 weight percent to about 1.5 weight percent. In another aspect, the weight percent of the glidant in the dosage form is from about 0.1 weight percent to about 1.0 weight percent. In another aspect, the weight percent of the glidant in the dosage form is from about 0.1 weight percent to about 0.8 weight percent.

In another embodiment, the dosage form further comprises a pharmaceutically acceptable lubricant. In one aspect, the dosage form further comprises a pharmaceutically acceptable, hydrophobic lubricant. In another aspect, the weight percent of the lubricant in the dosage form is from about 0.05 weight percent to about 5.0 weight percent. In another aspect, the weight percent of the lubricant in the dosage form is from about 0.2 weight percent to about 3.0 weight percent. In another aspect, the weight percent of the lubricant in the dosage form is from about 0.5 weight percent to about 2.0 weight percent.

In another embodiment, the dosage form further comprises a disintegrant, a glidant, and a lubricant.

(vii) Additional Embodiments

In one embodiment, the molar ratio of the anti-oxidant to atrasentan, or pharmaceutically acceptable salt thereof, is from about 5:1 to about 1:5; and the weight to weight ratio of the binder to atrasentan, or pharmaceutically acceptable salt thereof, is from about 1:1 to about 20:1 on an atrasentan free base equivalent weight basis. In one aspect, this dosage form further comprises a disintegrant and the weight to weight ratio of the disintegrant to the anti-oxidant is from about 60:1 to about 3:1. In another aspect, this dosage form comprises from about 0.40 mg to about 0.85 mg of atrasentan, or an equivalent amount of a pharmaceutically acceptable salt thereof.

In another embodiment, the molar ratio of the anti-oxidant to atrasentan, or pharmaceutically acceptable salt thereof, is from about 2:1 to about 1:2; and the weight to weight ratio of the binder to atrasentan, or pharmaceutically acceptable salt thereof, is from about 1:1 to about 15:1 on an atrasentan free base equivalent weight basis. In one aspect, the dosage form further comprises a disintegrant and the weight to weight ratio of the disintegrant to the anti-oxidant is from about 50:1 to about 4:1. In another aspect, the weight percent of atrasentan, or pharmaceutically acceptable salt thereof, in this dosage form is from about 0.2 weight percent to about 1.0 weight percent on an atrasentan free base equivalent weight basis. In another aspect, this dosage form comprises from about 0.40 mg to about 0.85 mg of atrasentan, or an equivalent amount of a pharmaceutically acceptable salt thereof.

In another embodiment, the molar ratio of the anti-oxidant to atrasentan, or pharmaceutically acceptable salt thereof, is about 1:1; and the weight to weight ratio of the binder to atrasentan, or pharmaceutically acceptable salt thereof, is from about 1:1 to about 15:1 on an atrasentan free base equivalent weight basis. In one aspect, this dosage form further comprises a disintegrant and the weight to weight ratio of the disintegrant to the anti-oxidant is from about 35:1 to about 5:1. In another aspect, the weight percent of atrasentan, or pharmaceutically acceptable salt thereof, in this dosage form is from about 0.3 weight percent to about 0.8 weight percent on an atrasentan free base equivalent weight basis. In another aspect, this dosage form comprises from about 0.40 mg to about 0.85 mg of atrasentan, or an equivalent amount of a pharmaceutically acceptable salt thereof.

In another embodiment, the dosage form comprises from about 0.05 weight percent to about 1.0 weight percent of the anti-oxidant; and from about 1.0 weight percent to about 10.0 weight percent of the binder. In one aspect, this dosage form further comprises a disintegrant and the weight percent of the disintegrant in the dosage form is from about 1.0 weight percent to about 10.0 weight percent. In another aspect, the weight percent of atrasentan, or pharmaceutically acceptable salt thereof, in this dosage form is from about 0.1 weight percent to about 2.0 weight percent on an atrasentan free base equivalent weight basis. In another aspect, this dosage form comprises from about 0.40 mg to about 0.85 mg of atrasentan, or an equivalent amount of a pharmaceutically acceptable salt thereof.

In another embodiment, the dosage form comprises from about 0.07 weight percent to about 0.70 weight percent of the anti-oxidant; and from about 1.0 weight percent to about 8.0 weight percent of the binder. In one aspect, this dosage form further comprises a disintegrant and the weight percent of the disintegrant in the dosage form is from about 1.0 weight percent to about 6.0 weight percent. In another aspect, the weight percent of atrasentan, or pharmaceutically acceptable salt thereof, in this dosage form is from about 0.2 weight percent to about 1.0 weight percent on an atrasentan free base equivalent weight basis. In another aspect, this dosage form comprises from about 0.40 mg to about 0.85 mg of atrasentan, or an equivalent amount of a pharmaceutically acceptable salt thereof.

In another embodiment, the dosage form comprises from about 0.09 weight percent to about 0.80 weight percent of the anti-oxidant; and from about 1.0 weight percent to about 5.0 weight percent of the binder. In one aspect, this dosage form further comprises a disintegrant and the weight percent of the disintegrant in the dosage form is from about 1.0 weight percent to about 4.0 weight percent. In another aspect, the weight percent of atrasentan, or pharmaceutically acceptable salt thereof, in this dosage form is from about 0.3 weight percent to about 0.8 weight percent on an atrasentan free base equivalent weight basis. In another aspect, this dosage form comprises from about 0.40 mg to about 0.85 mg of atrasentan, or an equivalent amount of a pharmaceutically acceptable salt thereof.

In another embodiment, the dosage form comprises:

(a) about 0.1 weight percent to about 2.0 weight percent of atrasentan, or pharmaceutically acceptable salt thereof, on an atrasentan free base equivalent weight basis;

(b) about 0.05 weight percent to about 1.0 weight percent of the anti-oxidant;

(c) about 75 weight percent to about 99 weight percent of the diluent;

(d) about 1.0 weight percent to about 10.0 weight percent of a pharmaceutically acceptable binder;

(e) optionally, about 1.0 weight percent to about 10.0 weight percent of a pharmaceutically acceptable disintegrant;

(f) optionally, about 0 weight percent to about 1.5 weight percent of a pharmaceutically acceptable glidant; and (g) optionally, about 0 weight percent to about 5.0 weight percent of a pharmaceutically acceptable lubricant;

wherein the cumulative weight percent for all components of the dosage form equals 100 percent.

In another embodiment, the dosage form comprises:

(a) about 0.1 weight percent to about 2.0 weight percent of atrasentan, or pharmaceutically acceptable salt thereof, on an atrasentan free base equivalent weight basis;

(b) about 0.05 weight percent to about 1.0 weight percent of the anti-oxidant;

(c) about 75 weight percent to about 99 weight percent of the diluent;

(d) about 1.0 weight percent to about 10.0 weight percent of a pharmaceutically acceptable binder;

(e) about 1.0 weight percent to about 10.0 weight percent of a pharmaceutically acceptable disintegrant;

(f) optionally, about 0 weight percent to about 1.5 weight percent of a pharmaceutically acceptable glidant; and (g) optionally, about 0 weight percent to about 5.0 weight percent of a pharmaceutically acceptable lubricant;

wherein the cumulative weight percent for all components of the dosage form equals 100 percent.

In another embodiment, the dosage form comprises:

(a) about 0.2 weight percent to about 1.0 weight percent of atrasentan, or pharmaceutically acceptable salt thereof, on an atrasentan free base equivalent weight basis;

(b) about 0.07 weight percent to about 0.7 weight percent of the anti-oxidant;

(c) about 82 weight percent to about 99 weight percent of the diluent;

(d) about 1.0 weight percent to about 8.0 weight percent of a pharmaceutically acceptable binder;

(e) optionally, about 1.0 weight percent to about 6.0 weight percent of a pharmaceutically acceptable disintegrant;

(f) optionally, about 0 weight percent to about 1.0 weight percent of a pharmaceutically acceptable glidant; and (g) optionally, about 0 weight percent to about 3.0 weight percent of a pharmaceutically acceptable lubricant;

wherein the cumulative weight percent for all components of the dosage form equals 100 percent.

In another embodiment, the dosage form comprises:

(a) about 0.2 weight percent to about 1.0 weight percent of atrasentan, or pharmaceutically acceptable salt thereof, on an atrasentan free base equivalent weight basis;

(b) about 0.07 weight percent to about 0.7 weight percent of the anti-oxidant;

(c) about 82 weight percent to about 99 weight percent of the diluent;

(d) about 1.0 weight percent to about 8.0 weight percent of a pharmaceutically acceptable binder;

(e) about 1.0 weight percent to about 6.0 weight percent of a pharmaceutically acceptable disintegrant;

(f) optionally, about 0 weight percent to about 1.0 weight percent of a pharmaceutically acceptable glidant; and (g) optionally, about 0 weight percent to about 3.0 weight percent of a pharmaceutically acceptable lubricant;

wherein the cumulative weight percent for all components of the dosage form equals 100 percent.

In another embodiment, the dosage form comprises:

(a) about 0.3 weight percent to about 0.8 weight percent of atrasentan, or pharmaceutically acceptable salt thereof, on an atrasentan free base equivalent weight basis;

(b) about 0.09 weight percent to about 0.5 weight percent of the anti-oxidant;

(c) about 87 weight percent to about 99 weight percent of a pharmaceutically acceptable diluent;

(d) about 1.0 weight percent to about 5.0 weight percent of a pharmaceutically acceptable binder;

(e) optionally, about 1.0 weight percent to about 4.0 weight percent of a pharmaceutically acceptable disintegrant;

(f) optionally, about 0 weight percent to about 0.75 weight percent of a pharmaceutically acceptable glidant; and (g) optionally, about 0 weight percent to about 2.0 weight percent of a pharmaceutically acceptable lubricant;

wherein the cumulative weight percent for all components of the dosage form equals 100 percent.

In another embodiment, the dosage form comprises:

(a) about 0.3 weight percent to about 0.8 weight percent of atrasentan, or pharmaceutically acceptable salt thereof, on an atrasentan free base equivalent weight basis;

(b) about 0.09 weight percent to about 0.5 weight percent of the anti-oxidant;

(c) about 87 weight percent to about 99 weight percent of a pharmaceutically acceptable diluent;

(d) about 1.0 weight percent to about 5.0 weight percent of a pharmaceutically acceptable binder;

(e) about 1.0 weight percent to about 4.0 weight percent of a pharmaceutically acceptable disintegrant;

(f) optionally, about 0 weight percent to about 0.75 weight percent of a pharmaceutically acceptable glidant; and (g) optionally, about 0 weight percent to about 2.0 weight percent of a pharmaceutically acceptable lubricant;

wherein the cumulative weight percent for all components of the dosage form equals 100 percent.

In another embodiment, the dosage form is a tablet. In one aspect, the tablet has a weight from about 37.5 mg to about 1500 mg. In another aspect, the tablet has a weight from about 50 mg to about 750 mg. In another aspect, the tablet has a weight from about 50 mg to about 250 mg. In another aspect, the tablet has a weight from about 75 mg to about 500 mg. In another aspect, the tablet has a weight from about 75 mg to about 150 mg. In another aspect, the tablet has a weight from about 100 mg to about 250 mg. In another aspect, the tablet has a weight from about 100 mg to about 230 mg.

In general, the tablet optionally can be surrounded or coated with at least one non-rate-controlling layer. The non-rate-controlling layer can be formed as a single layer, coating or membrane or a plurality of single layers, coatings or membranes. The functions of the non-rate-controlling layer can include, for example, providing further stability for the atrasentan, serving as a process aid and/or as a cosmetic enhancement for the formulation, and/or acting as a masking agent to reduce any undesired odor associated with the formulation.

When the dosage form comprises a non-rate-controlling layer, the non-rate-controlling layer can be made of one or more polymers, as well as, other ingredients known in the art, such as, but not limited to, plasticizers, pigments/opacifiers, waxes, etc. Examples of polymers that can be used include, but are not limited to, hydroxypropyl methylcellulose, hydroxypropyl cellulose, methylcellulose, polyvinyl alcohol and polyethylene glycol. Examples of plasticizers that can be used include, but are not limited to, polyethylene glycol(s), glycerin, triacetin, triethyl citrate, diethyl phthalate, L-cysteine, and mineral oils. Examples of pigments/opacifiers that can be used include, but are not limited to, water soluble dyes (for example, sunset yellow, quinoline yellow, erythrosine, and tartrazine), pigments (for example, aluminum lakes, titanium oxides, iron oxides and talc), and natural products (for example, riboflavin, carotenoids, chlorophyll, anthocyanins, and carmine). An example of a wax that can be used includes, but is not limited to, a paraffin wax.

In another embodiment, the dosage form is a tablet coated with a pharmaceutically acceptable polymer.

In another embodiment, the dosage form is a capsule.

In another embodiment, the dosage form is packaged in a semi-permeable container. In one aspect, the semi-permeable container is a blister pack.

In another embodiment, the dosage form is packaged in a substantially impermeable container.

In another embodiment, the dosage form is an immediate release dosage form. In one aspect, the dosage form is an immediate release tablet and releases at least about 85% of the atrasentan, or pharmaceutically acceptable salt thereof, within about 45 minutes as determined in an in vitro dissolution test conducted using a USP Dissolution Apparatus 2 (Paddle Apparatus), a 0.01N hydrochloric acid dissolution medium, and a paddle rotation of 50 RPM. In another aspect, the dosage form is an immediate release tablet and releases at least about 75% of the atrasentan, or pharmaceutically acceptable salt thereof, within about 30 minutes.

In another embodiment, the dosage form comprises less than about 1.0 weight percent of total impurities resulting from degradation of the atrasentan, or pharmaceutically acceptable salt thereof, after a storage period of six months at about 40° C. and about 75% relative humidity. In one aspect, degradation of the atrasentan, or pharmaceutically acceptable salt thereof, is analyzed using high-performance liquid chromatography.

In another embodiment, the dosage form comprises less than about 0.6 weight percent of any single impurity resulting from degradation of the atrasentan, or pharmaceutically acceptable salt thereof, after a storage period of six months at about 40° C. and about 75% relative humidity. In one aspect, degradation of the atrasentan, or pharmaceutically acceptable salt thereof, is analyzed using high-performance liquid chromatography.

In another embodiment, the dosage form comprises less than about 1.0 weight percent of total impurities and less than about 0.6 weight percent of any single impurity resulting from degradation of the atrasentan, or pharmaceutically acceptable salt thereof, after a storage period of six months at about 40° C. and about 75% relative humidity. In one aspect, degradation of the atrasentan, or pharmaceutically acceptable salt thereof, is analyzed using high-performance liquid chromatography.

B. Dosage Forms Comprising L-Cysteine and/or Polymeric Binder

In one embodiment, the disclosure relates to a stable solid pharmaceutical dosage form comprising:

(a) about 0.25 mg to about 1.25 mg of atrasentan, or an equivalent amount of a pharmaceutically acceptable salt thereof; wherein the weight percent of atrasentan, or pharmaceutically acceptable salt thereof, in the dosage form is from about 0.05 weight percent to about 2.0 weight percent on an atrasentan free base equivalent weight basis;

(b) L-cysteine, or a pharmaceutically acceptable salt or ester thereof; wherein the molar ratio of the L-cysteine, or a pharmaceutically acceptable salt or ester thereof, to atrasentan, or pharmaceutically acceptable salt thereof, is from about 10:1 to about 1:10; and (c) a pharmaceutically acceptable diluent;

wherein degradation of atrasentan in the dosage form is less than degradation of atrasentan in an otherwise identical dosage form lacking the L-cysteine, or a pharmaceutically acceptable salt or ester thereof, when the dosage forms are stored for a storage period of six months at about 40° C. and about 75% relative humidity.

In another embodiment, the disclosure relates to a stable solid pharmaceutical dosage form comprising:

(a) about 0.25 mg to about 1.25 mg of atrasentan, or an equivalent amount of a pharmaceutically acceptable salt thereof; wherein the weight percent of atrasentan, or pharmaceutically acceptable salt thereof, in the dosage form is from about 0.05 weight percent to about 2.0 weight percent on an atrasentan free base equivalent weight basis;

(b) a pharmaceutically acceptable polymeric binder selected from the group consisting of hydroxymethylpropylcellulose, hydroxyethylpropylcellulose, and hydroxypropylcellulose; wherein the weight to weight ratio of the binder to atrasentan, or pharmaceutically acceptable salt thereof, is from about 2:1 to about 25:1 on an atrasentan free base equivalent weight basis; and (c) a pharmaceutically acceptable diluent;

wherein degradation of atrasentan in the dosage form is less than degradation of atrasentan in an otherwise identical dosage form lacking the polymeric binder when the dosage forms are stored for a storage period of six months at about 40° C. and about 75% relative humidity.

In another embodiment, the disclosure relates to a stable solid pharmaceutical dosage form comprising:

(a) about 0.25 mg to about 1.25 mg of atrasentan, or an equivalent amount of a pharmaceutically acceptable salt thereof; wherein the weight percent of atrasentan, or pharmaceutically acceptable salt thereof, in the dosage form is from about 0.05 weight percent to about 2.0 weight percent on an atrasentan free base equivalent weight basis;

(b) L-cysteine, or a pharmaceutically acceptable salt or ester thereof; wherein the molar ratio of the L-cysteine, or a pharmaceutically acceptable salt or ester thereof, to atrasentan, or pharmaceutically acceptable salt thereof, is from about 10:1 to about 1:10;

(c) a pharmaceutically acceptable polymeric binder selected from the group consisting of hydroxymethylpropylcellulose, hydroxyethylpropylcellulose, and hydroxypropylcellulose; wherein the weight to weight ratio of the binder to atrasentan, or pharmaceutically acceptable salt thereof, is from about 2:1 to about 25:1 on an atrasentan free base equivalent weight basis; and (d) a pharmaceutically acceptable diluent;

wherein degradation of atrasentan in the dosage form is less than degradation of atrasentan in an otherwise identical dosage form lacking the L-cysteine, or a pharmaceutically acceptable salt or ester thereof, and the polymeric binder when the dosage forms are stored for a storage period of six months at about 40° C. and about 75% relative humidity.

In additional aspects of each of the above embodiments, the dosage form is stored during the storage period in a semi-permeable container or a substantially impermeable container. In another aspect, the dosage form is stored during the storage period in a sealed HDPE bottle or a blister package. In another aspect, the dosage form is stored during the storage period in a sealed HDPE bottle. In another aspect, the dosage form is stored during the storage period in a blister package.

(i) Atrasentan

The dosage form can comprise a free base of atrasentan, a pharmaceutically acceptable salt of atrasentan, or a combination thereof. In one aspect, the dosage form comprises a free base of atrasentan. In another aspect, the dosage form comprises a pharmaceutically acceptable salt of atrasentan. In another aspect, the dosage form comprises a hydrochloride salt of atrasentan. In another aspect, the dosage form comprises atrasentan hydrochloride having a solid-state form selected from the group consisting of amorphous atrasentan hydrochloride, atrasentan hydrochloride Form I, atrasentan hydrochloride Form II, and atrasentan hydrochloride Form III. In another aspect, the dosage form comprises amorphous atrasentan hydrochloride. The properties and preparation of amorphous atrasentan hydrochloride are discussed in greater detail in WO 2006/034085. In another aspect, the dosage form comprises atrasentan hydrochloride Form I. The properties and preparation of atrasentan hydrochloride Form I are discussed in greater detail in WO 2006/034094. In another aspect, the dosage form comprises atrasentan hydrochloride Form II. The properties and preparation of atrasentan hydrochloride Form II are discussed in greater detail in WO 2006/034084. In another aspect, the dosage form comprises atrasentan hydrochloride Form III. The properties and preparation of atrasentan hydrochloride Form III are discussed in greater detail in WO 2006/034234.

In another embodiment, the weight percent of atrasentan, or pharmaceutically acceptable salt thereof, in the dosage form is from about 0.1 weight percent to about 2.0 weight percent on an atrasentan free base equivalent weight basis. In one aspect, the weight percent of atrasentan, or pharmaceutically acceptable salt thereof, in the dosage form is from about 0.2 weight percent to about 1.0 weight percent on an atrasentan free base equivalent weight basis. In another aspect, the weight percent of atrasentan, or pharmaceutically acceptable salt thereof, in the dosage form is from about 0.3 weight percent to about 0.8 weight percent on an atrasentan free base equivalent weight basis. In another aspect, the weight percent of atrasentan, or pharmaceutically acceptable salt thereof, in the dosage form is from about 0.40 weight percent to about 0.45 weight percent on an atrasentan free base equivalent weight basis. In another aspect, the weight percent of atrasentan, or pharmaceutically acceptable salt thereof, in the dosage form is from about 0.60 weight percent to about 0.65 weight percent on an atrasentan free base equivalent weight basis.

In another embodiment, the dosage form comprises from about 0.40 mg to about 1.00 mg of atrasentan, or an equivalent amount of a pharmaceutically acceptable salt thereof. In one aspect, the dosage form comprises from about 0.40 mg to about 0.85 mg of atrasentan, or an equivalent amount of a pharmaceutically acceptable salt thereof. In another aspect, the dosage form comprises about 0.50 mg of atrasentan, or an equivalent amount of a pharmaceutically acceptable salt thereof. In another aspect, the dosage form comprises about 0.75 mg of atrasentan, or an equivalent amount of a pharmaceutically acceptable salt thereof.

(ii) L-Cysteine

In one embodiment, the weight percent of the L-cysteine, or pharmaceutically acceptable salt or ester thereof, in the dosage form is from about 0.05 weight percent to about 1.0 weight percent. In one aspect, the weight percent of the L-cysteine, or pharmaceutically acceptable salt or ester thereof, in the dosage form is from about 0.07 weight percent to about 0.7 weight percent. In another aspect, the weight percent of the L-cysteine, or pharmaceutically acceptable salt or ester thereof, in the dosage form is from about 0.09 weight percent to about 0.5 weight percent.

In another embodiment, the molar ratio of the L-cysteine, or pharmaceutically acceptable salt or ester thereof, to atrasentan, or pharmaceutically acceptable salt thereof, in the dosage form is from about 10:1 to about 1:10. In another aspect, the molar ratio of the L-cysteine, or pharmaceutically acceptable salt or ester thereof, to atrasentan, or pharmaceutically acceptable salt thereof, in the dosage form is from about 5:1 to about 1:5. In another aspect, the molar ratio of the L-cysteine, or pharmaceutically acceptable salt or ester thereof, to atrasentan, or pharmaceutically acceptable salt thereof, is from about 2:1 to about 1:2. In another aspect, the molar ratio of the L-cysteine, or pharmaceutically acceptable salt or ester thereof, to atrasentan, or pharmaceutically acceptable salt thereof, about 1:1.

In another embodiment, the anti-oxidant is selected from the group consisting of L-cysteine hydrochloride monohydrate, L-cysteine hydrochloride anhydrate, and L-cysteine ethyl ester. In another aspect, the dosage form comprises L-cysteine hydrochloride monohydrate.

(iii) Diluent

In one embodiment, the weight percent of the diluent in the dosage form is from about 70 weight percent to about 99 weight percent. In one aspect, the weight percent of the diluent in the dosage form is from about 80 weight percent to about 99 weight percent. In another aspect, the weight percent of the diluent in the dosage form is from about 85 weight percent to about 99 weight percent. In another aspect, the diluent is selected from the group consisting of lactose, mannitol, isomalt, and combinations thereof. In another aspect, the diluent is lactose.

(iv) Binder

In one embodiment, the dosage form comprises a pharmaceutically acceptable polymeric binder selected from the group consisting of hydroxymethylpropylcellulose, hydroxyethylpropylcellulose, and hydroxypropylcellulose. In one aspect, the binder is hydroxypropyl methylcellulose. In another aspect, the binder is hydroxyethylpropyl-cellulose. In another aspect, the binder is hydroxypropylcellulose.

In another embodiment, the dosage form comprises a pharmaceutically acceptable polymeric binder selected from the group consisting of hydroxymethylpropylcellulose, hydroxyethylpropylcellulose, and hydroxypropylcellulose; and the weight percent of the binder in the dosage form is from about 1.0 weight percent to about 10.0 weight percent.

In one aspect, the weight percent of the binder in the dosage form is from about 1.0 weight percent to about 8.0 weight percent. In another aspect, the weight percent of the binder in the dosage form is from about 1.0 weight percent to about 5.0 weight percent.

In another embodiment, the dosage form further comprises a pharmaceutically acceptable polymeric binder selected from the group consisting of hydroxymethylpropylcellulose, hydroxyethylpropylcellulose, and hydroxypropylcellulose; and the weight to weight ratio of the binder to atrasentan, or pharmaceutically acceptable salt thereof, is from about 2:1 to about 25:1 on an atrasentan free base equivalent weight basis. In one aspect, the weight to weight ratio of the binder to the atrasentan, or pharmaceutically acceptable salt thereof, is from about 1:1 to about 20:1 on an atrasentan free base equivalent weight basis. In another aspect, the weight to weight ratio of the binder to the atrasentan, or pharmaceutically acceptable salt thereof, is from about 1:1 to about 15:1 on an atrasentan free base equivalent weight basis.

(v) Disintegrant

In one embodiment, the dosage form optionally comprises a pharmaceutically acceptable disintegrant. Suitable disintegrants for use in the disclosed dosage forms include, but are not limited to, cross-linked polyvinyl pyrrolidone (such as POLYPLASDONE™ XL), corn starch, potato starch, maize starch and modified starches (including sodium starch glycolate), agar-agar, alginic acids, microcrystalline cellulose, sodium croscarmellose, and combinations thereof. In one aspect, the disintegrant is selected from the group consisting of crospovidone, sodium starch glycolate, and sodium croscarmellose. In another aspect, the disintegrant is a cross-linked polyvinyl pyrrolidone. In another aspect, the disintegrant is crospovidone.

In another embodiment, the dosage form further comprises a pharmaceutically acceptable disintegrant. In one aspect, the dosage form further comprises a pharmaceutically acceptable disintegrant and the weight percent of the disintegrant in the dosage form is from about 1.0 weight percent to about 10.0 weight percent. In one aspect, the weight percent of the disintegrant in the dosage form is from about 1.0 weight percent to about 6.0 weight percent. In another aspect, the weight percent of the disintegrant in the dosage form is from about 1.0 weight percent to about 4.0 weight percent. In another aspect, the disintegrant is crospovidone.

In another embodiment, the dosage form further comprises a pharmaceutically acceptable disintegrant and the weight to weight ratio of the disintegrant to the L-cysteine, or pharmaceutically acceptable salt or ester thereof, is from about 60:1 to about 3:1. In one aspect, the weight to weight ratio of the disintegrant to the L-cysteine, or pharmaceutically acceptable salt or ester thereof, is from about 50:1 to about 4:1. In another aspect, the weight to weight ratio of the disintegrant to the L-cysteine, or pharmaceutically acceptable salt or ester thereof, is from about 35:1 to about 5:1.

(v) Additional Excipients

In further embodiments, the dosage form optionally comprises a pharmaceutically acceptable lubricant and/or glidant. In one aspect, the dosage form further comprises a pharmaceutically acceptable glidant. In another aspect, the weight percent of the glidant in the dosage form is from about 0.1 weight percent to about 1.5 weight percent. In another aspect, the weight percent of the glidant in the dosage form is from about 0.1 weight percent to about 1.0 weight percent. In another aspect, the weight percent of the glidant in the dosage form is from about 0.1 weight percent to about 0.8 weight percent. In another aspect, the glidant is silicon dioxide.

In another embodiment, the dosage form further comprises a pharmaceutically acceptable lubricant. In one aspect, the dosage form further comprises a pharmaceutically acceptable, hydrophobic lubricant. In another aspect, the weight percent of the lubricant in the dosage form is from about 0.05 weight percent to about 5.0 weight percent. In another aspect, the weight percent of the lubricant in the dosage form is from about 0.2 weight percent to about 3.0 weight percent. In another aspect, the weight percent of the lubricant in the dosage form is from about 0.5 weight percent to about 2.0 weight percent. In another aspect, the lubricant is glyceryl behenate.

In another embodiment, the dosage form further comprises a disintegrant, a glidant, and a lubricant.

(vi) Additional Embodiments

In one embodiment, the dosage form comprises a pharmaceutically acceptable polymeric binder selected from the group consisting of hydroxymethylpropylcellulose, hydroxyethylpropylcellulose, and hydroxypropylcellulose; the molar ratio of the L-cysteine, or pharmaceutically acceptable salt or ester thereof, to atrasentan, or pharmaceutically acceptable salt thereof, is from about 5:1 to about 1:5; and the weight to weight ratio of the binder to atrasentan, or pharmaceutically acceptable salt thereof, is from about 1:1 to about 20:1 on an atrasentan free base equivalent weight basis. In one aspect, this dosage form further comprises a disintegrant and the weight to weight ratio of the disintegrant to the L-cysteine, or pharmaceutically acceptable salt or ester thereof, is from about 60:1 to about 3:1. In another aspect, the weight percent of atrasentan, or pharmaceutically acceptable salt thereof, in this dosage form is from about 0.2 weight percent to about 1.0 weight percent on an atrasentan free base equivalent weight basis. In another aspect, this dosage form comprises from about 0.40 mg to about 0.85 mg of atrasentan, or an equivalent amount of a pharmaceutically acceptable salt thereof.

In another embodiment, the dosage form comprises a pharmaceutically acceptable polymeric binder selected from the group consisting of hydroxymethylpropylcellulose, hydroxyethylpropylcellulose, and hydroxypropylcellulose; the molar ratio of the L-cysteine, or a pharmaceutically acceptable salt or ester thereof, to atrasentan, or pharmaceutically acceptable salt thereof, is from about 2:1 to about 1:2; and the weight to weight ratio of the binder to atrasentan, or pharmaceutically acceptable salt thereof, is from about 1:1 to about 15:1 on an atrasentan free base equivalent weight basis. In one aspect, the dosage form further comprises a disintegrant and the weight to weight ratio of the disintegrant to the L-cysteine, or a pharmaceutically acceptable salt or ester thereof, is from about 50:1 to about 4:1. In another aspect, the weight percent of atrasentan, or pharmaceutically acceptable salt thereof, in this dosage form is from about 0.2 weight percent to about 1.0 weight percent on an atrasentan free base equivalent weight basis. In another aspect, this dosage form comprises from about 0.40 mg to about 0.85 mg of atrasentan, or an equivalent amount of a pharmaceutically acceptable salt thereof.

In another embodiment, the dosage form comprises a pharmaceutically acceptable polymeric binder selected from the group consisting of hydroxymethylpropylcellulose, hydroxyethylpropylcellulose, and hydroxypropylcellulose; the molar ratio of the L-cysteine, or pharmaceutically acceptable salt or ester thereof, to atrasentan, or pharmaceutically acceptable salt thereof, is about 1:1; and the weight to weight ratio of the binder to atrasentan, or pharmaceutically acceptable salt thereof, is from about 1:1 to about 15:1 on an atrasentan free base equivalent weight basis. In one aspect, this dosage form further comprises a disintegrant and the weight to weight ratio of the disintegrant to the L-cysteine, or pharmaceutically acceptable salt or ester thereof, is from about 35:1 to about 5:1. In another aspect, the weight percent of atrasentan, or pharmaceutically acceptable salt thereof, in this dosage form is from about 0.3 weight percent to about 0.8 weight percent on an atrasentan free base equivalent weight basis. In another aspect, this dosage form comprises from about 0.40 mg to about 0.85 mg of atrasentan, or an equivalent amount of a pharmaceutically acceptable salt thereof.

In another embodiment, the dosage form comprises a pharmaceutically acceptable polymeric binder selected from the group consisting of hydroxymethylpropylcellulose, hydroxyethylpropylcellulose, and hydroxypropylcellulose; the dosage form comprises from about 0.05 weight percent to about 1.0 weight percent of the L-cysteine, or pharmaceutically acceptable salt or ester thereof; and the dosage form comprises from about 1.0 weight percent to about 10.0 weight percent of the binder. In one aspect, this dosage form further comprises a disintegrant and the weight percent of the disintegrant in the dosage form is from about 1.0 weight percent to about 10.0 weight percent. In another aspect, the weight percent of atrasentan, or pharmaceutically acceptable salt thereof, in this dosage form is from about 0.1 weight percent to about 2.0 weight percent on an atrasentan free base equivalent weight basis. In another aspect, this dosage form comprises from about 0.40 mg to about 0.85 mg of atrasentan, or an equivalent amount of a pharmaceutically acceptable salt thereof.

In another embodiment, the dosage form comprises a pharmaceutically acceptable polymeric binder selected from the group consisting of hydroxymethylpropylcellulose, hydroxyethylpropylcellulose, and hydroxypropylcellulose; the dosage form comprises from about 0.07 weight percent to about 0.70 weight percent of the L-cysteine, or pharmaceutically acceptable salt or ester thereof; and the dosage form comprises from about 1.0 weight percent to about 8.0 weight percent of the binder. In one aspect, this dosage form further comprises a disintegrant and the weight percent of the disintegrant in the dosage form is from about 1.0 weight percent to about 6.0 weight percent. In another aspect, the weight percent of atrasentan, or pharmaceutically acceptable salt thereof, in this dosage form is from about 0.2 weight percent to about 1.0 weight percent on an atrasentan free base equivalent weight basis. In another aspect, this dosage form comprises from about 0.40 mg to about 0.85 mg of atrasentan, or an equivalent amount of a pharmaceutically acceptable salt thereof.

In another embodiment, the dosage form comprises a pharmaceutically acceptable polymeric binder selected from the group consisting of hydroxymethylpropylcellulose, hydroxyethylpropylcellulose, and hydroxypropylcellulose; the dosage form comprises from about 0.09 weight percent to about 0.80 weight percent of the L-cysteine, or pharmaceutically acceptable salt or ester thereof; and the dosage form comprises from about 1.0 weight percent to about 5.0 weight percent of the binder. In one aspect, this dosage form further comprises a disintegrant and the weight percent of the disintegrant in the dosage form is from about 1.0 weight percent to about 4.0 weight percent. In another aspect, the weight percent of atrasentan, or pharmaceutically acceptable salt thereof, in this dosage form is from about 0.3 weight percent to about 0.8 weight percent on an atrasentan free base equivalent weight basis. In another aspect, this dosage form comprises from about 0.40 mg to about 0.85 mg of atrasentan, or an equivalent amount of a pharmaceutically acceptable salt thereof.

In another embodiment, the dosage form comprises:

(a) about 0.1 weight percent to about 2.0 weight percent of atrasentan, or pharmaceutically acceptable salt thereof, on an atrasentan free base equivalent weight basis;

(b) about 0.05 weight percent to about 1.0 weight percent of the L-cysteine, or pharmaceutically acceptable salt or ester thereof;

(c) about 75 weight percent to about 99 weight percent of the diluent;

(d) about 1.0 weight percent to about 10.0 weight percent of the binder;

(e) optionally, about 1.0 weight percent to about 10.0 weight percent of a pharmaceutically acceptable disintegrant;

(f) optionally, about 0 weight percent to about 1.5 weight percent of a pharmaceutically acceptable glidant; and (g) optionally, about 0 weight percent to about 5.0 weight percent of a pharmaceutically acceptable lubricant;

wherein the cumulative weight percent for all components of the dosage form equals 100 percent.

In another embodiment, the dosage form comprises:

(a) about 0.1 weight percent to about 2.0 weight percent of atrasentan, or pharmaceutically acceptable salt thereof, on an atrasentan free base equivalent weight basis;

(b) about 0.05 weight percent to about 1.0 weight percent of the L-cysteine, or pharmaceutically acceptable salt or ester thereof;

(c) about 75 weight percent to about 99 weight percent of the diluent;

(d) about 1.0 weight percent to about 10.0 weight percent of the binder;

(e) about 1.0 weight percent to about 10.0 weight percent of a pharmaceutically acceptable disintegrant;

(f) optionally, about 0 weight percent to about 1.5 weight percent of a pharmaceutically acceptable glidant; and (g) optionally, about 0 weight percent to about 5.0 weight percent of a pharmaceutically acceptable lubricant;

wherein the cumulative weight percent for all components of the dosage form equals 100 percent.

In another embodiment, the dosage form comprises:

(a) about 0.2 weight percent to about 1.0 weight percent of atrasentan, or pharmaceutically acceptable salt thereof, on an atrasentan free base equivalent weight basis;

(b) about 0.07 weight percent to about 0.70 weight percent of the L-cysteine, or pharmaceutically acceptable salt or ester thereof;

(c) about 82 weight percent to about 99 weight percent of the diluent;

(d) about 1.0 weight percent to about 8.0 weight percent of the binder;

(e) optionally, about 1.0 weight percent to about 6.0 weight percent of a pharmaceutically acceptable disintegrant;

(f) optionally, about 0 weight percent to about 1.0 weight percent of a pharmaceutically acceptable glidant; and (g) optionally, about 0 weight percent to about 3.0 weight percent of a pharmaceutically acceptable lubricant;

wherein the cumulative weight percent for all components of the dosage form equals 100 percent.

In another embodiment, the dosage form comprises:

(a) about 0.2 weight percent to about 1.0 weight percent of atrasentan, or pharmaceutically acceptable salt thereof, on an atrasentan free base equivalent weight basis;

(b) about 0.07 weight percent to about 0.70 weight percent of the L-cysteine, or pharmaceutically acceptable salt or ester thereof;

(c) about 82 weight percent to about 99 weight percent of the diluent;

(d) about 1.0 weight percent to about 8.0 weight percent of the binder;

(e) about 1.0 weight percent to about 6.0 weight percent of a pharmaceutically acceptable disintegrant;

(f) optionally, about 0 weight percent to about 1.0 weight percent of a pharmaceutically acceptable glidant; and (g) optionally, about 0 weight percent to about 3.0 weight percent of a pharmaceutically acceptable lubricant;

wherein the cumulative weight percent for all components of the dosage form equals 100 percent.

In another embodiment, the dosage form comprises:

(a) about 0.3 weight percent to about 0.8 weight percent of atrasentan, or pharmaceutically acceptable salt thereof, on an atrasentan free base equivalent weight basis;

(b) about 0.09 weight percent to about 0.50 weight percent of the L-cysteine, or pharmaceutically acceptable salt or ester thereof;

(c) about 87 weight percent to about 99 weight percent of the diluent;

(d) about 1.0 weight percent to about 5.0 weight percent of the binder;

(e) optionally, about 1.0 weight percent to about 4.0 weight percent of a pharmaceutically acceptable disintegrant;

(f) optionally, about 0 weight percent to about 0.75 weight percent of a pharmaceutically acceptable glidant; and (g) optionally, about 0 weight percent to about 2.0 weight percent of a pharmaceutically acceptable lubricant;

wherein the cumulative weight percent for all components of the dosage form equals 100 percent.

In another embodiment, the dosage form comprises:

(a) about 0.3 weight percent to about 0.8 weight percent of atrasentan, or pharmaceutically acceptable salt thereof, on an atrasentan free base equivalent weight basis;

(b) about 0.09 weight percent to about 0.50 weight percent of the L-cysteine, or pharmaceutically acceptable salt or ester thereof;

(c) about 87 weight percent to about 99 weight percent of the diluent;

(d) about 1.0 weight percent to about 5.0 weight percent of the binder;

(e) about 1.0 weight percent to about 4.0 weight percent of a pharmaceutically acceptable disintegrant;

(f) optionally, about 0 weight percent to about 0.75 weight percent of a pharmaceutically acceptable glidant; and (g) optionally, about 0 weight percent to about 2.0 weight percent of a pharmaceutically acceptable lubricant;

wherein the cumulative weight percent for all components of the dosage form equals 100 percent.

In another embodiment, the dosage form satisfies one or more of the following conditions:

(a) the diluent is lactose;

(b) the dosage form comprises a pharmaceutically acceptable binder and the binder is hydroxypropyl methylcellulose;

(c) the dosage form comprises a pharmaceutically acceptable disintegrant and the disintegrant is crospovidone;

(d) the dosage form comprises a pharmaceutically acceptable glidant and the glidant is silicon dioxide;

(e) the dosage form comprises a pharmaceutically acceptable lubricant and the lubricant is glyceryl behenate.

In another embodiment, the dosage form is a tablet. In one aspect, the tablet has a weight from about 37.5 mg to about 1500 mg. In another aspect, the tablet has a weight from about 50 mg to about 750 mg. In another aspect, the tablet has a weight from about 50 mg to about 250 mg. In another aspect, the tablet has a weight from about 75 mg to about 500 mg. In another aspect, the tablet has a weight from about 75 mg to about 150 mg. In another aspect, the tablet has a weight from about 100 mg to about 250 mg. In another aspect, the tablet has a weight from about 100 mg to about 230 mg.

In general, the tablet optionally can be surrounded or coated with at least one non-rate-controlling layer. The non-rate-controlling layer can be formed as a single layer, coating or membrane or a plurality of single layers, coatings or membranes. The functions of the non-rate-controlling layer can include, for example, providing further stability for the atrasentan, serving as a process aid and/or as a cosmetic enhancement for the formulation, and/or acting as a masking agent to reduce any undesired odor associated with the formulation (such as the odor commonly associated with L-cysteine).

When the dosage form comprises a non-rate-controlling layer, the non-rate-controlling layer can be made of one or more polymers, as well as, other ingredients known in the art, such as, but not limited to, plasticizers, pigments/opacifiers, waxes, etc. Examples of polymers that can be used include, but are not limited to, hydroxypropyl methylcellulose, hydroxypropyl cellulose, methylcellulose, polyvinyl alcohol and polyethylene glycol. Examples of plasticizers that can be used include, but are not limited to, polyethylene glycol(s), glycerin, triacetin, triethyl citrate, diethyl phthalate, L-cysteine, and mineral oils. Examples of pigments/opacifiers that can be used include, but are not limited to, water soluble dyes (for example, sunset yellow, quinoline yellow, erythrosine, and tartrazine), pigments (for example, aluminum lakes, titanium oxides, iron oxides and talc), and natural products (for example, riboflavin, carotenoids, chlorophyll, anthocyanins, and carmine). An example of a wax that can be used includes, but is not limited to, a paraffin wax.

In another embodiment, the dosage form is a tablet coated with a pharmaceutically acceptable polymer.

In another embodiment, the dosage form is a capsule.

In another embodiment, the dosage form is packaged in a semi-permeable container. In one aspect, the semi-permeable container is a blister pack.

In another embodiment, the dosage form is packaged in a substantially impermeable container.

In another embodiment, the dosage form is an immediate release dosage form. In one aspect, the dosage form is an immediate release tablet and releases at least about 85% of the atrasentan, or pharmaceutically acceptable salt thereof, within about 45 minutes as determined in an in vitro dissolution test conducted using a USP Dissolution Apparatus 2 (Paddle Apparatus), a 0.01N hydrochloric acid dissolution medium, and a paddle rotation of 50 RPM. In another aspect, the dosage form is an immediate release tablet and releases at least about 75% of the atrasentan, or pharmaceutically acceptable salt thereof, within about 30 minutes.

In another embodiment, the dosage form comprises less than about 1.0 weight percent of total impurities resulting from degradation of the atrasentan, or pharmaceutically acceptable salt thereof, after a storage period of six months at about 40° C. and about 75% relative humidity. In one aspect, degradation of the atrasentan, or pharmaceutically acceptable salt thereof, is analyzed using high-performance liquid chromatography.

In another embodiment, the dosage form comprises less than about 0.6 weight percent of any single impurity resulting from degradation of the atrasentan, or pharmaceutically acceptable salt thereof, after a storage period of six months at about 40° C. and about 75% relative humidity. In one aspect, degradation of the atrasentan, or pharmaceutically acceptable salt thereof, is analyzed using high-performance liquid chromatography.

In another embodiment, the dosage form comprises less than about 1.0 weight percent of total impurities and less than about 0.6 weight percent of any single impurity resulting from degradation of the atrasentan, or pharmaceutically acceptable salt thereof, after a storage period of six months at about 40° C. and about 75% relative humidity. In one aspect, degradation of the atrasentan, or pharmaceutically acceptable salt thereof, is analyzed using high-performance liquid chromatography.

III. Methods of Treatment

The present disclosure also relates to methods of treating a condition in a subject, particularly a human subject suffering from or susceptible to the condition, comprising administering once daily to the subject a stable solid pharmaceutical dosage form comprising atrasentan, or a pharmaceutically acceptable salt thereof, as described in any of the embodiments of the disclosure.

In one embodiment, the present disclosure relates to methods of treating nephropathy in a human subject suffering from or susceptible to nephropathy comprising administering once daily to the subject a stable solid pharmaceutical dosage form comprising atrasentan, or a pharmaceutically acceptable salt thereof, as described in any of the embodiments of the disclosure. In a further aspect, the nephropathy treated is diabetic nephropathy. In a further aspect, the subject selected for treatment is suffering from diabetic nephropathy. In a further aspect, the subject selected for treatment is suffering from type 2 diabetes mellitus. In a further aspect, the subject selected for treatment is suffering from one or more of the following conditions: (a) diabetic nephropathy; (b) type 2 diabetes; (c) Stage 3 chronic kidney disease, Stage 4 chronic kidney disease, or end stage renal disease; (d) a urinary-albumin-to-creatinine ratio greater than about 30 mg/g (i.e., the subject is suffering from microalbuminuria); (e) a urinary-albumin-to-creatinine ratio greater than about 300 mg/g (i.e., the subject is suffering from macroalbuminuria); and/or (f) an estimated glomerular filtration rate from about 25 ml/min/1.73 m$^2$ to about 59 ml/min/1.73 m$^2$. In a further aspect, the subject is also administered a second therapeutic agent that inhibits one or more elements of the renin-angiotensin-aldosterone system. In a further aspect, the second therapeutic agent that inhibits one or more elements of the renin-angiotensin-aldosterone system is selected from the group consisting of diuretics, angiotensin converting enzyme inhibitors, angiotensin II receptor blockers, calcium channel blockers, renin inhibitors, and aldosterone antagonists. In a further aspect, the second therapeutic agent that inhibits one or more elements of the renin-angiotensin-aldosterone system is selected from the group consisting of angiotensin converting enzyme inhibitors and angiotensin II receptor blockers.

In another embodiment, the present disclosure relates to methods of treating chronic kidney disease in a human subject suffering from or susceptible to chronic kidney disease comprising administering once daily to the subject a stable solid pharmaceutical dosage form comprising atrasentan, or a pharmaceutically acceptable salt thereof, as described in any of the embodiments of the disclosure. In a further aspect, the chronic kidney disease is Stage 3 or Stage 4 chronic kidney disease. In a further aspect, the chronic kidney disease is end stage renal disease. In a further aspect, the treatment delays progression of chronic kidney disease in the subject. In a further aspect, the treatment delays progression of end stage renal disease in the subject. In a further aspect, the subject selected for treatment is suffering from diabetic nephropathy. In a further aspect, the subject selected for treatment is suffering from type 2 diabetes mellitus. In a further aspect, the subject selected for treatment is suffering from Stage 3 or Stage 4 chronic kidney disease. In a further aspect, the subject selected for treatment is suffering from end stage renal disease. In a further aspect, the subject selected for treatment is suffering from one or more of the following conditions: (a) diabetic nephropathy; (b) type 2 diabetes; (c) Stage 3 chronic kidney disease, Stage 4 chronic kidney disease, or end stage renal disease; (d) a urinary-albumin-to-creatinine ratio greater than about 30 mg/g; (e) a urinary-albumin-to-creatinine ratio greater than about 300 mg/g; and/or (f) an estimated glomerular filtration rate from about 25 ml/min/1.73 m$^2$ to about 59 ml/min/1.73 m$^2$. In a further aspect, the subject is also administered a second therapeutic agent that inhibits one or more elements of the renin-angiotensin-aldosterone system. In a further aspect, the second therapeutic agent that inhibits one or more elements of the renin-angiotensin-aldosterone system is selected from the group consisting of diuretics, angiotensin converting enzyme inhibitors, angiotensin II receptor blockers, calcium channel blockers, renin inhibitors, and aldosterone antagonists. In a further aspect, the second therapeutic agent that inhibits one or more elements of the renin-angiotensin-aldosterone system is selected from the group consisting of angiotensin converting enzyme inhibitors and angiotensin II receptor blockers.

In another embodiment, the present disclosure relates to methods of reducing the urinary-albumin-to-creatinine ratio in a human subject suffering from or susceptible chronic kidney disease comprising administering once daily to the subject a stable solid pharmaceutical dosage form comprising atrasentan, or a pharmaceutically acceptable salt thereof, as described in any of the embodiments of the disclosure.

In another embodiment, the present disclosure relates to methods of reducing the rate of increase in serum creatinine concentration in a human subject suffering from or susceptible to chronic kidney disease comprising administering once daily to the subject a stable solid pharmaceutical dosage form comprising atrasentan, or a pharmaceutically acceptable salt thereof, as described in any of the embodiments of the disclosure.

In another embodiment, the present disclosure relates to the use of a stable solid pharmaceutical dosage form comprising atrasentan, or a pharmaceutically acceptable salt thereof, for treating a condition as described in the various embodiments of the disclosure.

IV. Combination Therapy and Fixed-Dose Combinations

The methods of the present disclosure also contemplate treatments comprising administering a stable solid pharmaceutical dosage form comprising atrasentan, or a pharmaceutically acceptable salt thereof, as described in any of the embodiments of the disclosure in combination with one or more additional therapeutic agents (such as an inhibitor of one or more elements of the renin-angiotensin-aldosterone system as previously discussed above). Accordingly, the dosage forms of the present disclosure can be administered alone or in combination with one or more additional therapeutic agents. When administered in combination with one or more additional therapeutic agents, separate dosage forms can be administered to the subject or a single dosage form comprising both atrasentan, or a pharmaceutically acceptable salt thereof, and the additional therapeutic agent(s) can be administered to the subject. If administered as a separate dosage form, the additional therapeutic agent may be administered simultaneously with the atrasentan dosage form of the present disclosure or sequentially with the atrasentan dosage form of the present disclosure.

Representative additional therapeutic agents include, for example, diuretics, antihypertensive agents, therapeutic agents for diabetes or diabetic complications, and therapeutic agents for hyperlipidemia.

In one embodiment, the dosage forms of the present disclosure may be co-administered with one or more diuretics such as hydroclorothiazide (such as MICROZIDE™ or ORETIC™), hydroflumethiazide (such as SALURON™), bemetanide (such as BUMEX™), torsemide (such as DEMADEX™), metolazone (such as ZAROXOLYN™), chlorothiazide (such as DIURIL™, ESIDRIX™ or HYDRODIURIL™), triamterene (such as DYRENIUM™), ethacrynic acid (such as EDECRIN™), chlorthalidone (such as HYGROTON™), furosemide (such as LASIX™), indapamide (such as LOZOL™), or amiloride (such as MIDAMOR™ or MODURETIC™).

In another embodiment, the dosage forms of the present disclosure may be co-administered with one or more angiotensin converting enzyme (ACE) inhibitors such as quinapril (such as ACCUPRIL™), perindopril (such as ACEON™), captopril (such as CAPOTEN™), enalapril (such as VASOTEC™), ENALAPRILAT™, ramipril (such as ALTACE™), cilazapril, delapril, fosenopril (such as MONOPRIL™), zofenopril, indolapril, benazepril (such as LOTENSIN™), lisinopril (such as PRINIVIL™ or ZESTRIL™), spirapril, trandolapril (such as MAVIK™), perindep, pentopril, moexipril (such as UNIVASC™), or pivopril.

In another embodiment, the dosage forms of the present disclosure may be co-administered with one or more angiotensin II receptor blockers such as candesartan (such as ATACAND™), eprosartan (such as TEVETEN™), irbesartan (such as AVEPRO™), losartan (such as COZAAR™), olmesartan, olmesartan medoxomil (such as BENICAR™), tasosartan, telmisartan (such as MICARDIS™), valsartan (such as DIOVAN™), zolasartan, F1-6828K, RNH-6270, UR-7198, Way-126227, KRH-594, TAK-536, BRA-657, or TA-606.

In another embodiment, the dosage forms of the present disclosure may be co-administered with one or more calcium channel blockers such as nifedipine (such as ADALAT™, ADALAT CC™, or PROCARDIA™), verapamil (such as GALAN™, COVERA-HS™, ISOPTIN SR™, or VERELAN™), diltiazem (such as CARDIZEM™, CARDIZEM CD™, CARDIZEM LA™, CARDIZEM SR™, DILACOR™, TIAMATE™, or TIAZAC™), isradipine (such as DYNACIRC™ or DYNACIRC CR™), amlodipine (such as NORVASC™), felodipine (such as PLENDIL™), nisoldipine (such as SULAR™), bepridil (such as VASCOR™), vatanidipine, clevidipine, lercanidipine, or dilitiazem.

In another embodiment, the dosage forms of the present disclosure may be co-administered with one or more renin inhibitors such as aliskiren (such as TEKTURNA™).

In another embodiment, the dosage forms of the present disclosure may be co-administered with one or more aldosterone receptor antagonists such as eplerenone (such as INSPRA™) or spironolactone (such as ALDACTONE™).

In another embodiment, the dosage forms of the present disclosure may be co-administered with one or more alpha blockers such as dozazosin (such as CARDURA™) phenoxybenzamine (such as DIBENZYLINE™), terazosin (such as HYTRIN™), CDR1-93/478, or CR-2991.

In another embodiment, the dosage forms of the present disclosure may be co-administered with one or more beta blockers such as timolol (such as BLOCARDEN™) carteolol (such as CARTROL™), carvedilol (such as COREG™), nadolol (such as CORGARD™), propranolol (such as INNOPRAN XL™), betaxolol (such as KERLONE™) penbutolol (such as LEVATOL™), metoprolol (such as LOPRESSOR™ or TOPROL-XL™), atenolol (such as TENORMIN™), pindolol (such as VISKEN™), or bisoprolol.

In another embodiment, the dosage forms of the present disclosure may be co-administered with one or more alpha-beta blockers such as labetalol (such as NORMODYNE™ or TRANDATE™).

In another embodiment, the dosage forms of the present disclosure may be co-administered with one or more central antiadrenergics such as methyldopa (such as ALDOMET™), clonidine (such as CATAPRES™ or CATAPRES-TTS™), guanfacine (such as TENEX™), or guanabenz (such as WYTENSIN™).

In another embodiment, the dosage forms of the present disclosure may be co-administered with one or more glycosides/inotropic agents such as digoxin (such as LANOXIN™).

In another embodiment, the dosage forms of the present disclosure may be co-administered with one or more alpha glucosidase inhibitors, such as miglitol (such as GLYSET™) or acarbose (such as PRECOSE™).

In another embodiment, the dosage forms of the present disclosure may be co-administered with one or more biguanides, such as roseiglitazone (such as AVANDAMET™) or metformin (such as GLUCOPHAGE™ or GLUCOPHAGE XR™).

In another embodiment, the dosage forms of the present disclosure may be co-administered with one or more insulins, such as HUMALOG™, HUMALOG 50/50™, HUMALOG 75/25™, HUMULIN 50/50™, HUMALIN 75/25™, HUMALIN L™, HUMALIN N™, HUMALIN R™, HUMALIN R U-500™, HUMALIN U™, ILETIN II LENTE™, ILETIN II NPH™, ILETIN II REGULAR™, LANTUS™, NOVOLIN 70/30™, NOVILIN N™ NOVILIN R™, NOVOLOG™, or VELOSULIN BR™, and EXUBERA™.

In another embodiment, the dosage forms of the present disclosure may be co-administered with one or more meglitnides, such as repaglinide (such as PRANDIN™) or nateglinide (such as STARLIX™).

In another embodiment, the dosage forms of the present disclosure may be co-administered with one or more sulfonylureas, such as glimepiride (such as AMARYL™), glyburide (such as DIABETA™, GLYNASE PRESTAB™ or MICRONASE™), or glipizide (such as GLUCOTROL™, or GLUCOTROL XL™).

In another embodiment, the dosage forms of the present disclosure may be co-administered with one or more thiazolidinediones, such as pioglitazone (such as ACTOS™) or rosiglitazone (such as AVANDIA™).

In another embodiment, the dosage forms of the present disclosure may be co-administered with niacin or one or more nicotinic acid derivatives, such as NIACOR™ NIASPAN™, NICOLAR™, or SLO-NIACIN™.

In another embodiment, the dosage forms of the present disclosure may be co-administered with one or more fibric acid derivatives, such as clofibrate (such as ATROMID-S™), gemfibrozil (such as LOPID™), or fenofibrate (such as TRICOR™).

In another embodiment, the dosage forms of the present disclosure may be co-administered with one or more bile acid sequestants, such as colestipol (such as COLESTID™), cholestyramine (such as LOCHOLEST™, PREVALITE™, QUESTRAN™, or QUESTRAN LIGHT™), or colesevelam (such as WELCHOL™).

In another embodiment, the dosage forms of the present disclosure may be co-administered with one or more cholesterol absorption inhibitors, such as ezetimibe (such as ZETIA™).

In another embodiment, the dosage forms of the present disclosure may be co-administered with one or more 3-hydroxy-3-methylglutaryl coenzyme A (HMG-CoA) reductase inhibitors (statins) such as fluvastatin (such as LESCOL™), atorvastatin (such as LIPITOR™), lovastatin (such as ALTOCOR™ or MEVACOR™), pravastatin (such as PRAVACHOL™), rosuvastatin (such as CRESTOR™), or simvastatin (such as ZOCOR™).

In another embodiment, the present disclosure relates to the use of a first dosage form in combination with a second dosage form for treating a condition as described in the various embodiments of the disclosure, wherein the first dosage form is a stable solid pharmaceutical dosage form comprising atrasentan, or a pharmaceutically acceptable salt thereof, as described in any of the embodiments of the disclosure, and the second dosage form comprises a second therapeutic agent.

In another embodiment, the present disclosure relates to the use of a stable solid pharmaceutical dosage form comprising atrasentan, or a pharmaceutically acceptable salt thereof, for treating a condition as described in the various embodiments of the disclosure, wherein the dosage form further comprises a second therapeutic agent.

In another embodiment, the present disclosure relates to a stable solid pharmaceutical dosage form comprising atrasentan, or a pharmaceutically acceptable salt thereof, and further comprising a second therapeutic agent. In one aspect, the second therapeutic agent inhibits one or more elements of the renin-angiotensin-aldosterone system. In a further aspect, the second therapeutic agent is selected from the group consisting of diuretics, angiotensin converting enzyme inhibitors, angiotensin II receptor blockers, calcium channel blockers, renin inhibitors, and aldosterone antagonists. In a further aspect, the second therapeutic agent is selected from the group consisting of angiotensin converting enzyme inhibitors and angiotensin II receptor blockers. In a further aspect, the second therapeutic agent is an angiotensin converting enzyme inhibitor. In a further aspect, the second therapeutic agent is an angiotensin II receptor blocker.

V. Kits

The present disclosure also relates to kits comprising one or more stable solid pharmaceutical dosage forms comprising atrasentan, or a pharmaceutically acceptable salt thereof, as described in any of the embodiments of the disclosure. The kit optionally can comprise one or more additional therapeutic agents and/or instructions, for example, instructions for using the kit.

In one embodiment, the kit comprises a semi-permeable container containing one or more stable solid pharmaceutical dosage forms comprising atrasentan, or a pharmaceutically acceptable salt thereof, as described in any of the embodiments of the disclosure. In one aspect, the semi-permeable container is a blister pack.

In another embodiment, the kit comprises a substantially impermeable container containing one or more stable solid pharmaceutical dosage forms comprising atrasentan, or a pharmaceutically acceptable salt thereof, as described in any of the embodiments of the disclosure.

In another embodiment, the kit comprises a first dosage form and a second dosage form, wherein the first dosage form is a stable solid pharmaceutical dosage form comprising atrasentan, or a pharmaceutically acceptable salt thereof, as described in any of the embodiments of the disclosure, and the second dosage form comprises a second therapeutic agent. In a further aspect, the second therapeutic agent is selected from the group consisting of diuretics, angiotensin converting enzyme inhibitors, angiotensin II receptor blockers, calcium channel blockers, renin inhibitors, and aldosterone antagonists. In a further aspect, the second therapeutic agent is selected from the group consisting of angiotensin converting enzyme inhibitors and angiotensin II receptor blockers. In a further aspect, the second therapeutic agent is an angiotensin converting enzyme inhibitor. In a further aspect, the second therapeutic agent is an angiotensin II receptor blocker. In a further aspect, the kit comprises a semi-permeable container containing the first dosage form and the second dosage form. In a further aspect, the kit comprises a blister pack containing the first dosage form and the second dosage form. In a further aspect, the kit comprises an impermeable container containing the first dosage form and the second dosage form.

VI. Methods of Preparation

The present disclosure also relates to methods for preparing a stable solid pharmaceutical dosage form comprising about 0.25 mg to about 1.25 mg of atrasentan, or pharmaceutically acceptable salt thereof, as described in any of the embodiments of the disclosure. In general, these dosage forms can be prepared using conventional techniques known in the art such as, but not limited to, direct blending, dry granulation (roller compaction), wet granulation (high shear granulation), milling or sieving, drying (if wet granulation is used), compression, and, optionally, coating. It is believed, however, that dosage form stability improves when the low dose of atrasentan, or pharmaceutically acceptable salt thereof, is first combined with at least a portion of a pharmaceutically acceptable polymeric binder to form a first mixture and the first mixture is then blended with the remaining components during the preparation of the dosage form. It is further believed that it is additionally advantageous to include a pharmaceutically acceptable anti-oxidant as one of the components during the preparation of the dosage form.

A. Pre-Treatment of Atrasentan with HPMC

In one embodiment, the present disclosure relates to methods for the preparation of a stable solid pharmaceutical dosage form comprising about 0.25 mg to about 1.25 mg of atrasentan, or pharmaceutically acceptable salt thereof, as described in any of the embodiments of the disclosure; wherein the method comprises:

(a) combining the atrasentan, or a pharmaceutically acceptable salt thereof, with at least a portion of a pharmaceutically acceptable polymeric binder to form a first mixture;

(b) blending the first mixture with a pharmaceutically acceptable diluent to form a second mixture; and (c) encapsulating or tableting the second mixture to yield the dosage form.

In one aspect, the first mixture is a liquid mixture. In another aspect, the first mixture is a liquid mixture, the blending step comprises wet granulation, and the first mixture is used as a granulating agent. In another aspect, the first mixture is a dry mixture. In another aspect, the first mixture is a dry mixture and the first mixture is compressed before it is blended with the diluent.

In another embodiment, the present disclosure relates to methods for the preparation of a stable solid pharmaceutical dosage form as described in any of the embodiments of the disclosure; wherein the dosage form comprises about 0.25 mg to about 1.25 mg of atrasentan, or pharmaceutically acceptable salt thereof; a pharmaceutically acceptable anti-oxidant; a pharmaceutically acceptable diluent; and a pharmaceutically acceptable polymeric binder selected from the group consisting of hydroxymethylpropylcellulose, hydroxyethylpropylcellulose, and hydroxypropylcellulose; and wherein the method comprises:

(a) combining the atrasentan, or a pharmaceutically acceptable salt thereof, with at least a portion of the polymeric binder to form a first mixture;

(b) blending the first mixture with the diluent to form a second mixture; and (c) encapsulating or tableting the second mixture to yield the dosage form.

In one aspect, the polymeric binder is hydroxypropyl methylcellulose. In another aspect, the polymeric binder is hydroxypropylethylcellulose. In another aspect, the polymeric binder is hydroxypropylcellulose. In another aspect, the weight percent of the polymeric binder in the dosage form is from about 1.0 weight percent to about 10.0 weight percent. In another aspect, the first mixture is a liquid mixture. In another aspect, the first mixture is a liquid mixture, the blending step comprises wet granulation, and the first mixture is used as a granulating agent. In another aspect, the first mixture is a dry mixture. In another aspect, the first mixture is a dry mixture and the first mixture is compressed before it is blended with the diluent.

Where the first mixture is a liquid mixture, the liquid mixture comprises a pharmaceutically acceptable liquid such as water. In one aspect, the first mixture is an aqueous mixture. In another aspect, the first mixture is an aqueous suspension of atrasentan, or a pharmaceutically acceptable salt thereof. In another aspect, the first mixture is an aqueous solution of atrasentan, or a pharmaceutically acceptable salt thereof. In another aspect, the first mixture is an aqueous mixture, the blending step comprises wet granulation, and the first mixture is used as a granulating agent. In another aspect of the various embodiments employing wet granulation, a first portion of the polymeric binder is combined with the atrasentan, or a pharmaceutically acceptable salt thereof, to prepare the first mixture, and a second portion of the polymeric binder is added to the granulation bowl used to prepare the second mixture.

In one embodiment, the liquid mixture has a viscosity that is sufficient to maintain the atrasentan, or pharmaceutically acceptable salt thereof, in suspension.

In another embodiment, the atrasentan, or pharmaceutically acceptable salt thereof, is dissolved in the liquid mixture.

In another embodiment, the weight percent of the polymeric binder in the liquid mixture is from about 0.5 weight percent to about 15.0 weight percent. In another aspect, the weight percent of the polymeric binder is from about 0.5 weight percent to about 12.0 weight percent. In another aspect, the weight percent of the polymeric binder is from about 0.5 weight percent to about 10.0 weight percent.

In another embodiment, the weight percent of the atrasentan, or pharmaceutically acceptable salt thereof, in the liquid mixture is from about 2.0 weight percent to about 12.0 weight percent. In another aspect, the weight percent of atrasentan, or pharmaceutically acceptable salt thereof, is from about 3.0 weight percent to about 10.0 weight percent. In another aspect, the weight percent of atrasentan, or pharmaceutically acceptable salt thereof, is from about 4.0 weight percent to about 8.0 weight percent.

In another embodiment, the weight to weight ratio of the polymeric binder to atrasentan, or a pharmaceutically acceptable salt thereof, in the liquid mixture is from about 5:1 to about 1:5. In one aspect, the weight to weight ratio of the polymeric binder to atrasentan, or a pharmaceutically acceptable salt thereof, is from about 3.5:1 to about 1:3.5. In another aspect, the weight to weight ratio of the polymeric binder to atrasentan, or a pharmaceutically acceptable salt thereof, in the first mixture is from about 1:2 to about 2:1.

In another embodiment, at least two of the following conditions are satisfied: (a) the weight percent of the polymeric binder in the liquid mixture is from about 0.5 weight percent to about 15.0 weight percent; (b) the weight percent of atrasentan, or pharmaceutically acceptable salt thereof, in the first mixture is from about 2.0 weight percent to about 12.0 weight percent; and/or (c) the weight to weight ratio of the polymeric binder to atrasentan, or a pharmaceutically acceptable salt thereof, in the first mixture is from about 5:1 to about 1:5 on an atrasentan free base equivalent weight basis. In one aspect, at least two of the following conditions are satisfied: (a) the weight percent of the polymeric binder in the liquid mixture is from about 0.5 weight percent to about 12.0 weight percent; (b) the weight percent of atrasentan, or pharmaceutically acceptable salt thereof, in the first mixture is from about 3.0 weight percent to about 10.0 weight percent; and/or (c) the weight to weight ratio of the polymeric binder to atrasentan, or a pharmaceutically acceptable salt thereof, in the first mixture is from about 3.5:1 to about 1:3.5 on an atrasentan free base equivalent weight basis. In another aspect, at least two of the following conditions are satisfied: (a) the weight percent of the polymeric binder in the liquid mixture is from about 0.5 weight percent to about 10.0 weight percent; (b) the weight percent of atrasentan, or pharmaceutically acceptable salt thereof, in the first mixture is from about 4.0 weight percent to about 8.0 weight percent; and/or (c) the weight to weight ratio of the polymeric binder to atrasentan, or a pharmaceutically acceptable salt thereof, in the first mixture is from about 1:2 to about 2:1 on an atrasentan free base equivalent weight basis.

In each of the above-discussed methods, the second mixture additionally may comprise an anti-oxidant, a disintegrant, a glidant, and/or a lubricant. In one aspect, the second mixture comprises an anti-oxidant. In another aspect, the second mixture comprises a disintegrant. In another aspect, the second mixture comprises a glidant. In another aspect, the second mixture comprises a lubricant. In another aspect, the second mixture comprises an anti-oxidant, a disintegrant, a glidant, and a lubricant. In another aspect, the anti-oxidant is L-cysteine, or a pharmaceutically acceptable salt or ester thereof. In another aspect, the second mixture comprises L-cysteine, or a pharmaceutically acceptable salt or ester thereof, a disintegrant, a glidant, and a lubricant.

B. Atrasentan-Coated Tablet

The stable solid pharmaceutical dosage form comprising about 0.25 mg to about 1.25 mg of atrasentan, or pharmaceutically acceptable salt thereof, as described in any of the embodiments of the disclosure also can be prepared as an atrasentan-coated tablet (i.e., a tablet coated with atrasentan). In one embodiment, the present disclosure relates to methods for the preparation of a stable solid pharmaceutical dosage form comprising about 0.25 mg to about 1.25 mg of atrasentan, or pharmaceutically acceptable salt thereof, as described in any of the embodiments of the disclosure; wherein the method comprises:

(a) combining the atrasentan, or a pharmaceutically acceptable salt thereof, and a pharmaceutically acceptable polymer selected from the group consisting of hydroxymethylpropylcellulose, hydroxyethylpropylcellulose, and hydroxypropylcellulose to form a coating mixture; and (b) applying the coating mixture to the surface of a tablet core comprising a pharmaceutically acceptable diluent to yield the dosage form.

In one aspect, one or both of the following conditions are satisfied: (a) the weight percent of atrasentan, or pharmaceutically acceptable salt thereof, in the dosage form is from about 0.05 weight percent to about 2.0 weight percent on an atrasentan free base equivalent weight basis; and/or (b) the weight percent of the polymer in the dosage form is from about 0.5 weight percent to about 15.0 weight percent. In another aspect, the polymer is hydroxypropyl methylcellulose. In another aspect, the polymer is hydroxypropylethylcellulose. In another aspect, the polymer is hydroxypropylcellulose.

In various additional embodiments, the tablet additionally may comprise an anti-oxidant, a disintegrant, a glidant, and/or a lubricant. In one aspect, the tablet comprises an anti-oxidant. In another aspect, the tablet comprises a disintegrant. In another aspect, the tablet comprises a glidant. In another aspect, the tablet comprises a lubricant. In another aspect, the tablet comprises an anti-oxidant, a disintegrant, a glidant, and a lubricant. In another aspect, the anti-oxidant is L-cysteine, or a pharmaceutically acceptable salt or ester thereof. In another aspect, the tablet comprises L-cysteine, or a pharmaceutically acceptable salt or ester thereof, a disintegrant, a glidant, and a lubricant.

In an alternative embodiment, step (b) of the above-described method instead involves applying the coating mixture to the surface of particles (e.g., beads, granules, pellets, or the like) comprising a pharmaceutically acceptable diluent, and then compressing or encapsulating the coated particles to yield the dosage form.

VII. Product-by-Process

The present disclosure also relates to stable solid pharmaceutical dosage forms that are prepared in accordance with one of the above-described methods and comprise about 0.25 mg to about 1.25 mg of atrasentan, or pharmaceutically acceptable salt thereof, as described in any of the embodiments of the disclosure. In one aspect, the dosage form is prepared in accordance with the above-described method in which the atrasentan, or pharmaceutically acceptable salt thereof, is pre-treated with the HPMC. In another aspect, the dosage form is prepared in accordance with the above-described method in which an atrasentan-coated tablet is prepared.

A. Product-by-Process: Pre-Treatment of Atrasentan with HPMC

In one embodiment, the present disclosure relates to a stable solid pharmaceutical dosage form comprising about 0.25 mg to about 1.25 mg of atrasentan, or a pharmaceutically acceptable salt thereof, as described in any of the embodiments of the disclosure wherein:

the dosage form comprises a pharmaceutically acceptable polymeric binder selected from the group consisting of hydroxymethylpropylcellulose, hydroxyethylpropylcellulose, and hydroxypropylcellulose;

the dosage form is prepared by:

(a) combining at least a portion of the atrasentan, or a pharmaceutically acceptable salt thereof, with at least a portion of the polymeric binder to form a first mixture;

(b) blending the first mixture with the diluent to form a second mixture; and (c) encapsulating or tableting the second mixture to yield the dosage form; and degradation of atrasentan in the dosage form is less than degradation of atrasentan in an otherwise identical dosage form lacking the polymeric binder when the dosage forms are stored for a storage period of six months at about 40° C. and about 75% relative humidity.

In one aspect, the dosage form further comprises a pharmaceutically acceptable anti-oxidant, and degradation of atrasentan in the dosage form is less than degradation of atrasentan in an otherwise identical dosage form lacking the anti-oxidant and the polymeric binder when the dosage forms are stored for a storage period of six months at about 40° C. and about 75% relative humidity.

In another embodiment, the polymeric binder is hydroxypropyl methylcellulose. In one aspect, the polymeric binder is hydroxypropylethylcellulose. In another aspect, the polymeric binder is hydroxypropylcellulose. In another aspect, the weight percent of the polymeric binder in the dosage form is from about 1.0 weight percent to about 10.0 weight percent. In another aspect, the first mixture is a liquid mixture. In another aspect, the first mixture is a liquid mixture, the blending step comprises wet granulation, and the first mixture is used as a granulating agent. In another aspect, the first mixture is a dry mixture. In another aspect, the first mixture is a dry mixture and the first mixture is compressed before it is blended with the diluent.

Where the first mixture is a liquid mixture, the liquid mixture comprises a pharmaceutically acceptable liquid such as water. In one aspect, the first mixture is an aqueous mixture. In another aspect, the first mixture is an aqueous suspension of atrasentan, or a pharmaceutically acceptable salt thereof. In another aspect, the first mixture is an aqueous solution of atrasentan, or a pharmaceutically acceptable salt thereof. In another aspect, the first mixture is an aqueous mixture, the blending step comprises wet granulation, and the first mixture is used as a granulating agent. In another aspect of embodiments employing wet granulation, a first portion of the polymeric binder is combined with the atrasentan, or a pharmaceutically acceptable salt thereof, to prepare the first mixture and a second portion of the polymeric binder is added to the granulation bowl used to prepare the second mixture.

In one embodiment, the liquid mixture has a viscosity that is sufficient to maintain the atrasentan, or pharmaceutically acceptable salt thereof, in suspension.

In another embodiment, the atrasentan, or pharmaceutically acceptable salt thereof, is dissolved in the liquid mixture.

In another embodiment, the weight percent of the polymeric binder in the liquid mixture is from about 0.5 weight percent to about 15.0 weight percent. In another aspect, the weight percent of the polymeric binder is from about 0.5 weight percent to about 12.0 weight percent. In another aspect, the weight percent of the polymeric binder is from about 0.5 weight percent to about 10.0 weight percent.

In another embodiment, the weight percent of the atrasentan, or pharmaceutically acceptable salt thereof, in the liquid mixture is from about 2.0 weight percent to about 12.0 weight percent. In another aspect, the weight percent of atrasentan, or pharmaceutically acceptable salt thereof, is from about 3.0 weight percent to about 10.0 weight percent. In another aspect, the weight percent of atrasentan, or pharmaceutically acceptable salt thereof, is from about 4.0 weight percent to about 8.0 weight percent.

In another embodiment, the weight to weight ratio of the polymeric binder to atrasentan, or a pharmaceutically acceptable salt thereof, in the liquid mixture is from about 5:1 to about 1:5. In one aspect, the weight to weight ratio of the polymeric binder to atrasentan, or a pharmaceutically acceptable salt thereof, is from about 3.5:1 to about 1:3.5. In another aspect, the weight to weight ratio of the polymeric binder to atrasentan, or a pharmaceutically acceptable salt thereof, in the first mixture is from about 1:2 to about 2:1.

In another embodiment, at least two of the following conditions are satisfied: (a) the weight percent of the polymeric binder in the liquid mixture is from about 0.5 weight percent to about 15.0 weight percent; (b) the weight percent of atrasentan, or pharmaceutically acceptable salt thereof, in the first mixture is from about 2.0 weight percent to about 12.0 weight percent; and/or (c) the weight to weight ratio of the polymeric binder to atrasentan, or a pharmaceutically acceptable salt thereof, in the first mixture is from about 5:1 to about 1:5 on an atrasentan free base equivalent weight basis. In one aspect, at least two of the following conditions are satisfied: (a) the weight percent of the polymeric binder in the liquid mixture is from about 0.5 weight percent to about 12.0 weight percent; (b) the weight percent of atrasentan, or pharmaceutically acceptable salt thereof, in the first mixture is from about 3.0 weight percent to about 10.0 weight percent; and/or (c) the weight to weight ratio of the polymeric binder to atrasentan, or a pharmaceutically acceptable salt thereof, in the first mixture is from about 3.5:1 to about 1:3.5 on an atrasentan free base equivalent weight basis. In another aspect, at least two of the following conditions are satisfied: (a) the weight percent of the polymeric binder in the liquid mixture is from about 0.5 weight percent to about 10.0 weight percent; (b) the weight percent of atrasentan, or pharmaceutically acceptable salt thereof, in the first mixture is from about 4.0 weight percent to about 8.0 weight percent; and/or (c) the weight to weight ratio of the polymeric binder to atrasentan, or a pharmaceutically acceptable salt thereof, in the first mixture is from about 1:2 to about 2:1 on an atrasentan free base equivalent weight basis.

In each of the above-discussed methods, the second mixture additionally may comprise an anti-oxidant, a disintegrant, a glidant, and/or a lubricant. In one aspect, the second mixture comprises an anti-oxidant. In another aspect, the second mixture comprises a disintegrant. In another aspect, the second mixture comprises a glidant. In another aspect, the second mixture comprises a lubricant. In another aspect, the second mixture comprises an anti-oxidant, a disintegrant, a glidant, and a lubricant. In another aspect, the anti-oxidant is L-cysteine, or a pharmaceutically acceptable salt or ester thereof. In another aspect, the second mixture comprises L-cysteine, or a pharmaceutically acceptable salt or ester thereof, a disintegrant, a glidant, and a lubricant.

B. Product-by-Process: Atrasentan-Coated Tablet

In one embodiment, the present disclosure relates to a stable solid pharmaceutical dosage form comprising about 0.25 mg to about 1.25 mg of atrasentan, or a pharmaceutically acceptable salt thereof, as described in any of the embodiments of the disclosure wherein: the dosage form is prepared by:

(a) combining atrasentan, or a pharmaceutically acceptable salt thereof, and a pharmaceutically acceptable polymer selected from the group consisting of hydroxymethylpropylcellulose, hydroxyethylpropylcellulose, and hydroxypropylcellulose to form a coating mixture; and (b) applying the coating mixture to the surface of a tablet core comprising a pharmaceutically acceptable diluent to yield the dosage form; and degradation of atrasentan in the dosage form is less than degradation of atrasentan in an otherwise identical dosage form lacking the polymer when the dosage forms are stored for a storage period of six months at about 40° C. and about 75% relative humidity.

In another embodiment, one or both of the following conditions are satisfied: (a) the weight percent of atrasentan, or pharmaceutically acceptable salt thereof, in the dosage form is from about 0.05 weight percent to about 2.0 weight percent on an atrasentan free base equivalent weight basis; and/or (b) the weight percent of the polymer in the dosage form is from about 0.5 weight percent to about 15.0 weight percent. In another aspect, the polymer is hydroxypropyl methylcellulose. In another aspect, the polymer is hydroxypropylethylcellulose. In another aspect, the polymer is hydroxypropylcellulose.

In various additional embodiments, the tablet additionally may comprise an anti-oxidant, a disintegrant, a glidant, and/or a lubricant. In one aspect, the tablet comprises an anti-oxidant. In one aspect, the anti-oxidant is L-cysteine, or a pharmaceutically acceptable salt or ester thereof. In one aspect, the tablet comprises a disintegrant. In another aspect, the tablet comprises a glidant. In another aspect, the tablet comprises a lubricant. In another aspect, the tablet comprises an anti-oxidant, a disintegrant, a glidant, and a lubricant.

In an alternative embodiment, the dosage form is prepared in accordance with the above-described method except that step (b) instead involves applying the coating mixture to the surface of particles (e.g., beads, granules, pellets, or the like) comprising a pharmaceutically acceptable diluent, and then compressing or encapsulating the coated particles to yield the dosage form.

VIII. EXAMPLES

Example 1: Analytical Methods

A. Atrasentan and Impurities Content

High-performance liquid chromatography ("HPLC") was used to determine the amount of atrasentan and the amount of impurities (i.e., atrasentan degradation products) contained in the tablets analyzed in the stability testing reported in the following Examples. Although minor changes were made to the HPLC conditions used to determine the amount of atrasentan over the course of stability testing, the changes did not materially affect the measured values. Descriptions of the initial and the modified HPLC conditions employed to generate data reported in the following Examples are provided in Tables 1-A through 1-C. The HPLC conditions used to determine the amount of impurities reported in the following Examples were not modified over the course of stability testing and a description of those HPLC conditions is provided in Table 1-D.

(i) Atrasentan Sample Preparation Procedure (Assay)

(a) 0.35 mg Tablets

Ten tablets are transferred into a 200.0 mL volumetric flask. Approximately 120 mL of the Diluent is added to the flask. Using a mechanical shaker, the flask is shaken for approximately 2 hours. The flask contents are diluted to volume with the Diluent and mixed well. Approximately 20 mL of the resulting solution is filtered through a 0.45-micron nylon filter, sending the initial portion of about 5 mL to waste and collecting about 10 mL for further use.

(b) 0.50 mg Tablets

Ten tablets are transferred into a 250.0 mL volumetric flask. Approximately 150 mL of the Diluent is added to the flask. Using a mechanical shaker, the flask is shaken for approximately 2 hours. The flask contents are diluted to volume with the Diluent and mixed well. Approximately 20 mL of the resulting solution is filtered through a 0.45-micron nylon filter, sending the initial portion of about 5 mL to waste and collecting about 10 mL for further use.

(c) 0.75 mg Tablets

Seven tablets are transferred into a 250.0 mL volumetric flask. Approximately 150 mL of the Diluent is added to the flask. Using a mechanical shaker, the flask is shaken for approximately 2 hours. The flask contents are diluted to volume with the Diluent and mixed well. Approximately 20 mL of the resulting solution is filtered through a 0.45-micron nylon filter, sending the initial portion of about 5 mL to waste and collecting about 10 mL for further use.

(ii) Atrasentan Sample Preparation Procedure (Content Uniformity)

(a) 0.35 mg Tablets

One tablet is transferred into a 20.0 mL volumetric flask. Approximately 12 mL of the Diluent is added to the flask. Using a mechanical shaker, the flask is shaken for approximately 2 hours. The flask contents are diluted to volume with the Diluent and mixed well. Approximately 20 mL of the resulting solution is filtered through a 0.45-micron nylon filter, sending the initial portion of about 5 mL to waste and collecting about 10 mL for further use.

(b) 0.50 mg Tablets

One tablet is transferred into a 25.0 mL volumetric flask. Approximately 15 mL of the Diluent is added to the flask. Using a mechanical shaker, the flask is shaken for approximately 2 hours. The flask contents are diluted to volume with the Diluent and mixed well. Approximately 20 mL of the resulting solution is filtered through a 0.45-micron nylon filter, sending the initial portion of about 5 mL to waste and collecting about 10 mL for further use.

(c) 0.75 mg Tablets

One tablet is transferred into a 50.0 mL volumetric flask. Approximately 30 mL of the Diluent is added to the flask. Using a mechanical shaker, the flask is shaken for approximately 2 hours. The flask contents are diluted to volume with the Diluent and mixed well. Approximately 20 mL of the resulting solution is filtered through a 0.45-micron nylon filter, sending the initial portion of about 5 mL to waste and collecting about 10 mL for further use.

(iii) Impurities Sample Preparation Procedure (a) 0.35 mg Tablets

Fourteen tablets are transferred into a 50-mL volumetric flask. Approximately 25 mL of the High Organic Diluent is added to the flask. Using a mechanical shaker, the flask is shaken for approximately 120 minutes. The flask contents are diluted to volume using the High Organic Diluent and mixed well. A portion of the resulting solution is filtered through a 0.45-micron Nylon membrane, sending the initial portion of about 5 mL to waste. A 2.0 mL portion of the filtered solution is diluted to a volume of 10.0 mL using a 10 mM Formate buffer and mixed well.

(b) 0.50 mg Tablets

Ten tablets are transferred into a 50-mL volumetric flask. Approximately 25 mL of the High Organic Diluent is added to the flask. Using a mechanical shaker, the flask is shaken for approximately 120 minutes. The flask contents are diluted to volume using the High Organic Diluent and mixed well. A portion of the resulting solution is filtered through a 0.45-micron Nylon membrane, sending the initial portion of about 5 mL to waste. A 2.0 mL portion of the filtered solution is diluted to a volume of 10.0 mL using a 10 mM Formate buffer and mixed well.

(c) 0.75 mg Tablets

Six tablets are transferred into a 50-mL volumetric flask. Approximately 25 mL of the High Organic Diluent is added to the flask. Using a mechanical shaker, the flask is shaken for approximately 120 minutes. The flask contents are diluted to volume using the High Organic Diluent and mixed well. A portion of the resulting solution is filtered through a 0.45-micron Nylon membrane, sending the initial portion of about 5 mL to waste. A 2.0 mL portion of the filtered solution is diluted to a volume of 10.0 mL using a 10 mM Formate buffer and mixed well.

(iv) HPLC Conditions

TABLE 1-A

Atrasentan Assay HPLC Conditions (Version 1)

| PARAMETER | CONDITIONS | | |
|---|---|---|---|
| Technique | HPLC | | |
| Column | $C_{18}$, 2.6 micron, 150 × 3.0 mm, 35° C. | | |
| Mobile Phase A | 95/5 10 mM Ammonium Formate Buffer pH 3.2/Acetonitrile | | |
| Mobile Phase B | 85/15 Acetonitrile/50 mM Ammonium Formate Buffer pH 3.2 | | |
| | Gradient | | |
| | Time (min) | % A | % B |
| Elution | 0 | 60 | 40 |
| | 25 | 60 | 40 |
| | 25.1 | 10 | 90 |
| | 31.0 | 10 | 90 |
| | 31.1 | 60 | 40 |
| | 40 | 60 | 40 |
| Flow Rate | Approximately 0.5 mL/minute | | |
| Injection volume | 10 μL | | |
| Detection | UV at 234 nm | | |
| Diluent | 10 mM Ammonium Formate Buffer, pH 3.2:Acetonitrile (25:75) | | |
| Solution Concentrations | | | |
| Standard | Approximately 19 μg atrasentan*/mL in Diluent | | |
| Sample: Assay and Content Uniformity | Approximately 20 μg atrasentan*/mL in Diluent (Blend) Approximately 20 μg atrasentan*/mL in Diluent (0.50 mg Tablet) Approximately 30 μg atrasentan*/mL in Diluent (0.75 mg Tablet) | | |

*Free base equivalent weight

TABLE 1-B

Atrasentan Assay HPLC Conditions (Version 2)

| PARAMETER | CONDITIONS |
|---|---|
| Technique | HPLC |
| Column | $C_{18}$, 2.6 micron, 150 × 3.0 mm, 35° C. |
| Mobile Phase A | 63/37 8.7 mM Ammonium Formate Buffer pH 3.2/Acetonitrile |
| Mobile Phase B | 77/23 Acetonitrile/7.7 mM Ammonium Formate Buffer pH 3.2 |

Gradient

| | Time (min) | % A | % B |
|---|---|---|---|
| Elution | 0 | 100 | 0 |
| | 25 | 100 | 0 |
| | 25.1 | 0 | 100 |
| | 31.0 | 0 | 100 |
| | 31.1 | 100 | 0 |
| | 40 | 100 | 0 |

| PARAMETER | CONDITIONS |
|---|---|
| Flow Rate | Approximately 0.5 mL/minute |
| Injection volume | 10 μL |
| Detection | UV at 234 nm |
| Diluent | 10 mM Ammonium Formate Buffer, pH 3.2:Acetonitrile (25:75) |

Solution Concentrations

| | |
|---|---|
| Standard | Approximately 19 μg atrasentan*/mL in Diluent |
| Sample: Assay | Approximately 20 μg atrasentan*/mL in Diluent (Blend) |
| | Approximately 18 μg atrasentan*/mL in Diluent (0.35 mg Tablet) |
| | Approximately 20 μg atrasentan*/mL in Diluent (0.50 mg Tablet) |
| | Approximately 21 μg atrasentan*/mL in Diluent (0.75 mg Tablet) |
| Sample: Content Uniformity | Approximately 18 μg atrasentan*/mL in Diluent (0.35 mg Tablet) |
| | Approximately 20 μg atrasentan*/mL in Diluent (0.50 mg Tablet) |
| | Approximately 15 μg atrasentan*/mL in Diluent (0.75 mg Tablet) |

*Free base equivalent weight

TABLE 1-C

Atrasentan Assay HPLC Conditions (Version 3)

| PARAMETER | CONDITIONS |
|---|---|
| Technique | HPLC |
| Column | $C_{18}$, 2.6 micron, 150 × 3.0 mm, 35° C. |
| Mobile Phase A | 60/40 10 mM Ammonium Formate Buffer pH 3.2/Acetonitrile |
| Elution | Isocratic |
| Flow Rate | Approximately 0.5 mL/minute |
| Injection volume | 10 μL |
| Detection | UV at 234 nm |
| Diluent | 10 mM Ammonium Formate Buffer, pH 3.2:Acetonitrile (25:75) |

Solution Concentrations

| | |
|---|---|
| Standard | Approximately 19 μg atrasentan*/mL in Diluent |
| Sample: Assay | Approximately 20 μg atrasentan*/mL in Diluent (Blend) |
| | Approximately 18 μg atrasentan*/mL in Diluent (0.35 mg Tablet) |
| | Approximately 20 atrasentan*/mL in Diluent (0.50 mg Tablet) |
| | Approximately 21 μg atrasentan*/mL in Diluent (0.75 mg Tablet) |
| Sample: Content | Approximately 18 μg atrasentan*/mL in Diluent (0.35 mg Tablet) |

TABLE 1-C-continued

Atrasentan Assay HPLC Conditions (Version 3)

| PARAMETER | CONDITIONS |
|---|---|
| Uniformity | Approximately 20 μg atrasentan*/mL in Diluent (0.50 mg Tablet) |
| | Approximately 15 μg atrasentan*/mL in Diluent (0.75 mg Tablet) |

*Free base equivalent weight

TABLE 1-D

Impurities Assay HPLC Conditions

| PARAMETER | CONDITIONS |
|---|---|
| Technique | HPLC |
| Column | $C_{18}$, 2.6 micron, 150 × 3.0 mm, 35° C. |
| Mobile Phase A | 10 mM Ammonium Formate Buffer, pH 3.2:Acetonitrile (95:5) |
| Mobile Phase B | 50 mM Ammonium Formate Buffer, pH 3.2:Acetonitrile (15:85) |

| | Time (min) | % A | % B |
|---|---|---|---|
| Gradient Profile | 0 | 95 | 5 |
| | 22 | 60 | 40 |
| | 29 | 60 | 40 |
| | 55 | 5 | 95 |
| | 60 | 5 | 95 |
| | 60.1 | 95 | 5 |
| | 70 | 95 | 5 |

| PARAMETER | CONDITIONS |
|---|---|
| Flow Rate | Approximately 0.5 mL/minute |
| Injection volume | 75 μL |
| Detection | UV at 234 nm |
| Practical Detection Limit | 0.05% |
| Diluent | |
| High Organic | 10 mM Ammonium Formate Buffer, pH 3.2:Acetonitrile (25:75) |
| Low Organic | 10 mM Ammonium Formate Buffer, pH 3.2:Acetonitrile (85:15) |

Solution Concentrations

| | |
|---|---|
| Practical Detection Limit | Approximately 0.009 μg atrasentan*/mL in Low Organic Diluent |
| Standard | Approximately 0.09 μg atrasentan*/mL in Low Organic Diluent |
| Sample: Assay | Approximately 20 μg atrasentan*/mL in solution equivalent to Low Organic Diluent (0.50 mg tablets) |
| | Approximately 18 μg atrasentan*/mL mL in solution equivalent to Low Organic Diluent (0.75 mg tablets) |

*Free base equivalent weight

B. Moisture Content

The moisture content data reported in the following Examples were determined using Karl Fisher titration. Further information on the titration is provided in Table 1-E below.

TABLE 1-E

Tablet Moisture Content Method

| PARAMETER | CONDITIONS |
|---|---|
| Technique | Volumetric Karl Fischer |
| Reagent | Hydranal-Composite 5, Fluka |
| Diluent | Methanol |
| Sample Size | 1 gram composite of 12 tablets |

C. Dissolution Profile

The tablet dissolution profile data reported in the following Examples were generated using a USP Dissolution Apparatus 2 and HPLC as the analytical method. Further information on the dissolution testing and HPLC analytical method is provided in Table 1-F below.

TABLE 1-F

Tablet Dissolution Profile Method

| PARAMETER | CONDITIONS |
|---|---|
| Technique | HPLC |
| Column | $C_{18}$, 5 micron, 150 × 4.6 mm, 25° C. |
| Mobile Phase | 50/50 50 mM Phosphate Buffer pH 2.6/Acetonitrile |
| Elution | Isocratic |
| Flow Rate | Approximately 1.0 mL/minute |
| Injection volume | 100 µL |
| Detection | UV at 234 nm |
| Apparatus | USP Dissolution Apparatus 2 and Syringe-driven fraction collector |
| Medium | 900 mL of 0.01N HCl |
| Temperature | 37° C. |
| RPM | 50 RPM |
| Sampling Times | 15, 30, 45, 60 Minutes |
| Diluent | Samples Diluted 1:1 with mobile phase Solution Concentrations |
| Standard | Approximately 0.21 µg atrasentan*/mL in Diluent |

*Free base equivalent weight

Example 2: Phase IIb Tablet Stability

Atrasentan dosage forms having the compositions shown in Table 2-A (0.35 mg tablet), Table 2-B (0.50 mg tablet), and Table 2-C (0.75 mg tablet) below were prepared and used in Phase IIb clinical trials to evaluate the safety and efficacy of atrasentan in treating subjects with diabetic nephropathy. The tablets were prepared using a wet granulation process and were compressed into round tablets having a core weight of 120 mg and a diameter of 6.5 mm.

TABLE 2-A

Phase IIb Tablet (0.35 mg)

TABLET CORE COMPOSITION

| INGREDIENT | WEIGHT/WEIGHT % | mg/TABLET |
|---|---|---|
| Atrasentan Monohydrochloride | 0.31 | $0.37^a$ |
| Lactose Monohydrate (Regular) | 91.19 | 109.4 |
| Hypromellose E5 (Premium LV) | 3.00 | 3.6 |
| Crospovidone (POLYPLASDONE ™ XL) | 3.50 | 4.2 |
| Silicon Dioxide (SYLOID ®) | 0.50 | 0.6 |
| Glyceryl Behenate (COMPRITOL ®) | 1.50 | 1.8 |
| Purified water$^b$ | n/a | n/a |
| Total | 100% | 120 mg |

TABLE 2-A-continued

Phase IIb Tablet (0.35 mg)

FILM COATED TABLET COMPOSITION

| INGREDIENT | WEIGHT/WEIGHT %$^c$ | mg/TABLET$^d$ |
|---|---|---|
| PEG1450 | 3 | 0.1 |
| Hypromellose E5 (Premium LV) | 97 | 3.5 |
| Purified Water | N/a | n/a |

$^a$Atrasentan monohydrochloride salt factor = 1.07 (i.e., 0.35 mg free base × 1.07 = 0.37 mg salt).
$^b$Granulation suspension medium. Less than 2% present in final product.
$^c$Based on an aqueous solution of 10% solids.
$^d$Based on a 120 mg tablet weight with a coating weight gain of 3%.

TABLE 2-B

Phase IIb Tablet (0.50 mg)

TABLET CORE COMPOSITION

| INGREDIENT | WEIGHT/WEIGHT % | mg/TABLET |
|---|---|---|
| Atrasentan Monohydrochloride | 0.4460 | $0.5350^a$ |
| Lactose Monohydrate (Regular) | 91.05 | 109.3 |
| Hypromellose E5 (Premium LV) | 3.000 | 3.600 |
| Crospovidone (POLYPLASDONE ™ XL) | 3.500 | 4.200 |
| Silicon Dioxide (SYLOID ® 244FP) | 0.500 | 0.600 |
| Glyceryl Behenate (COMPRITOL ®) | 1.500 | 1.800 |
| Purified water$^b$ | N/A | N/A |
| Total | 100% | 120.0 mg |

FILM COATED TABLET COMPOSITION

| INGREDIENT | WEIGHT/WEIGHT %$^c$ | mg/TABLET$^d$ |
|---|---|---|
| PEG1450 | 3 | 0.1080 |
| Hypromellose E5 (Premium LV) | 97 | 3.492 |
| Purified water | N/A | N/A |
| Total | 100% | 123.6 mg |

$^a$Atrasentan monohydrochloride salt factor = 1.07 (i.e., 0.50 mg free base × 1.07 = 0.5350 mg salt).
$^b$Granulation suspension medium. Less than 2% present in final product.
$^c$Based on an aqueous solution of 10% solids.
$^d$Based on a 120 mg tablet weight with a coating weight gain of 3%.

TABLE 2-C

Phase IIb Tablet (0.75 mg)

TABLET CORE COMPOSITION

| INGREDIENT | WEIGHT/WEIGHT % | mg/TABLET |
|---|---|---|
| Atrasentan Monohydrochloride | 0.6690 | $0.8025^a$ |
| Lactose Monohydrate (Regular) | 90.83 | 109.0 |
| Hypromellose E5 (Premium LV) | 3.000 | 3.600 |
| Crospovidone (POLYPLASDONE ™ XL) | 3.500 | 4.200 |
| Silicon Dioxide (SYLOID ® 244FP) | 0.500 | 0.600 |

TABLE 2-C-continued

Phase IIb Tablet (0.75 mg)

| | | |
|---|---|---|
| Glyceryl Behenate (COMPRITOL ®) | 1.500 | 1.800 |
| Purified water[b] | N/A | N/A |
| Total | 100% | 120.0 mg |

FILM COATED TABLET COMPOSITION

| INGREDIENT | WEIGHT/WEIGHT %[c] | mg/TABLET[d] |
|---|---|---|
| PEG1450 | 3 | 0.1080 |
| Hypromellose E5 (Premium LV) | 97 | 3.492 |
| Purified water | N/A | N/A |
| Total | 100% | 123.6 mg |

[a]Atrasentan monohydrochloride salt factor = 1.07 (i.e., 0.75 mg free base × 1.07 = 0.8025 mg salt).
[b]Granulation suspension medium. Less than 2% present in final product.
[c]Based on an aqueous solution of 10% solids.
[d]Based on a 120 mg tablet weight with a coating weight gain of 3%.

The 0.35 mg, 0.50 mg, and 0.75 mg Phase IIb tablets described above were tested for stability under one or more of the following storage conditions:

(a) Storage at 40° C. and 75% relative humidity with tablet stability assessed at the end of 1, 3, and 6 months (accelerated stability testing protocol);

(b) Storage at 30° C. and 65% relative humidity with tablet stability assessed at the end of 12 months (intermediate-term stability testing protocol); and (c) Storage at 25° C. and 60% relative humidity with tablet stability assessed at the end of 1, 3, 6, 9, 12, 18, and 24 months (long-term storage stability testing protocol).

In each stability test, 20 tablets were placed in a high-density polyethylene ("HDPE") bottle containing a desiccant and the HDPE bottle was induction-sealed with a polypropylene cap. Parameters measured for the tablets at each time interval included atrasentan content relative to labeled dose (assay), degradation product content, water content, and dissolution profile. The results are reported below in Tables 2-D through 2-K. The "Assay" data reported represent the weight percent of atrasentan measured relative to the labeled dose (i.e., either 0.35 mg, 0.50 mg, or 0.75 mg). The "Degradation Products" data reported represent the weight percent of impurities measured relative to the labeled dose (i.e., either 0.35 mg, 0.50 mg, or 0.75 mg). All data reported represent single values from single runs with the following exceptions: (a) the initial atrasentan content value reported is a mean value where n=2, and (b) the dissolution values reported are mean values where n=6.

TABLE 2-D

Storage Stability Under Accelerated Conditions (0.35 mg Phase IIb Tablet)

| Test | SPECIFICATION[1] Acceptance Criteria | INITIAL | 1 MONTH | 3 MONTHS | MONTHS |
|---|---|---|---|---|---|
| Description | Physical Inspection | Meets requirements | Meets requirements | Meets requirements | Meets requirements |
| | Appearance | Tablet | Tablet | Tablet | Tablet |
| | Marking | Unmarked | Unmarked | Unmarked | Unmarked |
| | Shape | Round | Round | Round | Round |
| | Color | White | Off-white | Off-white | Off-white |
| | Coating | Coated | Coated | Coated | Coated |
| Assay | Assay | 101.4/102.1 | 101.9 | 100.6 | 100.0 |
| Water Content | Moisture | 4.8 | 4.9 | 4.8 | 4.6 |
| Dissolution | 15 min: Mean | 95 | 94 | 93 | 96 |
| | 30 min: Mean | 100 | 100 | 99 | 100 |
| | 45 min: Mean | 100 | 100 | 100 | 100 |
| | 60 min: Mean | 100 | 101 | 99 | 100 |
| Degradation Products | Total % Reported | 0.11 | 0.10 | 0.34 | 0.33 |

[1]Note: Tablets stored in 3 oz HDPE bottle containing 1.1 g silica desiccant and having induction sealed cap.

TABLE 2-E

Storage Stability Under Long-Term Conditions (0.35 mg Phase IIb Tablet)

| Test | SPECIFICATION[1] Acceptance Criteria | INITIAL | 1 MONTH | 3 MONTHS | 6 MONTHS |
|---|---|---|---|---|---|
| Description | Physical Inspection | Meets requirements | Meets requirements | Meets requirements | Meets requirements |
| | Appearance | Tablet | Tablet | Tablet | Tablet |
| | Marking | Unmarked | Unmarked | Unmarked | Unmarked |
| | Shape | Round | Round | Round | Round |
| | Color | White | Off-white | Off-white | Off-white |
| | Coating | Coated | Coated | Coated | Coated |
| Assay | Assay | 101.4/102.1 | 101.4 | 100.8 | 100.2 |
| Water Content | Moisture | 4.8 | 4.7 | 4.6 | 4.4 |

TABLE 2-E-continued

Storage Stability Under Long-Term Conditions (0.35 mg Phase IIb Tablet)

SPECIFICATION[1]

| Test | Acceptance Criteria | INITIAL | 1 MONTH | 3 MONTHS | 6 MONTHS |
|---|---|---|---|---|---|
| Dissolution | 15 min: Mean | 95 | 99 | 96 | 99 |
|  | 30 min: Mean | 100 | 101 | 101 | 102 |
|  | 45 min: Mean | 100 | 101 | 100 | 101 |
|  | 60 min: Mean | 100 | 100 | 101 | 101 |
| Degradation Products | Total % Reported | 0.11 | 0.13 | 0.19 | 0.00 |

TABLE 2-E (Continued): Storage Stability Under Long-Term Conditions (0.35 mg Phase IIb Tablet)

SPECIFICATION[1]

| Test | Acceptance Criteria | 9 MONTH | 12 MONTHS | 18 MONTHS |
|---|---|---|---|---|
| Description | Physical Inspection Appearance Marking Shape Color Coating | Meets requirements Tablet Unmarked Round Off-white Coated | Meets requirements Tablet Unmarked Round Off-white Coated | Meets requirements Tablet Unmarked Round Off-white Coated |
| Assay | Assay | 100.7 | 100.6 | 100.1 |
| Water Content | Moisture | 4.5 | 4.9 | 4.7 |

TABLE 2-E-continued (Continued): Storage Stability Under Long-Term Conditions (0.35 mg Phase IIb Tablet)

SPECIFICATION[1]

| Test | Acceptance Criteria | 9 MONTH | 12 MONTHS | 18 MONTHS |
|---|---|---|---|---|
| Dissolution | 15 min: Mean | 96 | 96 | 91 |
|  | 30 min: Mean | 101 | 102 | 95 |
|  | 45 min: Mean | 101 | 103 | 98 |
|  | 60 min: Mean | 101 | 102 | 98 |
| Degradation Products | Total % Reported | 0.10 | 0.21 | 0.0 |

[1]Note: Tablets stored in 3 oz HDPE bottle containing 1.1 g silica desiccant and having induction sealed cap.

TABLE 2-F

Storage Stability Under Accelerated Conditions (0.50 mg Phase IIb Tablet)

SPECIFICATION[1]

| Test | Acceptance Criteria | INITIAL | 1 MONTH | 3 MONTHS | 6 MONTHS |
|---|---|---|---|---|---|
| Description | Appearance Marking Shape Color Coating | Tablet Unmarked Round Off-white Coated | Tablet Unmarked Round Off-white Coated | Tablet Unmarked Round White Coated | Tablet Unmarked Round Off-white Coated |
| Assay | Assay Mean | 98.6/99.0 98.8 | 97.6 — | 96.7 — | 93.6 — |
| Water Content | Moisture | 4.8 | 5.1 | 5.0 | 5.3 |
| Dissolution | 15 min: Mean | 79 | 67 | 62 | 54 |
|  | 30 min: Mean | 93 | 92 | 89 | 81 |
|  | 45 min: Mean | 95 | 97 | 93 | 84 |
|  | 60 min: Mean | 96 | 98 | 94 | 85 |
| Degradation Products | Total % Reported | 0 | 0.12 | 1.3 | 1.4 |

[1]Note: Tablets stored in 5 oz HDPE bottle containing 2 g clay desiccant and having induction sealed cap.

TABLE 2-G

Storage Stability Under Intermediate Conditions (0.50 mg Phase IIb Tablet)

SPECIFICATION[1]

| Test | Acceptance Criteria | INITIAL | 12 MONTHS | 15 MONTHS | 18 MONTHS |
|---|---|---|---|---|---|
| Description | Appearance Marking Shape Color Coating | Tablet Unmarked Round Off-white Coated | Tablet Unmarked Round Off-white Coated | Tablet Unmarked Round Off-white Coated | Tablet Unmarked Round Off-white Coated |

TABLE 2-G-continued

Storage Stablity Under Intermediate Conditions (0.50 mg Phase IIb Tablet)

SPECIFICATION[1]

| Test | Acceptance Criteria | INITIAL | 12 MONTHS | 15 MONTHS | 18 MONTHS |
|---|---|---|---|---|---|
| Assay | Assay | 98.6/99.0 | 98.4 | 97.3 | 96.8 |
| | Mean | 98.8 | — | — | — |
| Water Content | Moisture | 4.8 | 4.8 | 5.1 | 5.1 |
| Dissolution | 15 min: Mean | 79 | 78 | 76 | 80 |
| | 30 min: Mean | 93 | 93 | 91 | 87 |
| | 45 min: Mean | 95 | 95 | 93 | 93 |
| | 60 min: Mean | 96 | 96 | 95 | 93 |
| Degradation Products | Total % Reported | 0 | 0.50 | 0.66 | 1.1 |

[1]Note: Tablets stored in 5 oz HDPE bottle containing 2 g clay desiccant and having induction sealed cap.

TABLE 2-H

Storage Stability Under Long-Term Conditions (0.50 mg Phase IIb Tablet)

SPECIFICATION[1]

| Test | Acceptance Criteria | INITIAL | 1 MONTH | 3 MONTHS | 6 MONTHS |
|---|---|---|---|---|---|
| Description | Appearance | Tablet | Tablet | Tablet | Tablet |
| | Marking | Unmarked | Unmarked | Unmarked | Unmarked |
| | Shape | Round | Round | Round | Round |
| | Color | Off-white | Off-white | White | Off-white |
| | Coating | Coated | Coated | Coated | Coated |
| Assay | Assay | 98.6/99.0 | 98.1 | 98.2 | 99.5 |
| | Mean | 98.8 | — | — | — |
| Water Content | Moisture | 4.8 | 4.7 | 5.0 | 5.1 |
| Dissolution | 15 min: Mean | 79 | 82 | 83 | 75 |
| | 30 min: Mean | 93 | 94 | 95 | 92 |
| | 45 min: Mean | 95 | 95 | 97 | 94 |
| | 60 min: Mean | 96 | 97 | 98 | 94 |
| Degradation Products | Total % Reported | 0 | 0 | 0.69 | 0.22 |

SPECIFICATION[1]

| Test | | 9 MONTHS | 12 MONTHS | 18 MONTHS | 24 MONTHS |
|---|---|---|---|---|---|
| Description | Appearance | Tablet | Tablet | Tablet | Tablet |
| | Marking | Unmarked | Unmarked | Unmarked | Unmarked |
| | Shape | Round | Round | Round | Round |
| | Color | Off-white | Off-white | Off-white | Off-white |
| | Coating | Coated | Coated | Coated | Coated |
| Assay | Assay | 100.5 | 99.1 | 98.2 | 95.3 |
| | Mean | — | — | — | — |
| Water Content | Moisture | 4.7 | 4.7 | 4.9 | 5.0 |
| Dissolution | 15 min: Mean | 74 | 77 | 79 | 76 |
| | 30 min: Mean | 95 | 93 | 92 | 91 |
| | 45 min: Mean | 98 | 95 | 96 | 93 |
| | 60 min: Mean | 99 | 95 | 97 | 95 |
| Degradation Products | Total % Reported | 0.13 | 0.13 | 0.21 | 1.1 |

SPECIFICATION[1]

| Test | | 30 MONTHS | 36 MONTHS |
|---|---|---|---|
| Description | Appearance | Tablet | Tablet |
| | Marking | Unmarked | Unmarked |
| | Shape | Round | Round |
| | Color | Off-white | Off-White |
| | Coating | Coated | Coated |
| Assay | Assay | 98.8 | 96.3 |
| | Mean | — | — |
| Water Content | Moisture | 5.1 | 5.1 |
| Dissolution | 15 min: Mean | 82 | 83 |
| | 30 min: Mean | 93 | 91 |
| | 45 min: Mean | 94 | 93 |
| | 60 min: Mean | 96 | 95 |

TABLE 2-H-continued

Storage Stability Under Long-Term Conditions (0.50 mg Phase IIb Tablet)

| | | | |
|---|---|---|---|
| Degradation Products | Total % Reported | 0.91 | 0.85 |

[1]Note: Tablets stored in 5 oz HDPE bottle containing 2 g clay desiccant and having induction sealed cap.

TABLE 2-I

Storage Stability Under Accelerated Conditions (0.75 mg Phase IIb Tablet)

Specification

| Test | Acceptance Criteria | Initial | 1 Months | 3 Months | 6 Months |
|---|---|---|---|---|---|
| Description | Appearance | Tablet | Tablet | Tablet | Tablet |
| | Marking | Unmarked | Unmarked | Unmarked | Unmarked |
| | Shape | Round | Round | Round | Round |
| | Color | Off-white | Off-white | Off-white | White |
| | Coating | Coated | Coated | Coated | Coated |
| Assay | Assay | 100.9/102.7 | 100.2 | 97.9 | 96.4 |
| | Mean | 101.8 | — | — | — |
| Water Content | Moisture | 4.9 | 4.5 | 4.8 | 5.3 |
| Dissolution | 15 min: Mean | 72 | 50 | 40 | 47 |
| | 30 min: Mean | 96 | 93 | 84 | 84 |
| | 45 min: Mean | 96 | 98 | 92 | 91 |
| | 60 min: Mean | 97 | 100 | 93 | 93 |
| Degradation Products | Total % Reported | 0.00 | 0 | 0.51 | 1.8 |

TABLE 2-J

Storage Stability Under Intermediate Conditions (0.75 mg Phase IIb Tablet)

SPECIFICATION[1]

| Test | Acceptance Criteria | INITIAL | 12 MONTHS |
|---|---|---|---|
| Description | Appearance | Tablet | Tablet |
| | Marking | Unmarked | Unmarked |
| | Shape | Round | Round |
| | Color | Off-white | White |
| | Coating | Coated | Coated |
| Assay | Assay | 100.9/102.7 | 99.2 |
| | Mean | 101.8 | — |
| Water Content | Moisture | 4.9 | 4.8 |
| Dissolution | 15 min: Mean | 72 | 61 |
| | 30 min: Mean | 96 | 92 |
| | 45 min: Mean | 96 | 96 |
| | 60 min: Mean | 97 | 98 |
| Degradation Products | Total % Reported | 0.00 | 0.46 |

[1]Note: Tablets stored in 5 oz HDPE bottle containing 2 g clay desiccant and having induction sealed cap.

TABLE 2-K

Storage Stability Under Long-Term Conditions (0.75 mg Phase IIb Tablet)

SPECIFICATION[1]

| Test | Acceptance Criteria | INITIAL | 1 MONTH | 3 MONTHS | 6 MONTHS |
|---|---|---|---|---|---|
| Description | Appearance | Tablet | Tablet | Tablet | Tablet |
| | Marking | Unmarked | Unmarked | Unmarked | Unmarked |
| | Shape | Round | Round | Round | Round |
| | Color | Off-white | Off-white | Off-white | White |
| | Coating | Coated | Coated | Coated | Coated |
| Assay | Assay | 100.9/102.7 | 100.4 | 102.5 | 98.9 |
| | Mean | 101.8 | — | — | — |
| Water Content | Moisture | 4.9 | 4.8 | 4.7 | 5.2 |
| Dissolution | 15 min: Mean | 72 | 71 | 67 | 71 |
| | 30 min: Mean | 96 | 96 | 96 | 95 |
| | 45 min: Mean | 96 | 99 | 99 | 98 |
| | 60 min: Mean | 97 | 99 | 100 | 99 |
| Degradation Products | Total % Reported | 0 | 0 | 0.69 | 0.22 |

TABLE 2-K-continued

Storage Stability Under Long-Term Conditions (0.75 mg Phase IIb Tablet)

| Test | SPECIFICATION[1] Acceptance Criteria | 9 MONTHS | 12 MONTHS | 18 MONTHS | 24 MONTHS |
|---|---|---|---|---|---|
| Description | Appearance | Tablet | Tablet | Tablet | Tablet |
| | Marking | Unmarked | Unmarked | Unmarked | Unmarked |
| | Shape | Round | Round | Round | Round |
| | Color | Off-white | White | White | White |
| | Coating | Coated | Coated | Coated | Coated |
| Assay | Assay Mean | 99.7 | 97.4 | 100.9 | 100.3 |
| Water Content | Moisture | 4.7 | 4.8 | 4.8 | 4.5 |
| Dissolution | 15 min: Mean | 71 | 59 | 57 | 60 |
| | 30 min: Mean | 93 | 94 | 95 | 93 |
| | 45 min: Mean | 97 | 98 | 99 | 97 |
| | 60 min: Mean | 97 | 100 | 101 | 99 |
| Degradation Products | Total % Reported | 0.28 | 0 | 0 | 0.24 |

| Test | SPECIFICATION[1] Acceptance Criteria | 30 MONTHS | 36 MONTHS |
|---|---|---|---|
| Description | Appearance | Tablet | Tablet |
| | Marking | Unmarked | Unmarked |
| | Shape | Round | Round |
| | Color | Off-white | White |
| | Coating | Coated | Coated |
| Assay | Assay Mean | 99.4 | 97.9 |
| Water Content | Moisture | 4.7 | 5.2 |
| Dissolution | 15 min: Mean | 70 | 62 |
| | 30 min: Mean | 91 | 91 |
| | 45 min: Mean | 94 | 93 |
| | 60 min: Mean | 95 | 95 |
| Degradation Products | Total % Reported | 0.70 | 0.58 |

[1]Note: Tablets stored in 5 oz HDPE bottle containing 2 g clay desiccant and having induction sealed cap.

In general, the stability data for the Phase IIb tablets indicate an increase in atrasentan degradation products over a six month period at the 40° C. and 75% relative humidity storage conditions for the 0.50 mg and 0.75 mg tablets.

Example 3: Effect of Anti-Oxidant on Stability

A study was conducted to evaluate the effect of an anti-oxidant on preventing atrasentan degradation in a mixture of atrasentan, a disintegrant, and an anti-oxidant. Binary or tertiary mixtures containing atrasentan monohydrochloride, a crospovidone disintegrant (POLYPLASDONE™ XL), and, for the tertiary mixtures, an anti-oxidant (selected from ascorbic acid powder, sodium metabisulfite, and L-cysteine hydrochloride monohydrate) at five different molar ratios of atrasentan to anti-oxidant were prepared. In each case, the weight ratio of disintegrant to atrasentan was held constant at about 9:1. The compositions of the mixtures are shown below in Table 3-A (ascorbic acid powder), Table 3-B (sodium metabisulfite), and Table 3-C (L-cysteine hydrochloride monohydrate). The mixtures were not further formulated (i.e., they were not processed into tablets or capsules) and were maintained as loose blends of the components during storage. To ensure that content non-uniformity for a single mixture did not impact the results, several mixtures were prepared for each molar ratio tested and a different mixture was sampled and tested at each time point.

The mixtures were tested for stability using an accelerated stability testing protocol under which each sample was stored in a 20 mL glass scintillation vial at 80° C. and ambient relative humidity. Stability was assessed at initiation of testing, the end of seven days, and the end of three weeks. Stability testing results are reported below in Tables 3-A through 3-F. All data reported represent single values from single runs (i.e., n=1). The "Impurities" data reported below in Tables 3-A through 3-C represent the percent impurities by HPLC peak area percent. The "Weight % Atrasentan" data reported below in Tables 3-D through 3-F represent the weight percent of atrasentan measured relative to the corresponding weight of atrasentan initially added to the mixture.

TABLE 3-A

L-Ascorbic Acid Mixtures (Impurities)

| MOLAR RATIO[a,b] | AMOUNT (mg) | | | IMPURITIES (% BY PEAK AREA) | | |
|---|---|---|---|---|---|---|
| | Crospovidone | Atrasentan | Anti-Oxidant | Initial | 7 Days | 3 Weeks |
| 1:0 | 455.03 | 50.17 | 0 | 0 | 0.97 | 2.9 |
| | 435.07 | 52.08 | | | | |
| | 444.33 | 53.85 | | | | |
| 40:1 | 450.24 | 49.75 | 0.488 | 0 | 1.07 | 4.32 |
| | 457.36 | 51.01 | 0.752 | | | |
| | 467.29 | 50.92 | 0.539 | | | |

TABLE 3-A-continued

L-Ascorbic Acid Mixtures (Impurities)

| MOLAR RATIO[a,b] | AMOUNT (mg) Crospovidone | Atrasentan | Anti-Oxidant | IMPURITIES (% BY PEAK AREA) Initial | 7 Days | 3 Weeks |
|---|---|---|---|---|---|---|
| 10:1 | 463.96 | 48.18 | 2.42 | 0 | 0.98 | 1.72 |
|  | 457.52 | 49.48 | 1.740 |  |  |  |
|  | 434.63 | 49.65 | 1.290 |  |  |  |
| 5:1 | 438.28 | 48.77 | 3.348 | 0 | 1.23 | 4.36 |
|  | 434.40 | 49.65 | 2.964 |  |  |  |
|  | 443.74 | 54.72 | 3.297 |  |  |  |
| 1:1 | 453.68 | 51.81 | 16.205 | 0 | 1.19 | 2.51 |
|  | 439.05 | 49.87 | 15.713 |  |  |  |
|  | 450.89 | 49.87 | 15.645 |  |  |  |

[a]Molar ratio of Atrasentan:anti-oxidant.
[b]Weight ratio of disintegrant:atrasentan held constant at 9:1 for all samples.

TABLE 3-B

Sodium Metabisulfite Mixtures (Impurities)

| MOLAR RATIO[a,b] | AMOUNT (mg) Crospovidone | Atrasentan | Anti-Oxidant | IMPURITIES (% BY PEAK AREA) Initial | 7 Days | 3 Weeks |
|---|---|---|---|---|---|---|
| 1:0 | 445.62 | 50.99 | 0 | 0 | 1.32 | 1.35 |
|  | 433.54 | 50.24 |  |  |  |  |
|  | 461.37 | 51.51 |  |  |  |  |
| 40:1 | 436.67 | 51.35 | 0.648 | 0 | 0.15 | 0.81 |
|  | 446.07 | 51.19 | 0.388 |  |  |  |
|  | 452.95 | 48.59 | 0.591 |  |  |  |
| 10:1 | 452.39 | 48.62 | 1.741 | 0.32 | 0.0 | 0.48 |
|  | 467.67 | 49.21 | 1.548 |  |  |  |
|  | 440.83 | 50.20 | 1.818 |  |  |  |
| 5:1 | 438.55 | 50.93 | 3.785 | 1.05 | 0.32 | 0.58 |
|  | 452.75 | 50.21 | 3.469 |  |  |  |
|  | 459.80 | 52.16 | 3.050 |  |  |  |
| 1:1 | 453.75 | 53.82 | 15.649 | 4.90 | 3.32 | 7.62 |
|  | 437.94 | 53.65 | 14.883 |  |  |  |
|  | 454.18 | 54.87 | 15.041 |  |  |  |

[a]Molar ratio of atrasentan:anti-oxidant.
[b]Weight ratio of disintegrant:atrasentan held constant at 9:1 for all samples.

TABLE 3-C

L-Cysteine Mixtures (Impurities)

| MOLAR RATIO[a,b] | AMOUNT (mg) Crospovidone | Atrasentan | Anti-Oxidant | IMPURITIES (% BY PEAK AREA) Initial | 7 Days | 3 Weeks |
|---|---|---|---|---|---|---|
| 1:0 | 451.69 | 52.28 | 0 | 0 | 0.76 | 5.02 |
|  | 453.62 | 50.92 |  |  |  |  |
|  | 440.53 | 51.27 |  |  |  |  |
| 40:1 | 456.22 | 51.09 | 0.485 | 0 | 0.72 | 2.99 |
|  | 459.97 | 52.04 | 0.680 |  |  |  |
|  | 443.50 | 48.93 | 0.410 |  |  |  |
| 10:1 | 439.41 | 48.93 | 1.317 | 0 | 0.47 | 0.81 |
|  | 440.02 | 49.67 | 1.612 |  |  |  |
|  | 438.98 | 47.98 | 1.410 |  |  |  |
| 5:1 | 436.56 | 54.65 | 2.825 | 0 | 0.32 | 0.46 |
|  | 445.34 | 50.17 | 2.880 |  |  |  |
|  | 432.66 | 51.04 | 2.752 |  |  |  |
| 1:1 | 454.25 | 48.03 | 13.310 | 0 | 0.0 | 0.0 |
|  | 462.93 | 53.19 | 13.005 |  |  |  |
|  | 454.65 | 54.11 | 14.603 |  |  |  |

[a]Molar ratio of atrasentan:anti-oxidant.
[b]Weight ratio of disintegrant:atrasentan to held constant at 9:1 for all samples.

TABLE 3-D

L-Ascorbic Acid Mixtures (Atrasentan)

| MOLAR RATIO[a,b] | AMOUNT (mg) Crospovidone | Atrasentan | Anti-Oxidant | WEIGHT % ATRASENTAN Initial | 7 Days | 3 Weeks |
|---|---|---|---|---|---|---|
| 1:0 | 455.03 | 50.17 | 0 | 102.9 | 100.9 | 98.3 |
|  | 435.07 | 52.08 |  |  |  |  |
|  | 444.33 | 53.85 |  |  |  |  |
| 40:1 | 450.24 | 49.75 | 0.488 | 104.4 | 101.0 | 98.1 |
|  | 457.36 | 51.01 | 0.752 |  |  |  |
|  | 467.29 | 50.92 | 0.539 |  |  |  |
| 10:1 | 463.96 | 48.18 | 2.42 | 103.7 | 102.0 | 97.3 |
|  | 457.52 | 49.48 | 1.740 |  |  |  |
|  | 434.63 | 49.65 | 1.290 |  |  |  |
| 5:1 | 438.28 | 48.77 | 3.348 | 102.5 | 100.7 | 97.7 |
|  | 434.40 | 49.65 | 2.964 |  |  |  |
|  | 443.74 | 54.72 | 3.297 |  |  |  |
| 1:1 | 453.68 | 51.81 | 16.205 | 102.9 | 100.4 | 95.5 |
|  | 439.05 | 49.87 | 15.713 |  |  |  |
|  | 450.89 | 49.87 | 15.645 |  |  |  |

[a]Molar ratio of Atrasentan:anti-oxidant.
[b]Weight ratio of disintegrant:atrasentan held constant at 9:1 for all samples.

TABLE 3-E

Sodium Metabisulfite Mixtures (Atrasentan)

| MOLAR RATIO[a,b] | AMOUNT (mg) Crospovidone | Atrasentan | Anti-Oxidant | WEIGHT % ATRASENTAN Initial | 7 Days | 3 Weeks |
|---|---|---|---|---|---|---|
| 1:0 | 445.62 | 50.99 | 0 | 101.6 | 98.8 | 97.9 |
|  | 433.54 | 50.24 |  |  |  |  |
|  | 461.37 | 51.51 |  |  |  |  |
| 40:1 | 436.67 | 51.35 | 0.648 | 101.8 | 101.0 | 98.5 |
|  | 446.07 | 51.19 | 0.388 |  |  |  |
|  | 452.95 | 48.59 | 0.591 |  |  |  |
| 10:1 | 452.39 | 48.62 | 1.741 | 100.6 | 101.3 | 99.6 |
|  | 467.67 | 49.21 | 1.548 |  |  |  |
|  | 440.83 | 50.20 | 1.818 |  |  |  |
| 5:1 | 438.55 | 50.93 | 3.785 | 99.9 | 101.3 | 99.3 |
|  | 452.75 | 50.21 | 3.469 |  |  |  |
|  | 459.80 | 52.16 | 3.050 |  |  |  |
| 1:1 | 453.75 | 53.82 | 15.649 | 99.2 | 96.1 | 86.9 |
|  | 437.94 | 53.65 | 14.883 |  |  |  |
|  | 454.18 | 54.87 | 15.041 |  |  |  |

[a]Molar ratio of atrasentan:anti-oxidant.
[b]Weight ratio of disintegrant:atrasentan held constant at 9:1 for all samples.

TABLE 3-F

L-Cysteine Mixtures (Atrasentan)

| MOLAR RATIO[a,b] | AMOUNT (mg) Crospovidone | Atrasentan | Anti-Oxidant | WEIGHT % ATRASENTAN Initial | 7 Days | 3 Weeks |
|---|---|---|---|---|---|---|
| 1:0 | 451.69 | 52.28 | 0 | 101.6 | 101.4 | 97.4 |
|  | 453.62 | 50.92 |  |  |  |  |
|  | 440.53 | 51.27 |  |  |  |  |
| 40:1 | 456.22 | 51.09 | 0.485 | 101.8 | 100.7 | 98.3 |
|  | 459.97 | 52.04 | 0.680 |  |  |  |
|  | 443.50 | 48.93 | 0.410 |  |  |  |
| 10:1 | 439.41 | 48.93 | 1.317 | 101.3 | 100.2 | 99.7 |
|  | 440.02 | 49.67 | 1.612 |  |  |  |
|  | 438.98 | 47.98 | 1.410 |  |  |  |
| 5:1 | 436.56 | 54.65 | 2.825 | 100.7 | 100.3 | 99.5 |
|  | 445.34 | 50.17 | 2.880 |  |  |  |
|  | 432.66 | 51.04 | 2.752 |  |  |  |

TABLE 3-F-continued

L-Cysteine Mixtures (Atrasentan)

| MOLAR RATIO[a,b] | AMOUNT (mg) | | | WEIGHT % ATRASENTAN | | |
|---|---|---|---|---|---|---|
| | Crospovidone | Atrasentan | Anti-Oxidant | Initial | 7 Days | 3 Weeks |
| 1:1 | 454.25 | 48.03 | 13.310 | 101.8 | 101.4 | 101.3 |
| | 462.93 | 53.19 | 13.005 | | | |
| | 454.65 | 54.11 | 14.603 | | | |

[a]Molar ratio of atrasentan:anti-oxidant.
[b]Weight ratio of disintegrant:atrasentan held constant at 9:1 for all samples.

In general, the stability data for the Phase IIb tablets indicate that L-cysteine hydrochloride monohydrate provides the greatest stabilizing effect of the three anti-oxidants, an interesting result given the relative oxidation reduction potentials ("ORP") of the three anti-oxidants. Atrasentan has an ORP value greater than about 900 mV. Ascorbic acid, sodium metabisulfite, and L-cysteine have ORP values of about 100-280 mV, about 175-300 mV, and about 815-965 mV, respectively. Although L-cysteine has an ORP value that is relatively close to the ORP value of atrasentan (indicating the least oxidative reactivity of the anti-oxidants tested with respect to atrasentan), it still provided the greatest stabilizing effect.

Example 4: Effect of Atrasentan/L-Cysteine Molar Ratio on Tablet Stability

A study was conducted to evaluate the effect of molar ratio of atrasentan to L-cysteine on atrasentan degradation in uncoated tablets comprising L-cysteine hydrochloride monohydrate, but otherwise substantially the same as the tablet core composition described in Table 2-B of Example 2. The tablets tested had the compositions shown in Tables 4-A (2:1 molar ratio), 4-B (1:1 molar ratio), and 4-C (1:2 molar ratio) below. The tablets were prepared using a wet granulation process and were compressed into round tablets having a core weight of 120 mg and a diameter of 6.5 mm.

TABLE 4-A

L-Cysteine Tablet (2:1 Molar Ratio)

| INGREDIENT | WEIGHT/WEIGHT % | mg/TABLET |
|---|---|---|
| Atrasentan Monohydrochloride | 0.31 | 0.372[a] |
| Lactose Monohydrate (Regular) | 91.14 | 109.4 |
| L-Cysteine Hydrochloride Monohydrate | 0.050 | 0.060 |
| Hypromellose E5 (Premium LV) | 3.000 | 3.600 |
| Crospovidone (POLYPLASDONE ™ XL) | 3.500 | 4.200 |
| Silicon Dioxide (SYLOID ® 244FP) | 0.500 | 0.600 |
| Glyceryl Behenate (COMPRITOL ®) | 1.500 | 1.800 |
| Purified water[b] | N/A | N/A |
| Total | 100% | 120.0 mg |

[a]Atrasentan monohydrochloride salt factor = 1.07 (i.e., 0.31 mg free base × 1.07 = 0.372 mg salt).
[b]Granulation suspension medium. Less than 2% present in final product.

TABLE 4-B

L-Cysteine Tablet (1:1 Molar Ratio)

| INGREDIENT | WEIGHT/WEIGHT % | mg/TABLET |
|---|---|---|
| Atrasentan Monohydrochloride | 0.31 | 0.372[a] |
| Lactose Monohydrate (Regular) | 91.09 | 109.3 |
| L-Cysteine Hydrochloride Monohydrate | 0.0999 | 0.120 |
| Hypromellose E5 (Premium LV) | 3.000 | 3.600 |
| Crospovidone (POLYPLASDONE ™ XL) | 3.500 | 4.200 |
| Silicon Dioxide (SYLOID ® 244FP) | 0.500 | 0.600 |
| Glyceryl Behenate (COMPRITOL ®) | 1.500 | 1.800 |
| Purified water[b] | N/A | N/A |
| Total | 100% | 120.0 mg |

[a]Atrasentan monohydrochloride salt factor = 1.07 (i.e., 0.31 mg free base × 1.07 = 0.372 mg salt).
[b]Granulation suspension medium. Less than 2% present in final product.

TABLE 4-C

L-Cysteine Tablet (1:2 Molar Ratio)

| INGREDIENT | WEIGHT/WEIGHT % | mg/TABLET |
|---|---|---|
| Atrasentan Monohydrochloride | 0.31 | 0.372[a] |
| Lactose Monohydrate (Regular) | 91.07 | 109.2 |
| L-Cysteine Hydrochloride Monohydrate | 0.200 | 0.240 |
| Hypromellose E5 (Premium LV) | 3.000 | 3.600 |
| Crospovidone (POLYPLASDONE ™ XL) | 3.500 | 4.200 |
| Silicon Dioxide (SYLOID ® 244FP) | 0.500 | 0.600 |
| Glyceryl Behenate (COMPRITOL ®) | 1.500 | 1.800 |
| Purified water[b] | N/A | N/A |
| Total | 100% | 120.0 mg |

[a]Atrasentan monohydrochloride salt factor = 1.07 (i.e., 0.31 mg free base × 1.07 = 0.372 mg salt).
[b]Granulation suspension medium. Less than 2% present in final product.

The tablets described above were tested for stability using an accelerated stability testing protocol. The tablets were packaged in 3 ounce HDPE bottles with induction sealed caps and stored at 50° C. and ambient relative humidity. Each bottle contained 20 tablets and 1.1 g of a silica desiccant. Tablet stability was assessed at the end of 3, 6, and 9 weeks. The stability testing results are reported below in Table 4-D. The "Assay" data reported represent the weight percent of atrasentan measured relative to the labeled dose (i.e., 0.31 mg). All data reported represent single values from single runs (n=1).

TABLE 4-D

Stability Test Results For L-Cysteine Tablets

| MOLAR RATIO[a] | WEIGHT % ATRASENTAN | | | |
|---|---|---|---|---|
| | INITIAL | 3 WEEKS | 6 WEEKS | 9 WEEKS |
| 2:1 | 95.4% | 95.2% | 93.9% | 92.9% |
| 1:1 | 99.3% | 98.3% | 98.2% | 98.7% |
| 1:2 | 99.9% | 98.6% | 99.1% | 98.6% |

[a]Molar ratio of atrasentan:anti-oxidant.

Example 5: Effect of HPMC on Tablet Stability (Lab Scale)

A lab-scale study (i.e., each batch prepared was less than 500 mg) was conducted to evaluate the effect of HPMC on atrasentan tablet stability. Uncoated tablets corresponding to the compositions shown in Table 5-A below were prepared at a drug loading of 0.45% (based on the weight of atrasentan monohydrochloride) using five different methods of preparation that differed in the manner atrasentan was treated with the HPMC.

TABLE 5-A

HPMC Tablet

| INGREDIENT | WEIGHT/ WEIGHT % | mg/TABLET |
|---|---|---|
| Atrasentan Monohydrochloride | 0.449 | 0.54[a] |
| Lactose Monohydrate (Regular) | 91.05 | 109.3 |
| Hypromellose E5 (Premium LV) | 3.000 | 3.600 |
| Crospovidone (POLYPLASDONE ™ XL) | 3.500 | 4.200 |
| Silicon Dioxide (SYLOID ®) | 0.500 | 0.600 |
| Glyceryl Behenate (COMPRITOL ®) | 1.500 | 1.800 |
| Purified water[b] | N/A | N/A |
| Total | 100% | 120 mg |

[a]Atrasentan monohydrochloride salt factor = 1.07.
[b]Granulation suspension medium. Less than 2% present in final product.

Method of Preparation 1 (Wet Granulation with HPMC/Atrasentan Solution):

Atrasentan was completely dissolved in a 9% HPMC solution. All other ingredients were added to a granulation bowl in dry form. The atrasentan/HPMC solution was sprayed into the granulation bowl and the ingredients were wet granulated using a lab-scale key granulator. The granulated mixture was tray-dried in an oven without vacuum and then compressed into tablets that were left uncoated.

Method of Preparation 2 (Wet Granulation with HPMC/Atrasentan Suspension):

Atrasentan was added to a 9% HPMC solution to form a suspension. All other ingredients were added to a granulation bowl in dry form. The atrasentan/HPMC suspension was sprayed into the granulation bowl and the ingredients were wet granulated using lab-scale key granulator. The granulated mixture was tray-dried in an oven without vacuum and then compressed into uncoated tablets.

Method of Preparation 3 (Direct Blend: Dry Mix):

Atrasentan was dry mixed with HPMC. The atrasentan/HPMC mixture was then mixed with the remaining ingredients in dry form and without the addition of water or any other liquid. The mixed ingredients were directly compressed into tablets that were left uncoated.

Method of Preparation 4 (Direct Blend: Dry Granulation):

Atrasentan was compressed with HPMC (dry granulation) and sieved to provide atrasentan/HPMC dry granules. The atrasentan/HPMC dry granules were then mixed with the remaining ingredients in dry form and without the addition of water or any other liquid. The mixed ingredients were directly compressed into tablets that were left uncoated.

Method of Preparation 5 (Direct Blend: No Pre-Treatment):

Atrasentan, HPMC, and the other ingredients were mixed in dry form without any pre-treatment of the atrasentan with HPMC and without the addition of water or any other liquid. The mixed ingredients were directly compressed into tablets that were left uncoated.

In all cases, the final mixture was manually compressed into 1 g tablets using a Carver Press.

The tablets described above were tested for stability using an accelerated stability testing protocol under which the tablets were stored at 50° C. and 75% relative humidity in sealed, 5 oz., HDPE bottles containing 2 g of a clay desiccant. Tablet stability was assessed at the initiation of testing and at the end of three, six, and eight weeks. Stability testing results are reported below in Table 6-B. The "Impurities" data reported represent the percent impurities by HPLC peak area percent. All data reported represent single values from single runs (n=1).

TABLE 5-B

Stability Test Results

| | IMPURITIES (% BY PEAK AREA) | | | |
|---|---|---|---|---|
| METHOD | Initial | 3 Weeks | 6 Weeks | 8 Weeks |
| 1 | 3.8 | 5.6 | 5.8 | 6.5 |
| 2 | 4.2 | 5.7 | 7.1 | 7.1 |
| 3 | 2.7 | 3.9 | 3.7 | 3.8 |
| 4 | 3.4 | 5.2 | 4.7 | 4.6 |
| 5 | 3.8 | 4.8 | 5.2 | 5.7 |

The data indicate that pre-treatment of atrasentan with HPMC during the preparation of the direct blend tablets (i.e., dry-mixed tablets prepared in Method 3 or dry-granulated tablets prepared as in Method 4) reduces total impurities relative to direct blend tablets prepared without any pre-treatment of atrasentan with HPMC (i.e., dry-mixing as in Method 5).

The data for the wet-granulated tablets prepared as in Method 1 or Method 2 indicate a higher impurity content than is typically observed for wet-granulated tablets prepared in larger scale operations (see Example 6 below). It is believed that the higher impurities content is attributable to factors such as the use of lab-scale equipment (e.g., tray-drying in an oven without vacuum rather than vacuum drying) and the use of lower-grade excipients than typically required for the preparation of clinical and commercial tablets.

Example 6: Effect of HPMC on Tablet Stability (Manufacturing Scale)

A manufacturing-scale study (i.e., each batch prepared was at least about 15 kg) was conducted to evaluate the effect of HPMC on atrasentan tablet stability. Uncoated tablets corresponding to the compositions shown in Table 6-A below were prepared at three different drug loadings (0.05%, 0.17%, and 0.27%) using three different methods of preparation as described below.

TABLE 6-A

HPMC Tablet

| INGREDIENT | WEIGHT/ WEIGHT % | mg/TABLET |
|---|---|---|
| Atrasentan Monohydrochloride | 0.05-0.27 | 0.05-0.27[a] |
| Lactose Monohydrate (Regular) | Quantity Sufficient | Quantity Sufficient |
| Hypromellose E5 (Premium LV) | 3.000 | 3.000 |
| Crospovidone (POLYPLASDONE ™ XL) | 3.500 | 3.500 |
| Silicon Dioxide (SYLOID ®) | 0.500 | 0.500 |
| Glyceryl Behenate (COMPRITOL ®) | 1.500 | 1.500 |
| Purified water[b] | N/A | N/A |
| Total | 100% | 100 mg |

[a]Atrasentan monohydrochloride salt factor = 1.07.
[b]Granulation suspension medium. Less than 2% present in final product.

Method of Preparation 1 (Direct Blend):

All ingredients were mixed in dry form without the addition of water or any other liquid. The mixed ingredients were directly compressed into tablets that remained uncoated for stability testing.

Method of Preparation 2 (Wet Granulation with HPMC Solution):

All ingredients except HPMC were added dry to a granulation bowl and were wet granulated using a 9% HPMC solution. The granulated mixture was dried under vacuum and then compressed into uncoated tablets.

Method of Preparation 3 (Wet Granulation with HPMC/Atrasentan Suspension):

Atrasentan was added to a 9% HPMC solution to form a suspension. All other ingredients were added to a granulation bowl in dry form. The suspension was sprayed into the granulation bowl and the ingredients were wet granulated. The granulated mixture was dried under vacuum and then compressed into tablets that remained uncoated for stability testing.

The tablets described above were tested for stability using an accelerated stability testing protocol under which 20 tablets were stored at 50° C. and 75% relative humidity in a sealed, 3 oz., HDPE bottle containing 2 g of a clay desiccant. Tablet stability was assessed at the initiation of testing and at the end of two and four weeks. Stability testing results are reported below in Table 6-A (Method 1), Table 6-B (Method 2), and Table 6-C (Method 3). The "Impurities" data reported represent the percent impurities by HPLC peak area percent. All data reported represent single values from single runs (i.e., n=1).

TABLE 6-B

Stability Test Results (Method 1)

| DRUG LOADING (%) | IMPURITIES (% BY PEAK AREA) | | |
|---|---|---|---|
| | Initial | 2 Weeks | 4 Weeks |
| 0.05 | 0.30 | 1.61 | 2.52 |
| 0.17 | Not Tested | Not Tested | Not Tested |
| 0.27 | Not Tested | Not Tested | Not Tested |

TABLE 6-C

Stability Test Results (Method 2)

| DRUG LOADING (%) | IMPURITIES (% BY PEAK AREA) | | |
|---|---|---|---|
| | Initial | 2 Weeks | 4 Weeks |
| 0.05 | 1.23 | 2.13 | 2.52 |
| 0.17 | NR | 0.59 | 0.98 |
| 0.27 | 0.39 | 1.68 | 2.91 |

TABLE 6-D

Stability Test Results (Method 3)

| DRUG LOADING (%) | IMPURITIES (% BY PEAK AREA) | | |
|---|---|---|---|
| | Initial | 2 Weeks | 4 Weeks |
| 0.05 | 0.76 | 1.08 | 1.26 |
| 0.17 | NR | 0.67 | 0.68 |
| 0.27 | 0.13 | 0.32 | 0.55 |

Although there was no discernible difference in content uniformity between the tablets prepared by Method 2 (atrasentan added dry to the granulation bowl prior to the addition of the HPMC solution) and the tablets prepared by Method 3 (atrasentan added to the granulation bowl as an HPMC/atrasentan suspension), the chemical degradation of atrasentan over time was higher for the tablets prepared by Method 2 than for the tablets prepared by Method 3. In addition, the rate of chemical degradation of atrasentan for the tablets prepared by Method 1 (atrasentan and HPMC added dry to the granulation bowl) was higher than for the corresponding tablets prepared by Method 2 (atrasentan added dry to the granulation bowl prior to the addition of the HPMC solution).

Example 7: Effect of HPMC on Spray-Coated Placebo Core Tablet Stability

A study was conducted to compare the effect of HPMC and Kollicoat (a copolymer of polyvinyl alcohol) on atrasentan tablet stability. Atrasentan was dissolved or suspended (depending upon drug loading) in a polymer coating solution to form an atrasentan/polymer coating solution. In each case, a placebo core having the composition shown in Table 7-A was sprayed with a polymer base coating, then the atrasentan/polymer coating, and finally a polymer seal coat. The atrasentan/polymer coating, polymer base coating, and polymer seal coating had the compositions shown in Table 7-B (HPMC/0.05 mg atrasentan), Table 7-C (HPMC/0.75 mg atrasentan), Table 7-D (Kollicoat/0.05 mg atrasentan), and Table 7-E (Kollicoat/0.55 mg atrasentan).

TABLE 7-A

Placebo Core Tablet
PLACEBO CORE TABLET COMPOSITION

| INGREDIENT | WEIGHT/WEIGHT % | mg/TABLET |
|---|---|---|
| Avicel PH 102 | 46.6 | 116.25 |
| Lactose Monohydrate FastFlo | 46.5 | 116.25 |
| Sodium Stearyl Fumarate | 2 | 5 |
| Croscarmellose Sodium | 2 | 5 |
| Hydroxypropyl Cellulose | 3 | 7.5 |
| Total | 100% | 250 mg |

TABLE 7-B

HPMC/Atrasentan Coating (0.055 mg)

| INGREDIENT | WEIGHT/WEIGHT % | mg/TABLET |
|---|---|---|
| ATRASENTAN/POLYMER COATING | | |
| Atrasentan Monohydrochloride | 0.022 | 0.055[a] |
| Hydroxypropylmethylcellulose (Methocel E5) | 8.0 | 19.92 |
| POLYMER BASE AND SEAL COATING[b] | | |
| Hydroxypropylmethylcellulose (Methocel E5) | 9.7 | 9.7 |
| Polyethylene Glycol 1450 | 0.3 | 0.3 |

[a]Atrasentan monohydrochloride salt factor = 1.07 (i.e., 0.05 mg free base × 1.07 = 0.055 mg salt).
[b]The polymer base coat was sprayed on the placebo core for a theoretical weight gain of 2% and the polymer seal coat was sprayed on top of the atrasentan/polymer coating layer theoretical weight gain of 2%. The combined theoretical weight gain attributable to the polymer base and seal coats was 4%.

TABLE 7-C

HPMC/Atrasentan Coating (0.79 mg)

| INGREDIENT | WEIGHT/WEIGHT % | mg/TABLET |
|---|---|---|
| ATRASENTAN/POLYMER COATING | | |
| Atrasentan Monohydrochloride | 0.32 | 0.79[a] |
| Hydroxypropylmethylcellulose (Methocel E5) | 8.2 | 20.56 |
| POLYMER BASE AND SEAL COATING[b] | | |
| Hydroxypropylmethylcellulose (Methocel E5) | 9.7 | 9.7 |
| Polyethylene Glycol 1450 | 0.3 | 0.3 |

[a]Atrasentan monohydrochloride salt factor = 1.07 (i.e., 0.75 mg free base × 1.07 = 0.79 mg salt).
[b]The polymer base coat was sprayed on the placebo core for a theoretical weight gain of 2% and the polymer seal coat was sprayed on top of the atrasentan/polymer coating layer theoretical weight gain of 2%. The combined theoretical weight gain attributable to the polymer base and seal coats was 4%.

TABLE 7-D

Kollicoat/Atrasentan Coating (0.055 mg)

| INGREDIENT | WEIGHT/WEIGHT % | mg/TABLET |
|---|---|---|
| ATRASENTAN/POLYMER COATING | | |
| Atrasentan Monohydrochloride | 0.022 | 0.055[a] |
| Kollicoat IR | 8.6 | 21.50 |
| POLYMER BASE AND SEAL COATING[b] | | |
| Kollicoat IR | 15 | 10 |

[a]Atrasentan monohydrochloride salt factor = 1.07 (i.e., 0.05 mg free base × 1.07 = 0.055 mg salt).
[b]The polymer base coat was sprayed on the placebo core for a theoretical weight gain of 2% and the polymer seal coat was sprayed on top of the atrasentan/polymer coating layer theoretical weight gain of 2%. The combined theoretical weight gain attributable to the polymer base and seal coats was 4%.

TABLE 7-E

Kollicoat/Atrasentan Coating (0.59 mg)

| INGREDIENT | WEIGHT/WEIGHT % | mg/TABLET |
|---|---|---|
| ATRASENTAN/POLYMER COATING | | |
| Atrasentan Monohydrochloride | 0.24 | 0.59[a] |
| Kollicoat IR | 9.0 | 22.50 |
| POLYMER BASE AND SEAL COATING* | | |
| Kollicoat IR | 15 | 10 |

[a]Atrasentan monohydrochloride salt factor = 1.07 (i.e., 0.55 mg free base × 1.07 = 0.59 mg salt).
[b]The polymer base coat was sprayed on the placebo core for a theoretical weight gain of 2% and the polymer seal coat was sprayed on top of the atrasentan/polymer coating layer theoretical weight gain of 2%. The combined theoretical weight gain attributable to the polymer base and seal coats was 4%.

The tablets prepared as described above were tested for stability using an accelerated stability testing protocol under which 20 tablets were stored at 50° C. and 75% relative humidity in a sealed, 5 oz. HDPE bottles containing 2 g of a clay desiccant. Tablet stability was assessed at the initiation of testing and at the end of two and four weeks. Stability testing results are reported below in Table 7-F. The "Impurities" data reported represent the percent impurities by HPLC peak area percent. All data reported represent single values from single runs (i.e., n=1).

TABLE 7-F

Stability Test Results

| ATRASENTAN/POLYMER COATING | IMPURITIES (% BY PEAK AREA) | | |
|---|---|---|---|
| | Initial | 2 Weeks | 4 Weeks |
| HPMC/0.05 mg atrasentan | 0.80 | 1.11 | 0.74 |
| HPMC/0.75 mg atrasentan | 0.17 | 0.22 | 0.24 |
| Kollicoat/0.05 mg atrasentan | 1.81 | 2.68 | 2.38 |
| Kollicoat/0.50 mg atrasentan | 0.69 | 1.87 | 1.60 |

Because degradation of atrasentan can be moisture-activated, the atrasentan-coated tablet approach of this Example is considered to be a product presentation that is more susceptible to atrasentan degradation. The results show improved chemical stability for the HPMC-coated tablets relative to the Kollicoat-coated tablets.

Example 8: Effect of HPMC on Atrasentan Solid State Behavior

The effect of HPMC on the solid state behavior of atrasentan was evaluated in a study in which slurry samples of atrasentan Form II polymorph suspended in a 9% HPMC solution stored at room temperature and 40° C. were compared with corresponding slurry samples obtained from atrasentan Form II polymorph suspended in water stored at room temperature and 40° C. The atrasentan concentration in all four suspensions was 4.4% by weight. Samples (1 mL) were taken from each suspension at 30 minutes, 6 hours, and 30 hour from initiation and centrifuged to provide both a solid material and a filtrate for further analysis.

The solid material from each sample was analyzed by powder x-ray diffraction ("PXRD") and compared to the PXRD for the corresponding initial sample (i.e., the PXRD pattern for the atrasentan Form II polymorph). Although the primary PXRD pattern for all suspensions after 30 minutes and 6 hours at either room temperature or 40° C. still corresponded to the PXRD pattern for the atrasentan Form II polymorph, the PXRD pattern for the samples obtained from the suspensions without HPMC indicated partial conversion of the atrasentan Form II polymorph to the more thermodynamically stable atrasentan Form I polymorph at both room temperature and 40° C. A higher level of conversion was seen for the suspensions without HPMC stored at 40° C. The PXRD pattern for the samples obtained from the suspensions with HPMC stored at room temperature showed no conversion of the atrasentan Form II polymorph to the more thermodynamically stable atrasentan Form I polymorph at any timepoint. The PXRD pattern for the samples obtained from the suspensions with HPMC stored at 40° C. showed no conversion at the 6 hour timepoint and only minimal conversion at the 30 hour timepoint.

The filtrates collected from the slurry samples at each time point were freeze-dried by a lab scale lyophilizer. Prior to lyophilization of the filtrate, the pH of the suspension was measured. The average pH was 1.8 for filtrates from suspensions containing no HPMC and 2.2 for suspensions with HPMC. The pH for each sample remained consistent, regardless of time or temperature. The freeze-dried filtrates were submitted for solid-state NMR analysis to determine if any chemical interaction between HPMC and atrasentan could be observed, but the sample concentrations were too dilute for analysis.

The results indicate that the presence of HPMC in the suspension: (a) slows and possibly prevents the conversion of atrasentan Form II polymorph to the more thermodynamically stable atrasentan Form I polymorph at room temperature, and (b) slows the conversion of atrasentan Form II polymorph to the more thermodynamically stable atrasentan Form I polymorph at 40° C.

Example 9: Effect of HPMC on Atrasentan Surface Energy

Wet granulation blends prepared as described in Method 2 (atrasentan added dry to granulation bowl) and Method 3 (atrasentan added as HPMC suspension to granulation bowl) of Example 6 were analyzed prior to compression using inverse gas chromatography ("IGC") to determine the surface energy of the blends. These measurements were compared to the measured values for pure atrasentan and pure HPMC. The results are shown in Table 9 below.

TABLE 9

Surface Energy

| | DISPERSIVE SURFACE ENERGY (mJ · m$^{-2}$) | | | |
|---|---|---|---|---|
| SAMPLE | Run 1 | Run 2 | Average | Standard Deviation (%) |
| HPMC E5 | 36.3 | 36.9 | 36.6 | 1.13 |
| Atrasentan Monohydrochloride | 50.6 | 51.4 | 50.9 | 1.02 |
| Method 1 Blend | 47.9 | 46.5 | 47.2 | 2.24 |
| Method 2 Blend | 45.9 | 44.2 | 45.0 | 2.54 |

The results indicate that the blends lie closer in energy value to pure HPMC than to pure atrasentan (likely due to a larger concentration of HPMC in the blend than atrasentan). The results further indicate that the wet granulation blend prepared as described in Method 2 (atrasentan added dry to granulation bowl) has a higher surface energy than the wet granulation blend prepared as described in Method 3 (atrasentan added as HPMC suspension to granulation bowl) which is consistent with the higher atrasentan degradation seen in the Method 2 blend compared to the Method 3 blend (see Example 6).

Overall, the results of Examples 5 to 9 confirm that HPMC stabilizes atrasentan and reduces atrasentan degradation in the low-dose dosage forms of the present disclosure. This stabilizing effect is observed when atrasentan is intimately mixed with HPMC during the preparation of the dosage form, such as introducing atrasentan to the granulation bowl as an atrasentan/HPMC suspension or as a dry mixture of atrasentan and HPMC.

Example 10: Phase III Tablet Stability

Two atrasentan dosage forms having the compositions shown in Table 10-A (0.50 mg tablet) and Table 10-B (0.75 mg tablet) below were prepared for use in Phase III clinical trials to evaluate the safety and efficacy of atrasentan in treating subjects with diabetic nephropathy. The tablets were prepared using a wet granulation process and were compressed into round tablets having a core weight of 120 mg and a diameter of 6.5 mm. A third atrasentan dosage form having the composition shown in Table 10-C (0.35 mg tablet) can be prepared in a similar manner. The 0.35 mg tablet, 0.50 mg tablet, and 0.75 mg tablet have drug loads (based on weight of atrasentan monohydrochloride) of 0.31%, 0.45%, and 0.67%, respectively.

TABLE 10-A

Phase III Tablet (0.50 mg)

TABLET CORE COMPOSITION

| INGREDIENT | WEIGHT/ WEIGHT % | mg/TABLET |
|---|---|---|
| Atrasentan Monohydrochloride | 0.4460 | 0.5350$^a$ |
| Lactose Monohydrate (Regular) | 90.91 | 109.1 |
| L-Cysteine Hydrochloride Monohydrate | 0.1440 | 0.1728 |
| Hypromellose E5 (Premium LV) | 3.000 | 3.600 |
| Crospovidone (POLYPLASDONE ™ XL) | 3.500 | 4.200 |
| Silicon Dioxide (SYLOID ® 244FP) | 0.500 | 0.600 |
| Glyceryl Behenate (COMPRITOL ®) | 1.500 | 1.800 |
| Purified water | N/A | N/A |
| Total | 100% | 120.0 mg |

FILM-COATED TABLET COMPOSITION

| INGREDIENT | WEIGHT/ WEIGHT %$^c$ | mg/TABLET$^d$ |
|---|---|---|
| PEG1450 | 3 | 0.1 |
| Hypromellose E5 (Premium LV) | 97 | 3.5 |
| Purified water | N/A | N/A |
| Total | 100% | 123.6 mg |

$^a$Atrasentan monohydrochloride salt factor = 1.07 (i.e., 0.50 mg free base × 1.07 = 0.5350 mg salt).
$^b$Granulation suspension medium. Less than 2% present in final product.
$^c$Based on an aqueous solution of 10% solids.
$^d$Based on a 120 mg tablet weight with a coating weight gain of 3%.

TABLE 10-B

Phase III Tablet (0.75 mg)

TABLET CORE COMPOSITION

| INGREDIENT | WEIGHT/ WEIGHT % | mg/TABLET |
|---|---|---|
| Atrasentan Monohydrochloride | 0.6690 | 0.8025$^a$ |
| Lactose Monohydrate (Regular) | 90.61 | 108.7 |
| L-cysteine Hydrochloride Monohydrate | 0.216 | 0.2592 |
| Hypromellose E5 (Premium LV) | 3.000 | 3.600 |
| Crospovidone (POLYPLASDONE ™ XL) | 3.500 | 4.200 |
| Silicon Dioxide (SYLOID ® 244FP) | 0.500 | 0.600 |
| Glyceryl Behenate (COMPRITOL ®) | 1.500 | 1.800 |
| Purified water | N/A | N/A |
| Total | 100% | 120.0 mg |

FILM-COATED TABLET COMPOSITION

| INGREDIENT | WEIGHT/ WEIGHT %$^c$ | mg/TABLET$^d$ |
|---|---|---|
| PEG1450 | 3 | 0.1080 |
| Hypromellose E5 (Premium LV) | 97 | 3.492 |
| Purified water | N/A | N/A |
| Total | 100% | 123.6 mg |

$^a$Atrasentan monohydrochloride salt factor = 1.07 (i.e., 0.75 mg free base × 1.07 = 0.8025 mg salt).
$^b$Granulation suspension medium. Less than 2% present in final product.
$^c$Based on an aqueous solution of 10% solids.
$^d$Based on a 120 mg tablet weight with a coating weight gain of 3%.

TABLE 10-C 0.35 Tablet

TABLET CORE COMPOSITION

| INGREDIENT | WEIGHT/WEIGHT % | mg/TABLET |
|---|---|---|
| Atrasentan Monohydrochloride | 0.31 | 0.372[a] |
| Lactose Monohydrate (Regular) | 91.09 | 109.3 |
| L-Cysteine Hydrochloride Monohydrate | 0.0999 | 0.120 |
| Hypromellose E5 (Premium LV) | 3.00 | 3.6 |
| Crospovidone (POLYPLASDONE ™ XL) | 3.50 | 4.2 |
| Silicon Dioxide (SYLOID ®) | 0.50 | 0.6 |
| Glyceryl Behenate (COMPRITOL ®) | 1.50 | 1.8 |
| Purified water[b] | N/A | N/A |
| Total | 100% | 120 mg |

FILM-COATED TABLET COMPOSITION

| INGREDIENT | WEIGHT/WEIGHT %[c] | mg/TABLET[d] |
|---|---|---|
| PEG1450 | 3 | 0.1 |
| Hypromellose E5 (Premium LV) | 97 | 3.5 |
| Purified water | N/A | N/A |
| Total | 100% | 123.6 mg |

[a]Atrasentan monohydrochloride salt factor = 1.07 (i.e., 0.35 mg free base × 1.07 = 0.37 mg salt).
[b]Granulation suspension medium. Less than 2% present in final product.
[c]Based on an aqueous solution of 10% solids.
[d]Based on a 120 mg tablet weight with a coating weight gain of 3%.

Table 10A/B provides a comparison of the target composition for the 0.50 mg and 0.75 mg Phase III tablets prepared in large-scale tableting operations.

TABLE 10A/B

Comparison of 0.50 mg and 0.75 Tablets

| Component | Dosage Strength | |
|---|---|---|
| | 0.5 mg Amount (mg)/Tablet | 0.75 mg Amount (mg)/Tablet |
| TABLET CORE | | |
| *Intragranular* | | |
| Atrasentan HCl | 0.54 | 0.81 |
| Lactose Monohydrate | 109.1 | 108.7 |
| Hypromellose | 3.6 | 3.6 |
| Crospovidone | 4.2 | 4.2 |
| Silicon Dioxide/Silica, Anhydrous | 0.3 | 0.3 |
| Cysteine Hydrochloride/Cysteine Hydrochloride Monohydrate | 0.2 | 0.3 |
| Purified Water[a] | N/A | N/A |
| *Extragranular* | | |
| Silicon Dioxide/Silica, Anhydrous | 0.3 | 0.3 |
| Glyceryl Behenate/Glycerol Dibehenate | 1.8 | 1.8 |
| FILM COATING[B] | | |
| Polyethylene Glycol 1450 | 0.1 | 0.1 |
| Hypromellose | 3.5 | 3.5 |
| Purified Water[a] | N/A | N/A |

[a]Removed during processing
[B]Film coat weight is approximate
N/A = Not applicable The 0.50 mg and 0.75 mg Phase III tablets described above are tested for stability under each of the following storage conditions:

(a) Storage at 40° C. and 75% relative humidity with tablet stability assessed at the end of 1, 3, and 6 months (accelerated stability testing protocol);

(b) Storage at 30° C. and 75% relative humidity with tablet stability assessed at the end of 12 months (intermediate-term stability testing protocol A);

(c) Storage at 30° C. and 65% relative humidity with tablet stability assessed at the end of 12 months (intermediate-term stability testing protocol B);

(d) Storage at 25° C. and 60% relative humidity with tablet stability assessed at the end of 1, 3, 6, 9, 12, 18, and 24 months (long-term storage stability testing protocol A); and (e) Storage at 40° C. and 75% relative humidity with tablet stability assessed at the end of 1, 3, 6, 9, 12, 18, and 24 months (long-term storage stability testing protocol B).

In each stability test, 20 tablets are stored in a 3 oz HDPE bottle containing 1.1 g of a silica desiccant and having induction sealed cap. Parameters measured for the tablets at each time interval include atrasentan content relative to the labeled dose, degradation product content, water content, and dissolution rate. The 0.35 mg dosage form shown in Table 10-C can be tested in a similar manner.

Stability data for the 0.50 mg Phase III tablet and the 0.75 mg Phase III tablet under the long-term storage protocols are reported in Tables 10-D, 10-E, 10-F, and 10-G below.

TABLE 10-D

Storage Stability Under Long-Term Conditions (25° C./60% RH)
(0.50 mg Phase III Tablet)

| Test | Specification Acceptance Criteria | Initial | 1 Months | 3 Month | 6 Months | 9 Months |
|---|---|---|---|---|---|---|
| Description | Appearance Marking Shape | Tablet Unmarked Round, Biconvex | Tablet Unmarked Round, Biconvex | Tablet Unmarked Round, Biconvex | Tablet Unmarked Round, Biconvex | Tablet Unmarked Round, Biconvex |
| | Color Coating | Off-White Coated | Off-White Coated | White Coated | White Coated | Off-White Coated |
| Assay | Assay Mean | 97.5 | 96.4 | 97.0 | 98.5 | 97.8 |

TABLE 10-D-continued

Storage Stability Under Long-Term Conditions (25° C./60% RH)
(0.50 mg Phase III Tablet)

| Test | Specification Acceptance Criteria | Initial | 1 Months | 3 Month | 6 Months | 9 Months |
|---|---|---|---|---|---|---|
| Water Content | Moisture | 4.9 | 4.9 | 5.1 | 4.9 | 4.8 |
| L-Cysteine Determination | | 63.6 | 60.3 | 56.3 | 53.6 | 50.3 |
| Dissolution | 15 min: Mean | 99 | 95 | 96 | 96 | 94 |
| | 30 min: Mean | 99 | 98 | 96 | 97 | 95 |
| | 45 min: Mean | 99 | 97 | 97 | 97 | 95 |
| | 60 min: Mean | 99 | 98 | 96 | 96 | 95 |
| Degradation Products | Total % Reported | ND | ND | ND | ND | ND |

TABLE 10-E

Storage Stability Under Long-Term Conditions (25° C./60% RH)
(0.75 mg Phase III Tablet)

| Test | Specification Acceptance Criteria | Initial | 1 Months | 3 Month | 6 Months |
|---|---|---|---|---|---|
| Description | Appearance Marking Shape | Tablet Unmarked Round, Biconvex | Tablet Unmarked Round, Biconvex | Tablet Unmarked Round, Biconvex | Tablet Unmarked Round, Biconvex |
| | Color Coating | Off-White Coated | White Coated | White Coated | Off-White Coated |
| Assay | Assay Mean | 96.9 | 96.9 | 94.9 | 96.8 |
| Water Content | Moisture | 4.7 | 4.4 | 4.7 | 4.6 |
| L-Cysteine Determination | | 60.5 | 53.7 | 51.9 | 49.4 |
| Dissolution | 15 min: Mean | 94 | 95 | 94 | 91 |
| | 30 min: Mean | 96 | 98 | 97 | 94 |
| | 45 min: Mean | 96 | 98 | 96 | 95 |
| | 60 min: Mean | 96 | 98 | 97 | 95 |
| Degradation Products | Total % Reported | ND | ND | ND | ND |

TABLE 10-F

Storage Stability Under Long-Term Conditions (40° C./75% RH)
(0.50 mg Phase III Tablet)

| Test | Specification Acceptance Criteria | Initial | 1 Months | 3 Month | 6 Months |
|---|---|---|---|---|---|
| Description | Appearance Marking Shape | Tablet Unmarked Round, Biconvex | Tablet Unmarked Round, Biconvex | Tablet Unmarked Round, Biconvex | Tablet Unmarked Round, Biconvex |
| | Color Coating | Off-White Coated | Off-White Coated | White Coated | Off-White Coated |
| Assay | Assay Mean | 97.5 | 96.8 | 97.6 | 97.9 |
| Water Content | Moisture | 4.9 | 5.0 | 5.0 | 5.0 |
| L-Cysteine Determination | | 63.6 | 52.2 | 37.1 | 18.4 |
| Dissolution | 15 min: Mean | 99 | 92 | 81 | 77 |
| | 30 min: Mean | 99 | 99 | 95 | 97 |
| | 45 min: Mean | 99 | 97 | 96 | 97 |
| | 60 min: Mean | 99 | 98 | 96 | 97 |
| Degradation Products | Total % Reported | ND | ND | ND | ND |

TABLE 10-G

Storage Stability Under Long-Term Conditions (40° C./75% RH)
(0.75 mg Phase III Tablet)

| Test | Specification Acceptance Criteria | Initial | 1 Months | 3 Month | 6 Months |
|---|---|---|---|---|---|
| Description | Appearance Marking Shape | Tablet Unmarked Round, Biconvex | Tablet Unmarked Round, Biconvex | Tablet Unmarked Round, Biconvex | Tablet Unmarked Round, Biconvex |
| | Color Coating | Off-White Coated | White Coated | White Coated | Pale yellow Coated |
| Assay | Assay Mean | 96.9 | 95.2 | 95.4 | 96.7 |
| Water Content | Moisture | 4.7 | 4.7 | 4.8 | 4.9 |
| L-Cysteine Determination | | 60.5 | 49.1 | 36.6 | 23.2 |
| Dissolution | 15 min: Mean | 94 | 80 | 72 | 72 |
| | 30 min: Mean | 96 | 96 | 98 | 95 |
| | 45 min: Mean | 96 | 96 | 97 | 95 |
| | 60 min: Mean | 96 | 96 | 97 | 94 |
| Degradation Products | Total % Reported | ND | ND | 0.18 | 0.13 |

Example 11: Packaged Tablet Stability

Stability of the 0.50 mg Phase IIb tablet (i.e., the tablet corresponding to Table 2-B of Example 2) and the 0.50 mg Phase III tablet (i.e., the tablet corresponding to Table 10-A of Example 10) packaged in several different configurations was tested. The packaging configurations tested included:

(a) tablets in a one ounce HDPE bottle containing 1.1 g of a silica desiccant;
(b) tablet in an aluminum (Al) foil blister;
(c) tablet in an ACLAR® 3000 blister;
(d) tablet in an ACLAR® 4000 blister;
(e) tablets in an ACLAR® 4000 blister sealed in a foil overwrap with 1.1 g of a silica desiccant; and
(f) tablets blistered in an ACLAR® Rx160 blister sealed in a foil overwrap with 1.1 g of a silica desiccant.

The packaged tablets were tested for stability using an accelerated stability testing protocol under which the tablets were stored at 40° C. and 75% relative humidity and tablet stability was assessed at initiation of the testing and at the end of one, three, and six months. Accelerated stability testing results are reported below in Table 11. The "Assay" data reported represent the weight percent of atrasentan measured relative to the labeled dose (i.e., 0.50 mg). All data reported represent single values from single runs (i.e., n=1).

TABLE 11

Packaged Tablets

| TABLET | PACKAGING CONFIGURATION | WEIGHT % ATRASENTAN | | | |
|---|---|---|---|---|---|
| | | INITIAL | 1 MONTH | 3 MONTHS | 6 MONTHS |
| Phase III tablet (0.50 mg) | 20 Tablets in a one ounce HDPE bottle containing 1.1 g of a silica desiccant | 100.1% | 100.4% | 100.4% | 100.3% |
| | Tablet in aluminum (Al) foil blister | 99.3% | 98.8% | 100.6% | 99.3% |
| | Tablet in an ACLAR® 4000 blister | 99.9% | 98.6% | 99.5% | 97.1% |
| | 32 Tablets blistered in an ACLAR® 4000 blister sealed in a foil overwrap with 1.1 g of a silica desiccant | 99.4% | 97.7% | 100.1% | 99.1% |
| Phase IIb tablet (0.50 mg) | 32 Tablets blistered in an ACLAR® Rx160 blister sealed in a foil overwrap with 1.1 g of a silica desiccant | 99.3% | 98.8% | 100.8% | 99.6% |
| | Tablet in aluminum (Al) foil blister | 98.8% | 96.9% | 95.7% | 96.7% |
| | Tablet in an ACLAR® 3000 blister | 100.2% | 97.9% | 95.3% | 91.2% |

With the exception of the more protective blister sealed in a foil overwrap with desiccant packaging, the Phase III tablet containing L-cysteine exhibited improved stability relative to the Phase IIb tablet in all packaging configurations tested and should be suitable for use in a variety of blister package configurations.

Example 12: Preparation of Phase III Tablets

One batch of the 0.75 mg Phase III tablets (i.e., the tablet corresponding to Table 10-B of Example 10) was prepared as described below.

Atrasentan monohydrochloride (0.67 kg) and a first portion of hydroxypropyl methylcellulose (Hypromellose E5, 0.84 kg) were added to a poly-bag and manually blended for about five minutes. The mixture of atrasentan monohydrochloride/hydroxypropyl methylcellulose was added slowly to water (9.4 kg) with stirring to form a suspension. The suspension was cooled to 12° C. and the cooled suspension was mixed for three cycles under the following mixing conditions: two minutes of high shear mixing using an agitator and homogenizer at 100% of the maximum speed followed by 120 minutes of mixing using the agitator only at 100% of the maximum speed. The suspension was mixed for an additional nine hours at 12° C. using the agitator at 100% of the maximum speed. L-cysteine hydrochloride monohydrate (0.216 kg) was added to the suspension with stirring. The suspension was mixed for an additional 20 minutes using an agitator at 100% of the maximum speed and then heated to 20° C.

The intragranular excipients lactose monohydrate (90.61 kg), a second portion of hydroxypropyl methylcellulose (Hypromellose E5, 2.16 kg), crospovidone (POLYPLASDONE™ XL, 3.5 kg), and a first portion of silicon dioxide (SYLOID®, 0.25 kg) were added to a single pot processor and blended for 10 minutes at 10 RPM. The intragranular excipients were then blended for an additional five minutes at 102 RPM. The atrasentan suspension prepared as described above was then added to the single pot processor at an average rate of 3.8 kg/minute while the contents of single pot processor were mixed at 102 RPM. Rinse water (7.6 kg) was added to the suspension vessel and the rinse water was then transferred to the single pot processor at an average rate of 3.8 kg/minutes while the contents of the single pot processor were mixed at 102 RPM.

The resulting granulation mixture was wet-massed with high shear mixing for 30 seconds to one minute to an achieved target power end point (6.3 kW). The granulation mixture was dried under vacuum at less than 15 mbar with the single pot processor bowl and lid temperature maintained at 75° C. until a loss on drying moisture measurement of 0.7% to 1.8% was achieved. The granulation mixture was milled using a COMIL® to achieve a target particle size distribution of 250 μm (d90) and 100 μm (d50).

The extragranular excipients glycerol behenate (COMPRITOL®, 1.5 kg) and a second portion of silicon dioxide (SYLOID®, 0.25 kg) were added to the single pot processor and the extragranular excipients and milled granulation mixture were blended for 10 minutes at 10 RPM. The blend was compressed to prepare tablet cores having a weight of 120 mg and a hardness greater than or equal to 40 N. An aqueous solution containing 9.7% HPMC and 0.3% Polyethylene Glycol 1450 was prepared for use as a tablet coating solution. The tablet cores were coated with a sufficient amount of the coating solution to provide a 3% weight gain and a target tablet weight of 123.6 mg.

The 0.50 mg Phase III tablet (i.e., the tablet corresponding to Table 10-B of Example 10) can be prepared in a similar manner to the batch of the 0.75 mg Phase III tablet described above with the amount of atrasentan monohydrochloride, L-cysteine hydrochloride monohydrate, and lactose monohydrate adjusted accordingly (i.e., the amount of atrasentan monohydrochloride used in each batch of the 0.50 mg Phase III tablets is 0.449 kg).

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

We claim:

1. A stable solid pharmaceutical dosage form comprising:
   from about 0.4 mg to about 0.85 mg atrasentan free base, or an equivalent amount of a pharmaceutically acceptable salt thereof; and
   L-cysteine, or a pharmaceutically acceptable salt thereof, wherein the mole ratio of L-cysteine, or a pharmaceutically acceptable salt thereof, to atrasentan free base, or a pharmaceutically acceptable salt thereof, is from about 2:1 to about 1:2.

2. The dosage form of claim 1, comprising about 0.75 mg atrasentan free base, or an equivalent amount of a pharmaceutically acceptable salt thereof.

3. The dosage form of claim 1, wherein the mole ratio of L-cysteine, or a pharmaceutically acceptable salt thereof, to atrasentan free base, or a pharmaceutically acceptable salt thereof, is about 1:1.

4. The dosage form of claim 1, further comprising from about 1 wt. % to about 5 wt. % of a binder selected from the group consisting of hydroxypropyl methylcellulose, hydroxypropyl ethylcellulose, and hydroxypropyl cellulose.

5. The dosage form of claim 4, wherein the polymeric binder is hydroxypropyl methylcellulose.

6. The dosage form of claim 4, further comprising:
   from about 1 wt. % to about 6 wt. % of a disintegrant selected from cross-linked polyvinyl pyrrolidone, sodium starch glycolate and sodium croscarmellose; and
   from about 85 wt. % to about 99 wt. % of a diluent selected from lactose, mannitol, isomalt, microcrystalline cellulose, dicalcium phosphate, and combinations thereof.

7. The dosage form of claim 6, wherein the disintegrant is crospovidone and the diluent is lactose.

8. The dosage form of claim 6, further comprising:
   from about 0.1 wt. % to about 0.8 wt. % of a glidant; and
   from about 0.5 wt. % to about 2 wt. % of a lubricant.

9. The dosage form of claim 8, wherein the glidant is silicon dioxide and the lubricant is glyceryl behenate.

10. The dosage form of claim 1, further comprising:
    from about 1 wt. % to about 5 wt. % hydroxypropyl methylcellulose;
    from about 1 wt. % to about 6 wt. % crospovidone;
    from about 85 wt. % to about 99 wt. % lactose;
    from about 0.1 wt. % to about 0.8 wt. % silicon dioxide; and
    from about 0.5 wt. % to about 2 wt. % glyceryl behenate.

11. The dosage form of claim 10 wherein the dosage form is a tablet core, wherein said tablet core further comprises a film coating disposed thereon.

\* \* \* \* \*